(12) United States Patent
Van Liere et al.

(10) Patent No.: US 11,179,142 B2
(45) Date of Patent: *Nov. 23, 2021

(54) BIOPSY DEVICE

(71) Applicant: C. R. Bard, Inc., Franklin Lakes, NJ (US)

(72) Inventors: Chad C. Van Liere, Phoenix, AZ (US); Rory M. Schlarb, Paradise Valley, AZ (US)

(73) Assignee: C.R. Bard, Inc., Franklin Lakes, NJ (US)

( * ) Notice: Subject to any disclaimer, the term of this patent is extended or adjusted under 35 U.S.C. 154(b) by 156 days.

This patent is subject to a terminal disclaimer.

(21) Appl. No.: 16/584,275

(22) Filed: Sep. 26, 2019

(65) Prior Publication Data

US 2020/0015796 A1 Jan. 16, 2020

Related U.S. Application Data

(63) Continuation of application No. 15/565,967, filed as application No. PCT/US2015/028902 on May 1, 2015, now Pat. No. 10,463,350.

(51) Int. Cl.
*A61B 10/00* (2006.01)
*A61B 10/02* (2006.01)

(52) U.S. Cl.
CPC ...... *A61B 10/0283* (2013.01); *A61B 10/0275* (2013.01); *A61B 2010/0208* (2013.01); *A61B 2010/0225* (2013.01)

(58) Field of Classification Search
CPC ............ A61B 10/0283; A61B 10/0275; A61B 2010/0208; A61B 2010/0225
See application file for complete search history.

(56) References Cited

U.S. PATENT DOCUMENTS 737,293 A 8/1903 Summerfeldt
1,585,934 A 5/1926 Muir
(Continued)

FOREIGN PATENT DOCUMENTS

CN 101011268 A 8/2007
CN 101032420 A 9/2007
(Continued)

OTHER PUBLICATIONS

Maxim; Maxim8606; USB/AC Adapter, Li+ Linear Battery Charger with Integrated 50m Omega Battery Switch in TDFN; http://datasheets.maxim-ic.com/en/ds/MAX8606.pdf; Dec. 2008; pp. 1-14; Rev 1.

*Primary Examiner* — Andrey Shostak
(74) *Attorney, Agent, or Firm* — Dinsmore & Shohl LLP

(57) ABSTRACT

A biopsy device is configured such that: a first retraction of a charge handle moves a cannula slide and a sampling slide in unison in a proximal direction to charge and retain a sampling spring in a charged state, and to charge a vacuum system; a first return of the charge handle returns the charge handle to a home position; a second retraction of the charge handle moves the charge handle to a retracted position; a second return of the charge handle to the home position moves the cannula slide to charge a cannula retract spring and retain the cannula retract spring in a charged state; and a third retraction of the charge handle moves the carriage assembly as a whole in the proximal direction to charge a prime pierce spring and to retain the prime pierce spring in a charged state.

25 Claims, 16 Drawing Sheets

(56) References Cited

U.S. PATENT DOCUMENTS

| | | |
|---|---|---|
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,289,669 A | 12/1966 | Dwyer et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 3,996,935 A | 12/1976 | Banko |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,881,551 A | 11/1989 | Taylor |
| 4,893,635 A | 1/1990 | de Groot et al. |
| 4,907,598 A | 3/1990 | Bauer |
| 4,907,599 A | 3/1990 | Taylor |
| 4,924,878 A | 5/1990 | Nottke |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,121,751 A | 6/1992 | Panalletta |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| D333,183 S | 2/1993 | Cerola |
| 5,183,052 A | 2/1993 | Terwilliger |
| 5,197,484 A | 3/1993 | Kornberg et al. |
| 5,211,627 A | 5/1993 | William |
| 5,223,012 A | 6/1993 | Best et al. |
| D337,821 S | 7/1993 | Tan |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,254,117 A | 10/1993 | Rigby et al. |
| 5,282,476 A | 2/1994 | Terwilliger |
| 5,282,477 A | 2/1994 | Bauer |
| 5,290,253 A | 3/1994 | Kira |
| 5,305,762 A | 4/1994 | Acorn et al. |
| 5,324,306 A | 6/1994 | Makower et al. |
| 5,334,183 A | 8/1994 | Wuchinich |
| 5,335,671 A | 8/1994 | Clement |
| 5,335,672 A | 8/1994 | Bennett |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,612,738 A | 3/1997 | Kim |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |

(56) References Cited

U.S. PATENT DOCUMENTS

| | | |
|---|---|---|
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,032,673 A | 3/2000 | Savage et al. |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,494,844 B1 | 12/2002 | Van Bladel et al. |
| 6,527,731 B2 | 3/2003 | Weiss et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| D478,987 S | 8/2003 | Groenke et al. |
| 6,620,111 B2 | 9/2003 | Stephens et al. |
| 6,626,848 B2 | 9/2003 | Neuenfeldt |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,071 B2 | 2/2004 | Burbank et al. |
| 6,689,072 B2 | 2/2004 | Kaplan et al. |
| 6,695,786 B2 | 2/2004 | Wang et al. |
| 6,695,791 B2 | 2/2004 | Gonzalez |
| 6,702,832 B2 | 3/2004 | Ross et al. |
| 6,712,773 B1 | 3/2004 | Viola |
| 6,712,774 B2 | 3/2004 | Voegele et al. |
| 6,719,691 B2 | 4/2004 | Kritzman et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,758,848 B2 | 7/2004 | Burbank et al. |
| 6,764,495 B2 | 7/2004 | Lee et al. |
| 6,808,505 B2 | 10/2004 | Kadan |
| 6,832,990 B2 | 12/2004 | Kortenbach et al. |
| 6,840,950 B2 | 1/2005 | Stanford et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,969,358 B2 | 11/2005 | Baltschun et al. |
| 6,984,213 B2 | 1/2006 | Horner et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| 7,066,893 B2 | 6/2006 | Hibner et al. |
| D525,583 S | 7/2006 | Vu |
| 7,108,660 B2 | 9/2006 | Stephens et al. |
| 7,131,951 B2 | 11/2006 | Angel |
| 7,153,274 B2 | 12/2006 | Stephens et al. |
| 7,156,814 B1 | 1/2007 | Williamson, IV et al. |
| 7,156,815 B2 | 1/2007 | Leigh et al. |
| 7,169,114 B2 | 1/2007 | Krause |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,229,417 B2 | 6/2007 | Foerster et al. |
| 7,244,236 B2 | 7/2007 | Merkle |
| 7,252,641 B2 | 8/2007 | Thompson et al. |
| 7,276,032 B2 | 10/2007 | Hibner |
| 7,311,673 B2 | 12/2007 | Mueller, Jr. et al. |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,442,171 B2 | 10/2008 | Stephens et al. |
| 7,445,604 B2 | 11/2008 | Cash |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |

(56) References Cited

U.S. PATENT DOCUMENTS

| | | |
|---|---|---|
| 7,510,563 B2 | 3/2009 | Cesarini et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,556,622 B2 | 7/2009 | Mark et al. |
| 7,557,536 B2 | 7/2009 | Lobert et al. |
| 7,573,212 B2 | 8/2009 | Avis |
| 7,575,557 B2 | 8/2009 | Morton et al. |
| 7,588,176 B2 | 9/2009 | Timm et al. |
| 7,591,790 B2 | 9/2009 | Pflueger |
| 7,608,048 B2 | 10/2009 | Goldenberg |
| 7,611,475 B2 | 11/2009 | Spero et al. |
| 7,645,240 B2 | 1/2010 | Thompson et al. |
| 7,648,466 B2 | 1/2010 | Stephens et al. |
| 7,651,505 B2 | 1/2010 | Lubock et al. |
| 7,658,718 B2 | 2/2010 | Miller et al. |
| 7,662,109 B2 | 2/2010 | Hibner |
| 7,666,200 B2 | 2/2010 | Heisler |
| 7,670,299 B2 | 3/2010 | Beckman et al. |
| 7,693,567 B2 | 4/2010 | Tsonton et al. |
| 7,708,721 B2 | 5/2010 | Khaw |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 * | 6/2010 | Hibner ............... A61B 10/0275 600/565 |
| 7,740,597 B2 | 6/2010 | Cicenas et al. |
| 7,758,515 B2 | 7/2010 | Hibner |
| 7,762,961 B2 | 7/2010 | Heske et al. |
| 7,785,535 B2 | 8/2010 | Chen et al. |
| 7,794,411 B2 | 9/2010 | Ritchart et al. |
| 7,799,116 B2 | 9/2010 | Schwindt |
| 7,806,834 B2 | 10/2010 | Beckman et al. |
| 7,819,819 B2 | 10/2010 | Quick et al. |
| 7,828,746 B2 | 11/2010 | Teague |
| 7,828,747 B2 | 11/2010 | Heske et al. |
| 7,828,748 B2 | 11/2010 | Hibner |
| 7,837,630 B2 | 11/2010 | Nicoson et al. |
| 7,837,632 B2 | 11/2010 | Stephens et al. |
| 7,841,991 B2 | 11/2010 | Douglas et al. |
| 7,846,109 B2 | 12/2010 | Parihar et al. |
| 7,847,515 B2 | 12/2010 | Schroeck et al. |
| 7,854,706 B2 | 12/2010 | Hibner |
| 7,854,707 B2 | 12/2010 | Hibner et al. |
| 7,860,556 B2 | 12/2010 | Saadat |
| 7,862,517 B2 | 1/2011 | Tsonton et al. |
| 7,862,518 B2 | 1/2011 | Parihar |
| 7,867,173 B2 | 1/2011 | Hibner et al. |
| 7,871,384 B2 | 1/2011 | Thompson et al. |
| 7,883,476 B2 | 2/2011 | Miller et al. |
| 7,883,494 B2 | 2/2011 | Martin |
| 7,906,076 B2 | 3/2011 | Fischer |
| 7,914,462 B2 | 3/2011 | Hutchins et al. |
| 7,914,464 B2 | 3/2011 | Burdorff et al. |
| 7,959,580 B2 | 6/2011 | Mccullough et al. |
| 7,963,928 B2 | 6/2011 | Krause |
| 7,974,681 B2 | 7/2011 | Wallace et al. |
| 7,987,766 B1 | 8/2011 | Price |
| 7,988,642 B2 | 8/2011 | Hardin et al. |
| 8,002,713 B2 | 8/2011 | Heske et al. |
| 8,012,102 B2 | 9/2011 | McCullough et al. |
| 8,013,572 B2 | 9/2011 | Rodgers |
| 8,016,772 B2 | 9/2011 | Heske et al. |
| 8,016,844 B2 | 9/2011 | Privitera et al. |
| 8,016,855 B2 | 9/2011 | Whitman et al. |
| 8,034,003 B2 | 10/2011 | Pesce et al. |
| 8,042,689 B2 | 10/2011 | Fröjd et al. |
| 8,048,003 B2 | 11/2011 | Nicoson et al. |
| 8,052,614 B2 | 11/2011 | Heske et al. |
| 8,052,615 B2 | 11/2011 | Reuber et al. |
| 8,057,402 B2 | 11/2011 | Hibner et al. |
| 8,073,008 B2 | 12/2011 | Mehta et al. |
| 8,075,495 B2 | 12/2011 | Andreyko et al. |
| 8,075,496 B2 | 12/2011 | Deck et al. |
| 8,075,568 B2 | 12/2011 | Selis |
| 8,083,671 B2 | 12/2011 | Boulais et al. |
| 8,083,687 B2 | 12/2011 | Parihar |
| 8,109,885 B2 | 2/2012 | Heske et al. |
| 8,109,886 B2 | 2/2012 | Miller et al. |
| 8,118,755 B2 | 2/2012 | Hibner et al. |
| 8,128,577 B2 | 3/2012 | Viola |
| 8,129,955 B2 | 3/2012 | White et al. |
| 8,152,738 B2 | 4/2012 | Li et al. |
| 8,157,744 B2 | 4/2012 | Jorgensen et al. |
| 8,162,850 B2 | 4/2012 | Parihar et al. |
| 8,162,851 B2 | 4/2012 | Heske et al. |
| D659,828 S | 5/2012 | Horning et al. |
| 8,167,818 B2 | 5/2012 | Miller |
| 8,172,771 B2 | 5/2012 | Miller et al. |
| 8,172,773 B2 | 5/2012 | Heske et al. |
| 8,177,728 B2 | 5/2012 | Hibner et al. |
| 8,177,729 B2 | 5/2012 | Hibner et al. |
| 8,183,825 B2 | 5/2012 | Sa |
| 8,187,204 B2 | 5/2012 | Miller et al. |
| 8,187,294 B2 | 5/2012 | Miller et al. |
| 8,190,238 B2 | 5/2012 | Moll et al. |
| 8,192,370 B2 | 6/2012 | Miller |
| 8,202,229 B2 | 6/2012 | Miller et al. |
| 8,206,316 B2 | 6/2012 | Hibner et al. |
| 8,206,409 B2 | 6/2012 | Privitera et al. |
| 8,241,331 B2 | 8/2012 | Amin |
| 8,251,916 B2 | 8/2012 | Speeg et al. |
| 8,251,917 B2 | 8/2012 | Almazan |
| 8,261,847 B2 | 9/2012 | Ford et al. |
| 8,262,585 B2 | 9/2012 | Thompson et al. |
| 8,262,586 B2 | 9/2012 | Anderson et al. |
| 8,267,868 B2 | 9/2012 | Taylor et al. |
| 8,277,393 B2 | 10/2012 | Miller et al. |
| 8,282,573 B2 | 10/2012 | Shabaz et al. |
| 8,282,574 B2 | 10/2012 | Coonahan et al. |
| 8,283,890 B2 | 10/2012 | Videbaek |
| 8,287,465 B2 | 10/2012 | Hardin et al. |
| 8,287,466 B2 | 10/2012 | Weikel, Jr. et al. |
| 8,313,444 B2 | 11/2012 | Thompson et al. |
| 8,317,725 B2 | 11/2012 | Quick et al. |
| 8,343,069 B2 | 1/2013 | Uchiyama et al. |
| 8,357,103 B2 | 1/2013 | Mark et al. |
| 8,366,635 B2 | 2/2013 | Parihar et al. |
| 8,366,636 B2 | 2/2013 | Videbaek |
| 8,430,824 B2 | 4/2013 | Videbaek et al. |
| 8,430,825 B2 | 4/2013 | Mark |
| 8,430,827 B2 | 4/2013 | Nicoson et al. |
| 8,480,595 B2 | 7/2013 | Speeg et al. |
| 8,485,987 B2 | 7/2013 | Videbaek et al. |
| 8,485,989 B2 | 7/2013 | Videbaek |
| 8,491,496 B2 | 7/2013 | Hibner |
| 8,506,504 B2 | 8/2013 | Field et al. |
| 8,529,468 B2 | 9/2013 | Hoffa et al. |
| 8,529,593 B2 | 9/2013 | Berberich |
| 8,540,646 B2 | 9/2013 | Mendez-Coll |
| 8,574,167 B2 | 11/2013 | Smith et al. |
| 8,591,435 B2 | 11/2013 | Ritchart et al. |
| 8,594,339 B2 | 11/2013 | Dufresne et al. |
| 8,597,205 B2 | 12/2013 | Seiger et al. |
| 8,597,206 B2 | 12/2013 | Videback |
| 8,600,299 B2 | 12/2013 | Randall et al. |
| 8,672,860 B2 | 3/2014 | Moore et al. |
| 8,690,793 B2 | 4/2014 | Ranpura et al. |
| 8,696,650 B2 | 4/2014 | Quick et al. |
| 8,702,621 B2 | 4/2014 | Mccullough et al. |
| 8,702,622 B2 | 4/2014 | McCullough et al. |
| 8,702,623 B2 | 4/2014 | Parihar et al. |
| 8,708,928 B2 | 4/2014 | Videbaek |
| 8,708,929 B2 | 4/2014 | Videbaek |
| 8,708,930 B2 | 4/2014 | Videbaek |
| 8,721,563 B2 | 5/2014 | Taylor et al. |
| 8,728,003 B2 | 5/2014 | Taylor et al. |
| 8,728,004 B2 | 5/2014 | Heske et al. |
| 8,764,664 B2 | 7/2014 | Callahan et al. |
| 8,771,200 B2 | 7/2014 | Thompson et al. |
| 8,795,195 B2 | 8/2014 | Daw et al. |
| 8,808,197 B2 | 8/2014 | Videbaek et al. |
| 8,858,463 B2 | 10/2014 | Seiger et al. |

(56) References Cited

U.S. PATENT DOCUMENTS

| | | |
|---|---|---|
| 8,864,680 B2 | 10/2014 | VidebæK et al. |
| 8,926,527 B2 | 1/2015 | Jørgensen et al. |
| 8,932,233 B2 | 1/2015 | Haberstich et al. |
| 8,951,208 B2 | 2/2015 | Almazan |
| 8,951,209 B2 | 2/2015 | Heske et al. |
| 8,956,306 B2 | 2/2015 | Hibner |
| 8,961,430 B2 | 2/2015 | Coonahan et al. |
| 8,992,440 B2 | 3/2015 | Reuber et al. |
| 9,023,292 B2 | 5/2015 | Rostaing et al. |
| 9,044,227 B2 | 6/2015 | Shelton, IV et al. |
| 9,072,502 B2 | 7/2015 | Heske et al. |
| 9,095,326 B2 | 8/2015 | Ritchie et al. |
| 9,161,743 B2 | 10/2015 | Mccullough et al. |
| 9,162,884 B2 | 10/2015 | Hoon et al. |
| 9,173,641 B2 | 11/2015 | Chudzik et al. |
| 9,220,573 B2 | 12/2015 | Kendrick et al. |
| 9,282,949 B2 | 3/2016 | Videbaek |
| 9,332,972 B2 | 5/2016 | Boutaghou et al. |
| 9,345,457 B2 | 5/2016 | Speeg et al. |
| 9,345,458 B2 | 5/2016 | Videbaek et al. |
| 9,421,002 B2 | 8/2016 | Heske et al. |
| 9,439,631 B2 | 9/2016 | Heske et al. |
| 9,439,632 B2 | 9/2016 | Almazan |
| 9,445,790 B2 | 9/2016 | Zinn et al. |
| 9,451,968 B2 | 9/2016 | Miller et al. |
| 9,456,809 B2 | 10/2016 | Jorgensen et al. |
| 9,566,045 B2 | 2/2017 | Videbaek et al. |
| 9,638,770 B2 | 5/2017 | Dietz et al. |
| 9,655,599 B2 | 5/2017 | Chudzik et al. |
| 2001/0007925 A1 | 7/2001 | Ritchart et al. |
| 2001/0012919 A1 | 8/2001 | Terwilliger |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0067151 A1 | 6/2002 | Tanishita |
| 2002/0068878 A1 | 6/2002 | Jasonni et al. |
| 2002/0107043 A1 | 8/2002 | Adamson et al. |
| 2002/0120212 A1 | 8/2002 | Ritchart et al. |
| 2003/0093103 A1 | 5/2003 | Malackowski et al. |
| 2003/0163142 A1 | 8/2003 | Paltieli et al. |
| 2004/0030367 A1 | 2/2004 | Yamaki et al. |
| 2004/0092992 A1 | 5/2004 | Adams et al. |
| 2004/0158172 A1 | 8/2004 | Hancock |
| 2004/0162505 A1 | 8/2004 | Kaplan et al. |
| 2004/0220495 A1 | 11/2004 | Cahir et al. |
| 2004/0230188 A1 | 11/2004 | Cioanta et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0049521 A1 | 3/2005 | Miller et al. |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0177117 A1 | 8/2005 | Crocker et al. |
| 2005/0193451 A1 | 9/2005 | Quistgaard et al. |
| 2005/0209530 A1 | 9/2005 | Pflueger |
| 2005/0275378 A1 | 12/2005 | Canino et al. |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0116603 A1 | 6/2006 | Shibazaki et al. |
| 2006/0122535 A1 | 6/2006 | Daum |
| 2006/0178666 A1 | 8/2006 | Cosman et al. |
| 2006/0184063 A1 | 8/2006 | Miller |
| 2006/0241515 A1 | 10/2006 | Jones et al. |
| 2007/0016101 A1 | 1/2007 | Feldman et al. |
| 2007/0055173 A1 | 3/2007 | DeLonzor et al. |
| 2007/0090788 A1 | 4/2007 | Hansford et al. |
| 2007/0106176 A1 | 5/2007 | Mark et al. |
| 2007/0161925 A1 | 7/2007 | Quick et al. |
| 2007/0167943 A1 | 7/2007 | Janssen et al. |
| 2007/0208272 A1* | 9/2007 | Voegele ............ A61B 10/0275 600/564 |
| 2007/0213590 A1 | 9/2007 | Squicciarini |
| 2007/0213632 A1 | 9/2007 | Okazaki et al. |
| 2007/0270710 A1 | 11/2007 | Frass et al. |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0030170 A1 | 2/2008 | Dacquay et al. |
| 2008/0064925 A1 | 3/2008 | Gill et al. |
| 2008/0103411 A1 | 5/2008 | Van Bladel et al. |
| 2008/0125634 A1 | 5/2008 | Ryan et al. |
| 2008/0146965 A1 | 6/2008 | Privitera et al. |
| 2008/0161720 A1 | 7/2008 | Nicoson et al. |
| 2008/0208194 A1 | 8/2008 | Bickenbach |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0228104 A1 | 9/2008 | Uber et al. |
| 2009/0030442 A1 | 1/2009 | Potter et al. |
| 2009/0062624 A1 | 3/2009 | Neville |
| 2009/0082695 A1 | 3/2009 | Whitehead |
| 2009/0082696 A1* | 3/2009 | Nicoson ............ A61B 10/0275 600/566 |
| 2009/0087249 A1 | 4/2009 | Flagle et al. |
| 2009/0146609 A1 | 6/2009 | Santos |
| 2009/0204022 A1 | 8/2009 | Schwindt |
| 2009/0281453 A1 | 11/2009 | Tsonton et al. |
| 2010/0030020 A1 | 2/2010 | Sanders et al. |
| 2010/0063416 A1 | 3/2010 | Cicenas et al. |
| 2010/0152610 A1 | 6/2010 | Parihar et al. |
| 2011/0105946 A1 | 5/2011 | Sorensen et al. |
| 2011/0152715 A1 | 6/2011 | Delap et al. |
| 2011/0160611 A1 | 6/2011 | Ritchart et al. |
| 2011/0224577 A1 | 9/2011 | Park |
| 2012/0080332 A1 | 4/2012 | Shelton, IV et al. |
| 2012/0191009 A1 | 7/2012 | Hoon et al. |
| 2012/0253225 A1 | 10/2012 | Boutaghou et al. |
| 2012/0265096 A1 | 10/2012 | Mendez-Coll |
| 2013/0023789 A1 | 1/2013 | Anderson et al. |
| 2013/0165815 A1 | 6/2013 | Zinn et al. |
| 2013/0289441 A1 | 10/2013 | Videbaek et al. |
| 2014/0213932 A1* | 7/2014 | Knoll ................ A61B 10/0266 600/567 |
| 2014/0358032 A1 | 12/2014 | Videbaek et al. |
| 2014/0371585 A1 | 12/2014 | Thompson et al. |
| 2015/0018712 A1 | 1/2015 | Seiger et al. |
| 2015/0148704 A1* | 5/2015 | Swick ................ A61B 10/0275 600/567 |
| 2015/0190124 A1 | 7/2015 | Mccullough et al. |
| 2015/0223787 A1 | 8/2015 | Coonahan et al. |
| 2015/0238174 A1 | 8/2015 | Reuber et al. |
| 2016/0256138 A1 | 9/2016 | Videbaek et al. |
| 2016/0317133 A1 | 11/2016 | Orts et al. |
| 2016/0367229 A1 | 12/2016 | Jorgensen et al. |
| 2016/0367230 A1 | 12/2016 | Almazan |
| 2016/0374650 A1 | 12/2016 | Heske et al. |
| 2017/0042517 A1 | 2/2017 | Heske et al. |
| 2017/0181732 A1 | 6/2017 | Videbaek et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |

(56) References Cited

FOREIGN PATENT DOCUMENTS

| | | |
|---|---|---|
| EP | 1604615 A1 | 12/2005 |
| EP | 1642535 A1 | 4/2006 |
| EP | 1665989 A2 | 6/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| JP | 1-126957 A | 9/1987 |
| JP | H07289555 A | 11/1995 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9734531 A1 | 9/1997 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008040812 A1 | 4/2008 |
| WO | 2008131362 A2 | 10/2008 |
| WO | 2010107424 A1 | 9/2010 |
| WO | 2010120294 A1 | 10/2010 |
| WO | 2011019343 A1 | 2/2011 |
| WO | 2013158072 A1 | 10/2013 |
| WO | 2013068017 A9 | 3/2014 |
| WO | 2014153410 A1 | 9/2014 |
| WO | 2015069223 A1 | 5/2015 |

\* cited by examiner

BIOPSY DEVICE

CROSS-REFERENCE TO RELATED APPLICATIONS

This application is a continuation of U.S. patent application Ser. No. 15/565,967 filed Oct. 12, 2017, that issued as U.S. Pat. No. 10,463,350 on Nov. 5, 2019, which is a U.S. national phase of International Application No. PCT/US2015/028902, filed May 1, 2015.

BACKGROUND OF THE INVENTION

1. Field of the Invention

The present invention relates to biopsy devices, and, more particularly, to a handheld biopsy device having integrated vacuum assist to aid in tissue sample acquisition.

2. Description of the Related Art

A biopsy device has a sample retrieval mechanism configured to sever and remove a tissue sample from a patient. The sample retrieval mechanism may be in the form of a biopsy probe assembly that is configured with a biopsy needle having a sample retrieval opening. Some practitioners that perform biopsy procedures prefer a self-contained handheld biopsy device over that of a large console system. There are essentially two types of self-contained handheld biopsy devices: the partially disposable biopsy device and the fully disposable biopsy device.

A typical partially disposable biopsy device has a reusable handheld driver to which a disposable probe is releasably attached. The reusable handheld driver is typically battery powered, and includes electrical motor drives and an on-board vacuum pump to aid in sample acquisition and/or retrieval. Often, such biopsy devices are configured for single insertion multiple sample (SIMS) procedures. The disposable probe is used on a single patient, and then discarded, while the handheld driver is retained for reuse.

A typical fully disposable biopsy device has one or more mechanical drives, such as spring/latch arrangements, which permit the biopsy device to be manually cocked and fired for tissue sample acquisition. Such simple biopsy devices often are configured to acquire a single sample per insertion. Also, many of the fully disposable biopsy devices do not have vacuum to assist in sample acquisition. While some attempts have been made to include a vacuum assist feature in a fully disposable biopsy device, the vacuum produced typically is not sufficient to approach the performance of that of a partially disposable biopsy device as described above. Also, in a typical fully disposable biopsy device having vacuum assist, such vacuum is generated simultaneously with movement of the cutting cannula to sever the tissue sample, and thus the vacuum may be of limited value in acquiring the tissue sample.

What is needed in the art is a biopsy device that may be fully disposable, and which may generate a reserve of vacuum prior to a retraction of the cutting cannula to expose the sample retrieval opening of the biopsy needle, thus facilitating efficient vacuum application to aid in sample acquisition, and which is configured to be easy to use.

SUMMARY OF THE INVENTION

The present invention provides a biopsy device and a method of operating the biopsy device.

As used herein, the terms "first", "second", "third", etc., that precede an element name, e.g., first latch member, second latch member, etc., are for identification purposes to distinguish between different elements having similar characteristic, and are not intended to necessarily imply order, unless otherwise specified, nor are such terms intended to preclude the inclusion of additional similar elements.

The invention in one form is directed to a biopsy device having a housing, a biopsy needle including a stylet and a cannula, a carriage assembly including a carriage slide, a cannula slide and a sampling slide. The carriage slide has a stylet mount end wall and the cannula slide has a cannula mount end wall. A charge handle is slidably mounted to the housing. The charge handle has a home position and a retracted position. The biopsy device further includes a vacuum system positioned in the housing and carried by the carriage assembly. The vacuum system is charged to generate a vacuum when a sampling spring is compressed. The vacuum system includes a first vacuum pump, a second vacuum pump, a manifold and a control valve. The first vacuum pump has a first vacuum port. The second vacuum pump has a second vacuum port. The manifold has a first vacuum draw port, a second vacuum draw port, and a first vacuum application port. The control valve has a third vacuum draw port and a second vacuum application port. The first vacuum port of the first vacuum pump is coupled in fluid communication with the first vacuum draw port of the manifold. The second vacuum port of the second vacuum pump is coupled in fluid communication with the second vacuum draw port of the manifold. The first vacuum application port of the manifold is coupled in fluid communication with the third vacuum draw port of the valve. The second vacuum draw port of the control valve is coupled in fluid communication with a first lumen of the stylet. The manifold has a first one-way valve coupled in fluid communication with the first vacuum draw port and a second one-way valve coupled in fluid communication with the second vacuum draw port. Each of the first one-way valve and the second one-way valve is configured to release positive pressure to the atmosphere and to close upon establishment of vacuum. The control valve is operated by actuation of a cannula retract button of an actuator mechanism to apply the vacuum to a side sample port of the stylet simultaneously with movement of the cannula in a proximal direction by a force generated by a cannula retract spring to open the side sample port of the stylet.

The invention in another form is directed to a biopsy device that includes a housing having an actuator mechanism. A carriage assembly is movable relative to the housing. The carriage assembly includes a stylet mount wall that mounts a stylet having a sample port, a cannula slide that mounts a cutting cannula, a sampling slide movably interposed between the stylet mount wall and the cannula slide, and a carriage latch cover member. The cannula slide is longitudinally spaced from and movable relative to the stylet mount wall. The cannula slide has a first latch member, the sampling slide has a second latch member, and the carriage latch cover member has a third latch member. A charge handle is slidably mounted to the housing. The charge handle has a home position and a retracted position. A sampling spring is interposed between the stylet mount wall and the sampling slide. A cannula retract spring is interposed between, and connected to each of, the sampling slide and the cannula slide. A prime pierce spring is interposed between the carriage assembly and a portion of the housing. A vacuum system is configured to selectively supply a vacuum to the sample port of the stylet. The biopsy device is configured such that a first retraction of the charge handle moves the cannula slide and the sampling slide in unison in a proximal direction to charge the sampling spring, to latch the second latch member of the sampling slide with the carriage latch cover member to retain the sampling spring in a charged state, and to charge the vacuum system to generate the vacuum. A first return of the charge handle returns the charge handle to the home position. A second retraction of the charge handle moves the charge handle to the retracted position. A second return of the charge handle to the home position moves the cannula slide in a distal direction away from the sampling slide to charge the cannula retract spring and to latch the first latch member of the cannula slide with the carriage latch cover member to retain the cannula retract spring in a charged state. A third retraction of the charge handle moves the carriage assembly as a whole in the proximal direction to charge the prime pierce spring and to latch the third latch member of the carriage latch cover member with the actuator mechanism to retain the prime pierce spring in a charged state.

The invention in another form is directed to a biopsy device that includes a stylet positioned to extend on a longitudinal axis. The stylet has a first side wall configured to define a first lumen and a side sample port that extends through the first side wall to the first lumen. A cannula is coaxial with the stylet. The cannula has a second side wall configured to define a second lumen and a distal cutting edge. A housing has a proximal end wall, an intermediate wall, and a distal end portion spaced along the longitudinal axis. The distal end portion has a needle opening. The housing is configured to define a housing chamber between the proximal end wall and the distal end portion. The intermediate wall is interposed between the proximal end wall and the distal end portion. The stylet and the cannula are received through the needle opening. A proximal direction is from the distal end portion toward to the proximal end wall and a distal direction is from the proximal end wall toward the distal end portion. A charge handle is slidably mounted to the housing. The charge handle is configured to move between a home position and a retracted position. An actuator mechanism has a pierce button, a cannula retract button, and a sample acquisition button, and has a carriage latch strike. A carriage assembly is positioned in the housing chamber. The carriage assembly is configured to move longitudinally as a whole relative to the housing. The carriage assembly includes a carriage slide, a carriage latch cover member, a cannula slide, and a sampling slide. Each of the cannula slide and the sampling slide is configured to be movable relative to the carriage slide. The carriage slide has a stylet mount end wall configured to mount the stylet. The cannula slide has a cannula mount end wall configured to mount the cannula and has a first latch arm that extends in the proximal direction from the cannula mount end wall. The sampling slide is movably interposed between the stylet mount end wall of the carriage slide and the cannula mount end wall of the cannula slide. The sampling slide has a second latch arm that extends in the distal direction. The carriage latch cover member has a first latch strike, a second latch strike, and a carriage latch arm. The first latch strike is configured to releasably engage the first latch arm. The second latch strike is configured to releasably engage the second latch arm. The carriage latch arm is configured to releasably engage the carriage latch strike of the actuator mechanism. A sampling spring is interposed between the stylet mount end wall and the sampling slide. The sampling spring is configured to store mechanical energy when in a compressed state and configured to bias the sampling slide in the distal direction. The sampling spring is held in the compressed state when the second latch arm is engaged with the second latch strike. A vacuum system is positioned in the housing and carried by the carriage assembly. The vacuum system is charged to generate a vacuum when the sampling spring is compressed. A cannula retract spring is interposed between, and is connected to each of, the sampling slide and the cannula slide. The cannula retract spring is configured to store mechanical energy in an extended state to bias the cannula slide in the proximal direction. The cannula retract spring is releasably held in the extended state when the first latch arm is engaged with the first latch strike and the second latch arm is engaged with the second latch strike. A prime pierce spring is interposed between the intermediate wall of the housing and the stylet mount end wall. The prime pierce spring is configured to store mechanical energy when in a compressed state and is configured to bias the carriage assembly as a whole in the distal direction. The prime pierce spring is held in the compressed state when the carriage latch arm is engaged with the carriage latch strike of the actuator mechanism.

The biopsy device also may include an indexing mechanism that is movably coupled to the cannula mount end wall of the cannula slide. The cannula mount end wall has an indexing window. The indexing mechanism is configured to selectively cover a portion of the indexing window. The charge handle has a charge handle latch arm configured to pass through the indexing window when the charge handle is moved to the retracted position, and when the indexing mechanism is positioned to cover a portion of the indexing window, a subsequent movement of the charge handle in the distal direction toward the home position causes the charge handle latch arm to engage the indexing mechanism to move the cannula slide in the distal direction away from the sampling slide to charge the cannula retract spring.

The invention in another form is directed to a biopsy device that includes a housing having a longitudinal axis. The housing is configured to define a housing chamber. An actuator mechanism has a cannula retract button, a sample acquisition button, and a carriage latch strike. A carriage assembly is positioned in the housing chamber. The carriage assembly includes a carriage slide having a carriage base and a stylet mount wall. The carriage assembly further includes a sampling slide, a cannula slide and a carriage latch cover member. The cannula slide is longitudinally spaced from and movable relative to the stylet mount wall. The cannula slide has a first latch arm. The carriage latch cover member has a first latch strike and a second latch strike. The first latch arm is configured to releasably engage the first latch strike. A stylet is fixedly connected to stylet mount wall. The stylet is configured to extend along the longitudinal axis, and has a side sample port. A vacuum source is carried by the carriage assembly. The vacuum source is configured to selectively apply a vacuum to the side sample port of the stylet. A cannula is fixedly connected to the cannula slide. The cannula is coaxial with the stylet. The cannula has a distal cutting edge. The sampling slide is movably interposed between the stylet mount wall and the cannula slide. The sampling slide has a second latch arm and a latch arm deflection member. The second latch arm is configured to releasably engage the second latch strike of the carriage latch cover member. The latch arm deflection member is configured to engage the first latch arm of the cannula slide and deflect the first latch arm toward the carriage base. A sampling spring is interposed between the stylet mount wall and the sampling slide. The sampling spring is held in the compressed state when the second latch arm is engaged with the second latch strike. A cannula retract spring is interposed between, and is connected to each of, the sampling slide and the cannula slide. The cannula retract spring is releasably held in an extended state to store mechanical energy when the first latch arm is engaged with the first latch strike and the second latch arm is engaged with the second latch strike. A cocking mechanism has a charge handle, a biasing spring, and an indexing mechanism. The charge handle is slidably mounted to the housing and biased by the biasing spring in the distal direction to a home position. The charge handle is configured to move between the home position and a retracted position. The charge handle and the indexing mechanism in combination are configured to selectively move each of the sampling slide and the cannula slide based on sequential actuations of the charge handle, wherein: a first retraction of the charge handle moves the sampling slide and the cannula slide in unison in the proximal direction to compress the sampling spring, to engage the second latch arm with the second latch strike to retain the sampling spring in the compressed state, and to charge the vacuum source, the charge handle configured to return to the home position by force exerted by the biasing spring and to sequence the indexing mechanism to a next selection position; and a second retraction of the charge handle moves the charge handle to the retracted position, and during a return of the charge handle to the home position by force exerted by the biasing spring, the charge handle engages the cannula slide and the cannula slide is moved in the distal direction which in turn extends the cannula retract spring to the extended state and the first latch arm releasably engages the first latch strike to retain the cannula retract spring in the extended state, the cannula being positioned to close the side sample port of the stylet. The actuator mechanism is configured such that an actuation of the cannula retract button releases the first latch arm from the first latch strike to in turn release the cannula retract spring to exert a retraction force to move the cannula in the proximal direction to open the side sample port of the stylet and to simultaneously apply the vacuum to the side sample port; and an actuation of the sample acquisition button releases the second latch arm from the second latch strike to release the sampling spring to exert a force to move the cannula in the distal direction to close the side sample port.

The invention in another form is directed to a method of operating a biopsy device which includes providing a housing having an actuator mechanism; providing a carriage assembly movable relative to the housing, the carriage assembly including a stylet mount wall that mounts a stylet, a cannula slide that mounts a cutting cannula, a sampling slide movably interposed between the stylet mount wall and the cannula slide, and a carriage latch cover member, the cannula slide being longitudinally spaced from and movable relative to the stylet mount wall; providing a charge handle to sequentially move at least one of the cannula slide, the sampling slide, and the carriage assembly as a whole, the charge handle having a home position and a retracted position; providing a sampling spring interposed between the stylet mount wall and the sampling slide; providing a cannula retract spring interposed between, and connected to each of, the sampling slide and the cannula slide; providing a prime pierce spring interposed between the carriage assembly and a portion of the housing; providing a vacuum system to selectively supply a vacuum to a sample port of the stylet; retracting the charge handle a first time to move the cannula slide and the sampling slide in unison in a proximal direction to charge a sampling spring, to latch the sampling slide with the carriage latch cover member to retain the sampling spring in a charged state, and to charge the vacuum system with a vacuum; returning the charge handle a first time to the home position; retracting the charge handle a second time to the retracted position; returning the charge handle a second time to the home position to move the cannula slide in a distal direction relative to the sampling slide to charge the cannula retract spring and to latch the cannula slide with the carriage latch cover member to retain the cannula retract spring in a charged state; and retracting the charge handle a third time to move the carriage assembly as a whole in the proximal direction to charge the prime pierce spring and to latch the carriage latch cover member with the actuator mechanism to retain the prime pierce spring in a charged state.

An advantage of the present invention is that the biopsy device is fully disposable.

Another advantage of the present invention is that the biopsy device is fully mechanical with no electrical component, thus requiring no electrical power source.

According to at least one aspect of the invention, another advantage is that the biopsy device generates a reserve of vacuum prior to a retraction of the cutting cannula to expose the sample port of the biopsy needle, thus facilitating efficient vacuum application to aid in sample acquisition.

Another advantage of the present invention is that the biopsy device is configured to be easy to use.

The above listed advantages may be realized individually, or collectively, depending on the aspects of the present invention that are utilized in a particular implementation.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates an embodiment of the invention and such exemplification is not to be construed as limiting the scope of the invention in any manner.

DETAILED DESCRIPTION OF THE INVENTION

Figure 1:
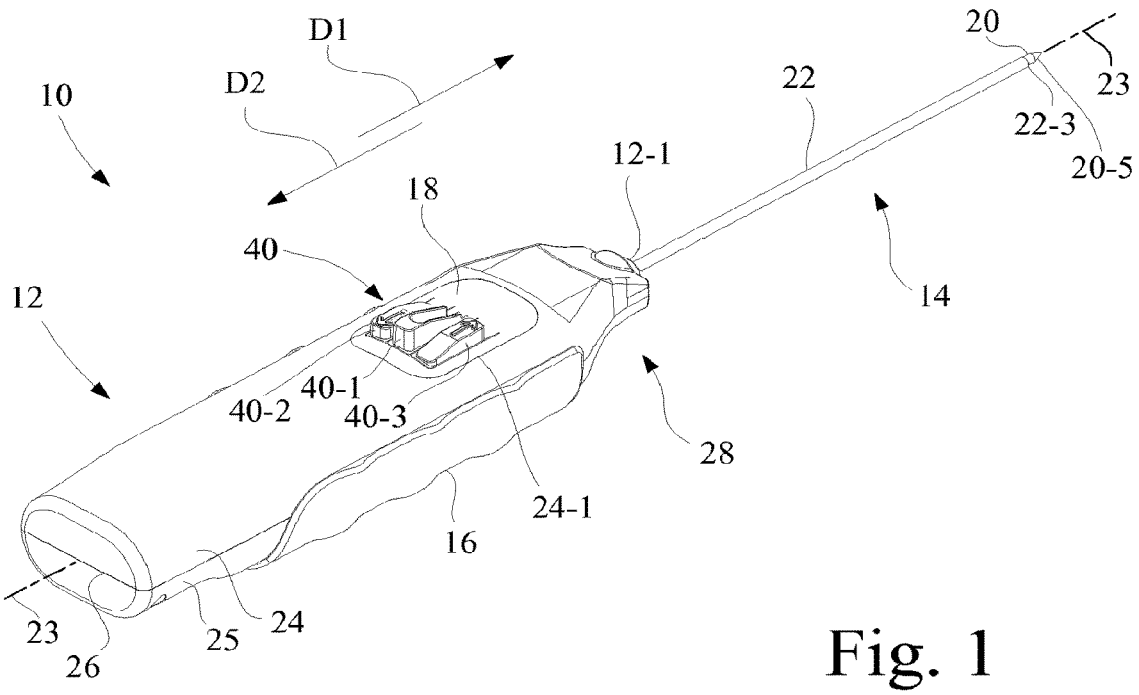
FIG. 1 is a perspective view of a biopsy device of the present invention.

Referring now to the drawings, and more particularly to FIGS. 1-5, there is shown a biopsy device 10 in accordance with an embodiment of the present invention. Biopsy device 10 is a self-contained and fully mechanical vacuum-assisted biopsy device that is configured as a single insertion single sample (SISS) biopsy device, and which is fully disposable. As used herein, the term "disposable" is used to refer to a device that is intended to be disposed of after use on a single patient. Accordingly, biopsy device 10 is intended for use in obtaining one or more tissue samples from a single patient during a single biopsy procedure, and is intended to be disposable in its entirety at the end of the biopsy procedure.

Figure 2:
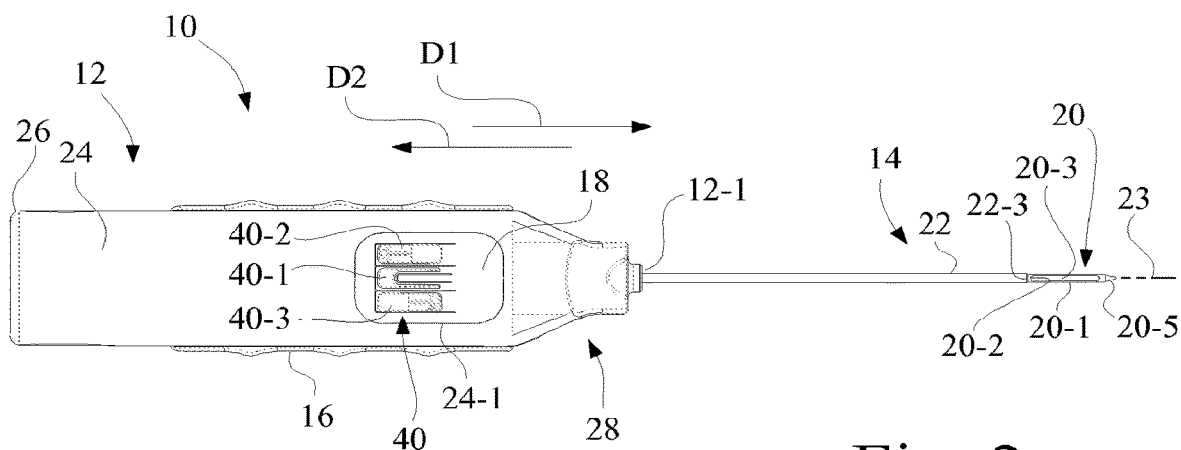
FIG. 2 is a top view of the biopsy device of FIG. 1.
Figure 3:
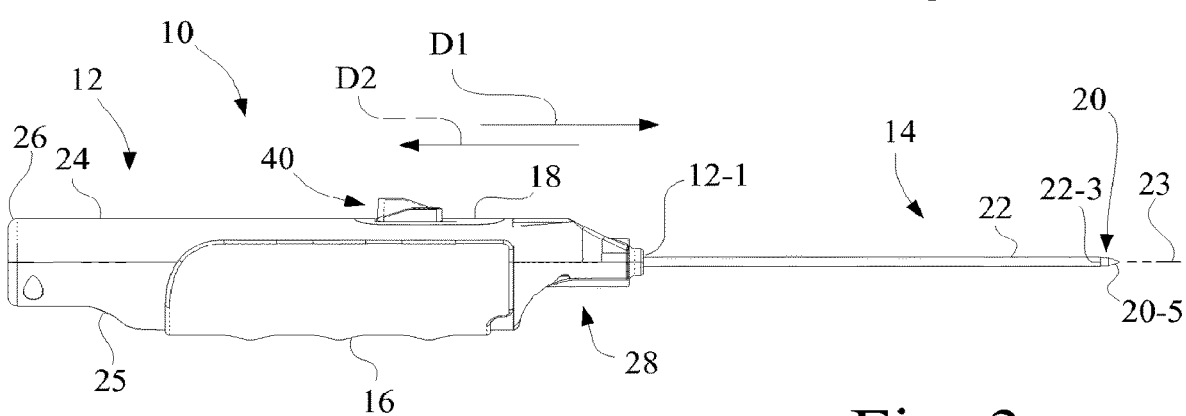
FIG. 3 is a side view of the biopsy device of FIG. 1.

Referring to FIGS. 1-3, biopsy device 10 includes a housing 12, a biopsy needle 14, a charge handle 16, and an actuator mechanism 18. Biopsy needle 14 includes a stylet 20 and a cannula 22. In the present embodiment, housing 12, charge handle 16 and actuator mechanism 18 are made of plastic, and stylet 20 and cannula 22 are made from a metallic material, such as stainless steel. In describing the orientation of components and the operation of biopsy device 10 in more detail below, for convenience, reference will be made to a distal direction D1 and a proximal direction D2 with respect to a longitudinal axis 23. The proximal direction D2 is a longitudinal direction opposite to distal direction D1.

As shown in FIGS. 1-3, biopsy needle 14 extends away from housing 12 along longitudinal axis 23 in the distal direction D1. Each of stylet 20 and cannula 22 of biopsy needle 14 is positioned to extend on the longitudinal axis 23. In the present embodiment, as depicted in FIGS. 1-3, cannula 22 is external to stylet 20, such that cannula 22 is arranged as the outer tube of the coaxial arrangement of stylet 20 and cannula 22. Stylet 20 and cannula 22 are sized such that stylet 20 is slidably received in cannula 22 in a close sliding fit, wherein the inside diameter of cannula 22 is slightly larger than the outside diameter of stylet 20 in a tolerance range of 0.01 millimeters (mm) to 1.0 mm.

In describing the invention, common directional terms such as upper, lower, up, down, top, bottom, right, left, vertical, horizontal, etc., may be used with respect to the orientation of biopsy device 10 shown in FIGS. 1 and 3-5, for convenience, to aid the reader in understanding the invention as presented in the figures of the drawings.

Figure 4:
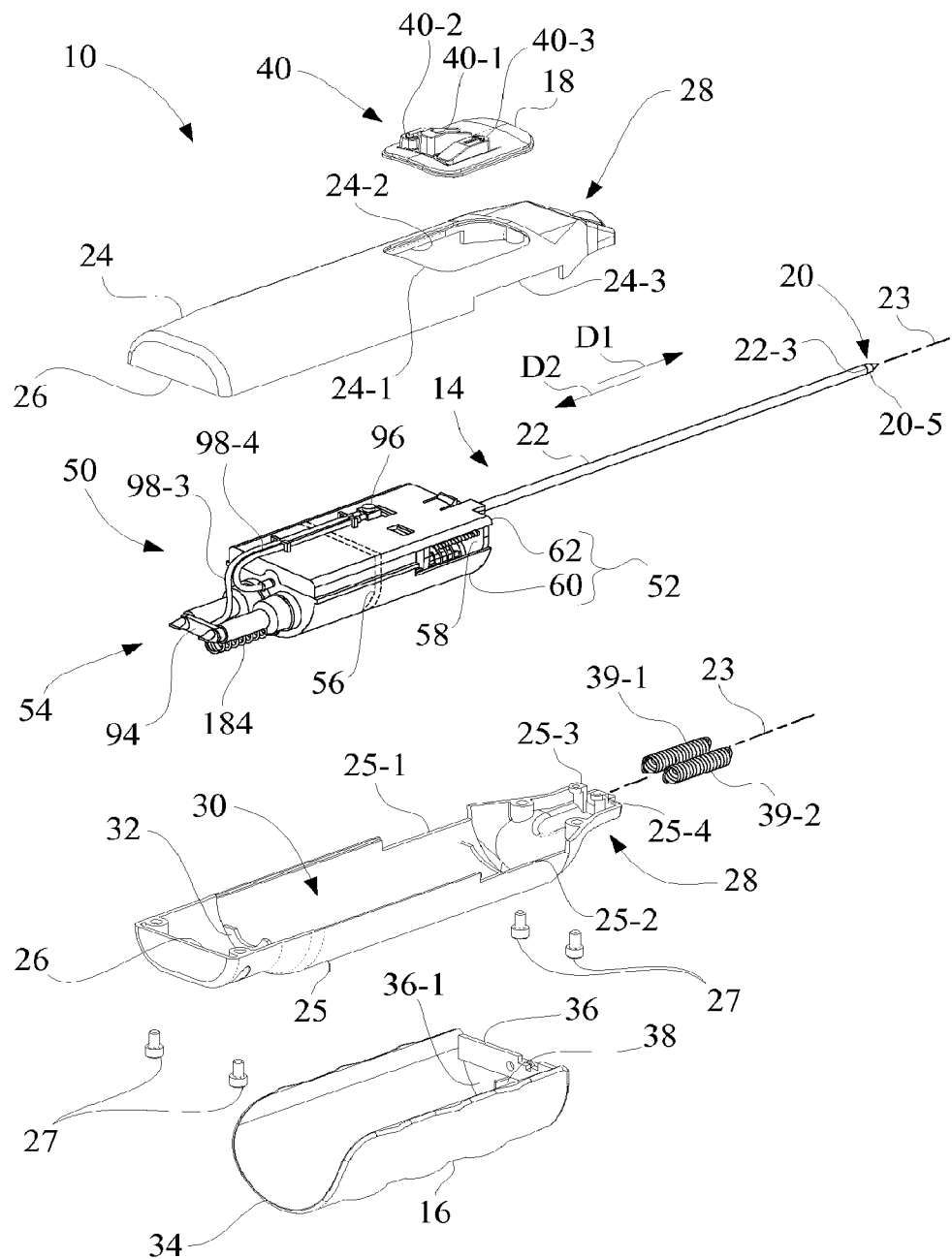
FIG. 4 is a partially exploded view of the biopsy device of FIG. 1, exposing the carriage assembly.
Figure 5:
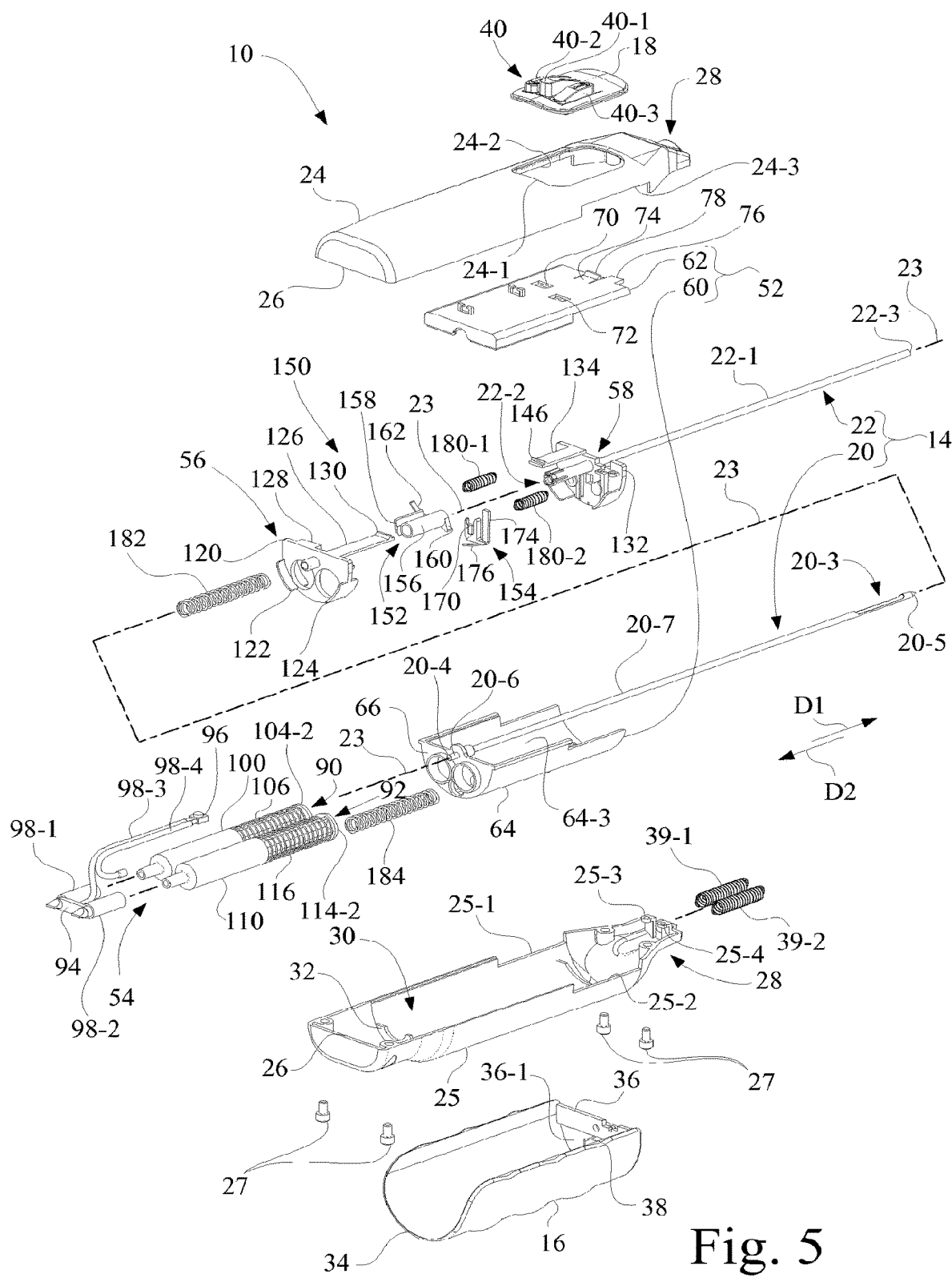
FIG. 5 is a fully exploded view of the biopsy device of FIG. 1.

In the orientation shown in FIG. 1, and referring also to FIGS. 4 and 5, housing 12 includes an upper case portion 24 and a lower case portion 25. Upper case portion 24 is jointed to lower case portion 25 by removable fasteners 27, such as screws. Upper case portion 24 of housing 12 has an opening 24-1, and opposing upper slots 24-2, 24-3. Opening 24-1 is configured to receive and mount actuator mechanism 18. Alternatively, actuator mechanism 18 may be formed integral with upper case portion 24 of housing 12 at the location of opening 24-1. Lower case portion 25 is configured with opposing guide rails 25-1, 25-2 which define a lower slot, which in conjunction with the opposing upper slots 24-2, 24-3 of upper case portion 24, slidably mount charge handle 16.

Upper case portion 24 and lower case portion 25 of housing 12 collectively define a proximal end wall 26 and a distal end portion 28 spaced from proximal end wall 26 along a longitudinal axis 23. The distal direction D1 is in a direction from proximal end wall 26 toward distal end portion 28, e.g., in a direction of the extent of biopsy needle 14 away from housing 12 and away from the user. The proximal direction D2 (opposite distal direction D1) is in a direction from distal end portion 28 toward proximal end wall 26, e.g., toward the user.

Housing 12 is configured to define a housing chamber 30 between proximal end wall 26 and distal end portion 28. In the present embodiment, lower case portion 25 of housing 12 further includes an intermediate wall 32 that is interposed between proximal end wall 26 and distal end portion 28. Referring to FIG. 1, distal end portion 28 has a needle opening 12-1 configured to receive biopsy needle biopsy needle 14, with longitudinal axis 23 passing through needle opening 12-1 and through the longitudinal extent of biopsy needle 14. Proximal end wall 26 faces the user when the user grasps the biopsy device 10 in a normal operating fashion.

Charge handle 16 and actuator mechanism 18 provide the user with fully accessible control features used to operate biopsy device 10 in an intuitive manner to obtain a tissue sample from suspect tissue of a patient via biopsy needle 14.

Charge handle 16 is used to ready biopsy device 10 for performing a biopsy procedure by facilitating the generation of vacuum and preparing biopsy needle 14 for severing and collecting the tissue sample.

Figure 6:
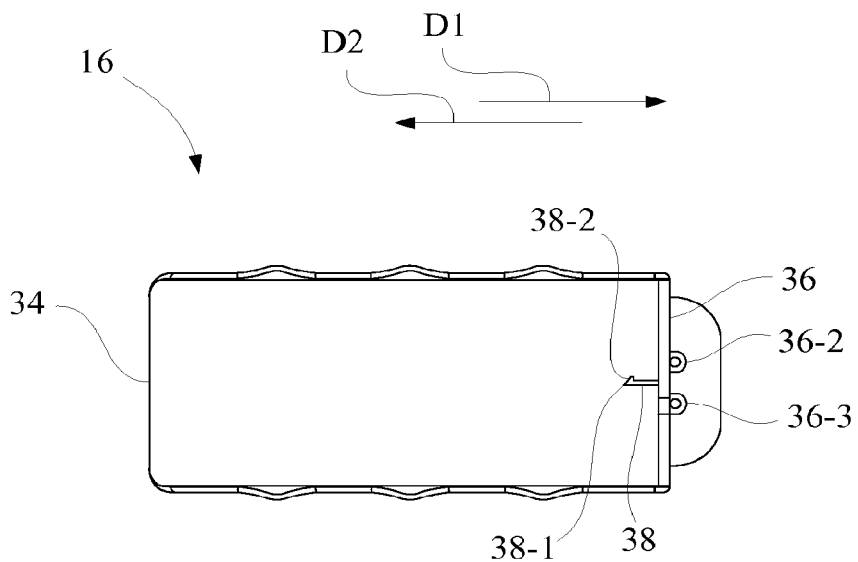
FIG. 6 is a top view of the charge handle of the biopsy device of FIG. 1.

As shown in FIGS. 4-6, charge handle 16 has a U-shaped charge handle body 34, a charge handle end wall 36, and a charge handle latch arm 38. Charge handle latch arm 38 extends in a cantilever manner in the proximal direction D2 from charge handle end wall 36. Charge handle end wall 36 laterally intersects U-shaped charge handle body 34 to define a handle mount opening 36-1 (see FIG. 5) having a half-circle shape located below charge handle end wall 36. During assembly, distal end portion 28 of lower case portion 25 is manipulated through handle mount opening 36-1, such that charge handle end wall 36 rests on the opposing guide rails 25-1, 25-2 of lower case portion 25 to slidably mount charge handle 16 in the laterally spaced lower case portion slots defined by the laterally spaced guide rails 25-1, 25-2 in conjunction with upper slots 24-2, 24-3 of upper case portion 24.

Charge handle latch arm 38 has a free end 38-1 having a laterally protruding catch 38-2. Charge handle latch arm 38 is configured to be longitudinally rigid, and laterally resilient in a direction substantially perpendicular to the longitudinal extent of charge handle latch arm 38. As used herein, the term "substantially perpendicular" is a direction having a range of deviation from perpendicular of plus or minus five degrees.

Referring to FIGS. 4-6, charge handle 16 is biased in distal direction D1 by a biasing mechanism formed by at least one biasing spring, and in the present embodiment, includes a pair of biasing springs 39-1, 39-2 interposed between housing 12 and charge handle 16. In the present embodiment, biasing springs 39-1, 39-2 are coil springs having a contracted relaxed state. In particular, biasing spring 39-1 is attached at its ends to spring attachment loop 25-3 of lower case portion 25 of housing 12 (see FIGS. 4 and 5) and to spring attachment loop 36-2 of charge handle end wall 36 of charge handle 16 (see FIG. 6). Likewise, biasing spring 39-2 is attached at its ends to spring attachment loop 25-4 of lower case portion 25 of housing 12 (see FIGS. 4 and 5) and to spring attachment loop 36-3 of charge handle end wall 36 of charge handle 16 (see FIG. 6). Charge handle 16 is configured to be grasped by a user's hand and to move between a home (distal) position, as depicted in FIGS. 1-3, and a retracted (proximal) position.

Referring again to FIGS. 1-3, actuator mechanism 18 is used to initialize the sequential operations of firing the biopsy needle in distal direction D1 to perform a piercing shot into tissue to be biopsied, to apply vacuum and open a sample port in biopsy needle 14, and to operate biopsy needle 14 to sever a tissue sample, as more fully described below.

Figure 7A:
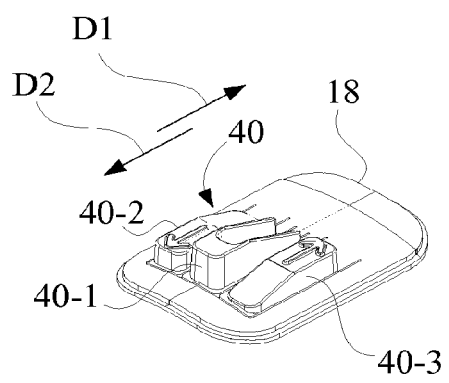
FIG. 7A is a top perspective view of the actuator mechanism of the biopsy device of FIG. 1.
Figure 7B:
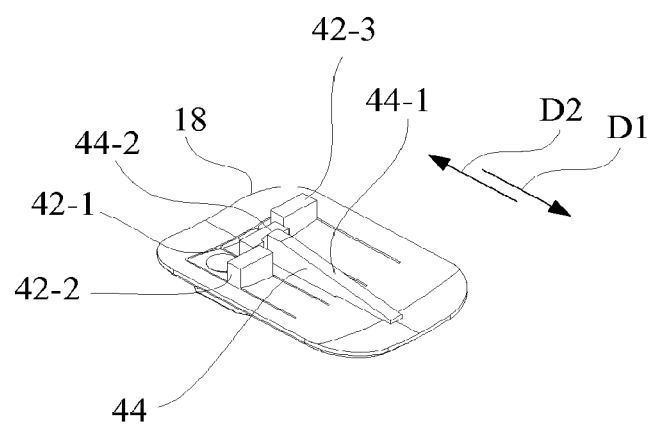
FIG. 7B is a bottom perspective view of the actuator mechanism of the biopsy device of FIG. 1.

Referring also to FIGS. 7A and 7B, actuator mechanism 18 includes three control buttons 40, individually identified as a pierce button 40-1, a cannula retract button 40-2, and a sample acquisition button 40-3, each of which is accessible to the user from the exterior of biopsy device 10. As shown in FIG. 7B, each of the control buttons 40 includes a mechanical extension that serves as respective actuator portions 42-1, 42-2, 42-3.

Also, as shown in FIG. 7B, actuator mechanism 18 further includes a carriage latch strike 44. In the present embodiment, carriage latch strike 44 is configured as an inverted ramp having a downwardly facing ramp surface 44-1 that diverges in the proximal direction D2 to define a proximal end face 44-2.

Referring again to FIGS. 4 and 5, biopsy device 10 further includes a carriage assembly 50 that is positioned and slidably contained in housing chamber 30 of housing 12. Carriage assembly 50 is configured to move longitudinally along longitudinal axis 23 as a whole relative to housing 12, and is configured to mount biopsy needle 14, as more fully described below.

As shown in FIGS. 4 and 5, carriage assembly 50 includes a prime pierce carriage 52, a cannula slide 58, a sampling slide 56, and a vacuum system 54. As used herein, the term "prime" is used to mean a function associated with readying, i.e., cocking, biopsy device 10 for performing a tissue piercing function by having both stylet 20 and cannula 22 retracted in preparation for "piercing". The term "pierce" is used to mean a function associated with firing stylet 20 and cannula 22 simultaneously in distal direction D1 such that biopsy needle 14 punctures the tissue of a patient at the desired location. The term "slide" is a mechanical structure having a guide that is configured to move along a predefined path defined by another mechanical structure. In the present embodiment, each of prime pierce carriage 52, cannula slide 58, and sampling slide 56 are configured to move along a substantially linear path. The term "substantially linear path" is a path having a range of deviation from a straight line of plus or minus three degrees along the length of the path.

Figure 8:
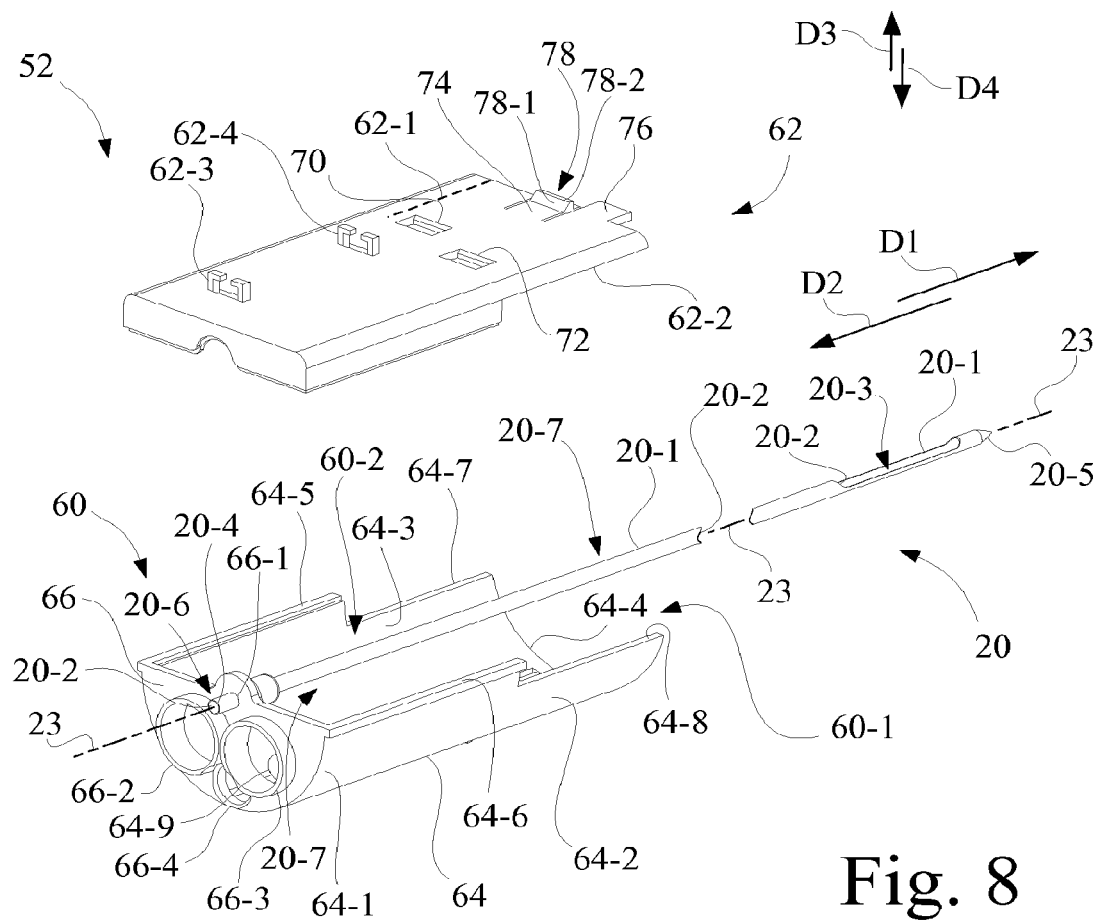
FIG. 8 is a perspective view of a prime pierce carriage of the carriage assembly of FIGS. 4 and 5, with the carriage latch cover member separated from the carriage slide.

Referring now also to FIG. 8, prime pierce carriage 52 includes carriage slide 60 serving as a lower prime pierce carriage portion and a carriage latch cover member 62 serving as an upper prime pierce carriage portion. Referring also to FIG. 5, sampling slide 56 and cannula slide 58 are individually, as well as collectively, longitudinally movable relative to prime pierce carriage 52 formed by carriage slide 60 and carriage latch cover member 62. Each of prime pierce carriage 52, sampling side 56 and cannula slide 58 is formed of plastic.

Carriage slide 60 of prime pierce carriage 52 of carriage assembly 50 has a carriage base 64 and a stylet mount end wall 66. In the present embodiment, carriage base 64 and stylet mount end wall 66 are formed as a unitary carriage structure.

Carriage base 64 of carriage slide 60 is configured to define a U-shaped wall 64-1 having a U-shaped exterior surface 64-2 and a U-shaped interior surface 64-3, thus having a U-shaped cross-section that extends in the distal direction D1 from stylet mount end wall 66 to define a U-shaped distal edge 64-4, a pair of laterally spaced upper mounting edges 64-5, 64-6, and a pair of laterally spaced recessed slot edges 64-7, 64-8. Extending upwardly and proximally from U-shaped interior surface 64-3 is a longitudinally oriented prime pierce spring mount post 64-9.

U-shaped exterior surface 64-2 corresponds to the interior shape of housing chamber 30, and is in sliding contact with housing chamber 30, with housing chamber 30 serving as a longitudinal guide for carriage assembly 50. U-shaped distal edge 64-4 defines an open distal end 60-1 of carriage slide 60. The pair of laterally spaced upper mounting edges 64-5, 64-6 in conjunction with the pair of laterally spaced recessed slot edges 64-7, 64-8 further define an open top 60-2 of carriage slide 60.

Stylet mount end wall 66 has a stylet hole 66-1, a first pump mounting opening 66-2 and a second pump mounting opening 66-3, and a prime pierce spring opening 66-4. Prime pierce spring opening 66-4 is axially aligned with prime pierce spring mount post 64-9 of carriage base 64 of carriage slide 60. Stylet hole 66-1 is configured to fixedly mount stylet 20, e.g., by a press fit and/or adhesive coupling. First pump mounting opening 66-2 and second pump mounting opening 66-3 are configured to mount a pair of syringe-type vacuum pumps of vacuum system 54, as will be more fully described below.

As best shown in FIG. 8, and with reference to FIGS. 1-5, stylet 20 of biopsy needle 14 has a side wall 20-1 configured to define a lumen 20-2 and a side sample port 20-3 that extends through side wall 20-1 to lumen 20-2. Stylet 20 has an open first end 20-4 and a closed second end 20-5. The closed second end 20-5 defines a distal piercing tip. Lumen 20-2 is in fluid communication with the open first end 20-4 and side sample port 20-3.

A proximal portion 20-6 of stylet 20 extends in a proximal direction D2 away from stylet mount end wall 66 and a distal portion 20-7 of stylet 20 extends in the distal direction D1 away from stylet mount end wall 66. The distal portion 20-7 of stylet 20 extends in the distal direction D1 beyond the distal extent of carriage base 64 and carriage latch cover member 62, and is received through needle opening 12-1 of housing 12 (see also FIG. 1).

Carriage latch cover member 62 is configured to attach, e.g., a snap fit and/or adhesive, to the pair of laterally spaced upper mounting edges 64-5, 64-6 of carriage base 64. Carriage latch cover member 62 includes laterally spaced recessed slot edges 62-1, 62-2 that are respectively vertically opposed to the laterally spaced recessed slot edges 64-7, 64-8 of carriage base 64. Carriage latch cover member 62 covers the open top 60-2 of carriage slide 60, and extends over carriage base 64 of carriage slide 60 to define an interior region in which cannula slide 58 may move longitudinally relative to stylet mount end wall 66. In particular, the U-shaped interior surface 64-3 of U-shaped wall 64-1 of carriage slide 60 in conjunction with open distal end 60-1 of carriage slide 60 are configured to slidably receive and longitudinally guide sampling slide 56 and cannula slide 58.

Carriage latch cover member 62 is configured to facilitate a selective longitudinal coupling and uncoupling of carriage slide 60 with each of sampling slide 56 and cannula slide 58. Carriage latch cover member 62 has a latch strike 70, a latch strike 72, a carriage latch arm 74, and a deflector arm 76. Carriage latch cover member 62 further includes conduit mounts 62-3, 62-4.

In the present embodiment, each of latch strike 70 and latch strike 72 is configured as a latching notch. More particularly, each of latch strike 70 and latch strike 72 of carriage latch cover member 62 is configured as a rectangular opening having proximal and distal end walls oriented to be substantially perpendicular to longitudinal axis 23.

Carriage latch arm 74 is configured as a cantilever arm with a free end having an upwardly extending catch 78. Catch 78 is configured as ramp having an upwardly facing ramp surface 78-1 that diverges in the distal direction D1 to define a distal end face 78-2. Carriage latch arm 74 is configured to be longitudinally rigid, and vertically resilient in directions D3, D4 (e.g., up, down) substantially perpendicular to the longitudinal extent of carriage latch arm 74. Directions D3 and D4 are opposite directions.

When carriage assembly 50 is fully retracted in proximal direction D1 by operation of charge handle 16, as will be more fully described below, carriage latch arm 74 of carriage latch cover member 62 releasably engages the proximal end face 44-2 of carriage latch strike 44 of actuator mechanism 18 (see FIG. 7B) so as to couple, and prohibit relative movement between, carriage assembly 50 and housing 12, until carriage latch arm 74 is released by operation of pierce button 40-1 of actuator mechanism 18.

Figure 9:
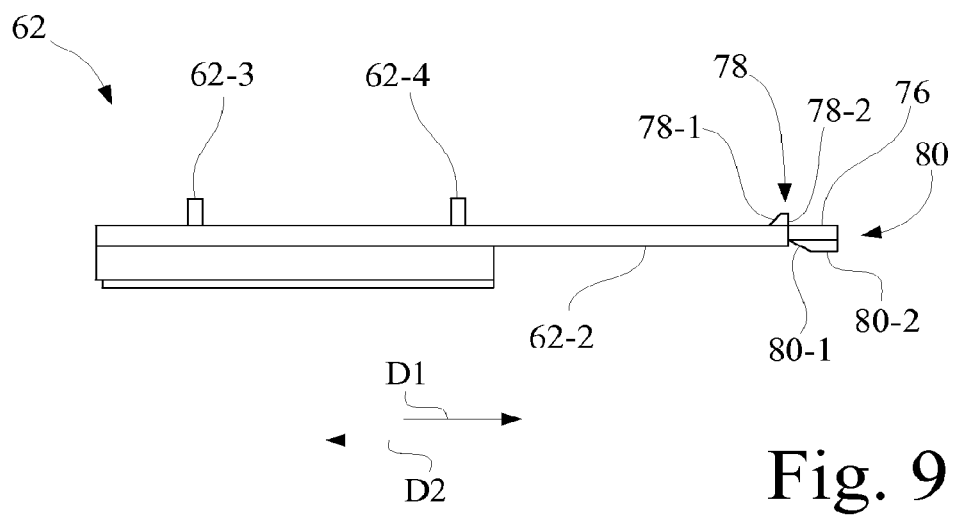
FIG. 9 is a side view of the carriage latch cover member of FIGS. 4, 5, and 8.

Referring also to FIG. 9, deflector arm 76 of carriage latch cover member 62 is configured to be longitudinally rigid, and also is laterally rigid in directions substantially perpendicular to the longitudinal extent of deflector arm 76. Deflector arm 76 is configured as a cantilever arm having a free end having a downwardly facing deflector head 80. Deflector head 80 has a downwardly facing ramp surface 80-1 that diverges in the distal direction D1 and terminates at a downwardly facing longitudinal surface 80-2.

Referring again to FIGS. 4 and 5, vacuum system 54 is mounted to, and carried by, carriage assembly 50, and is a completely self-contained within housing 12 of biopsy device 10. More particularly, referring also to FIG. 10, vacuum system 54 is mounted to prime pierce carriage 52 of carriage assembly 50.

Figure 10:
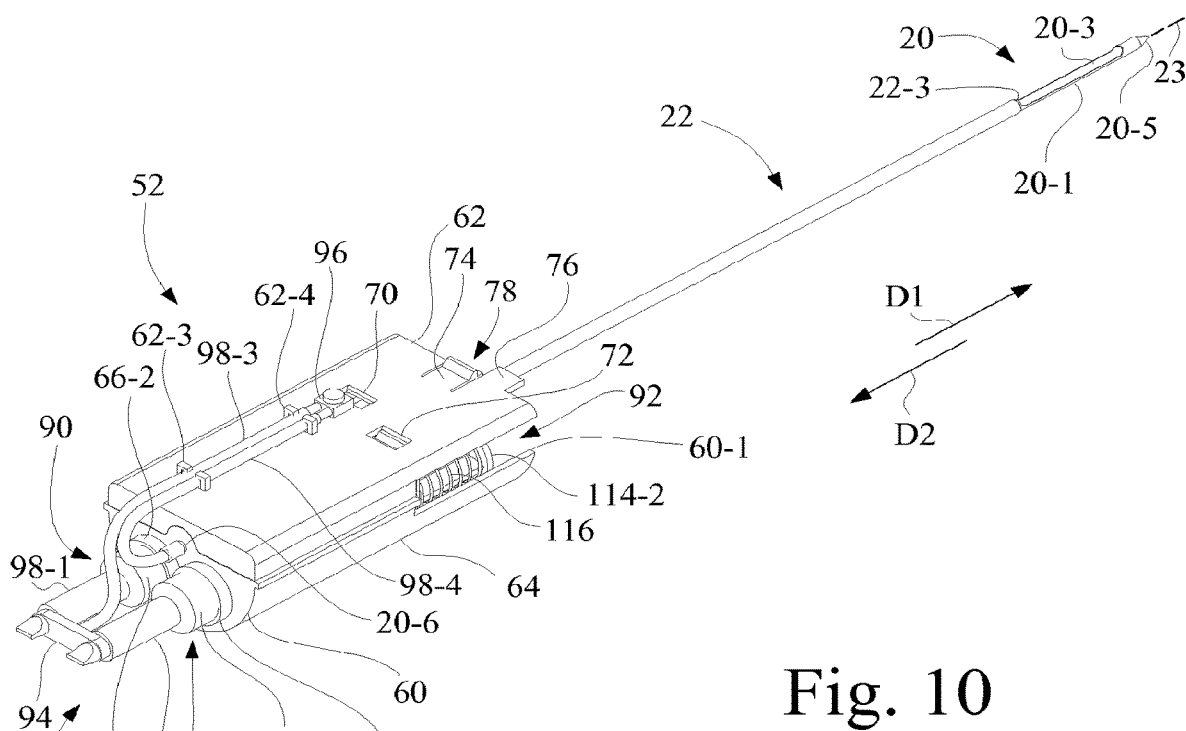
FIG. 10 is an enlarged view of the carriage assembly of FIGS. 4 and 5.
Figure 11:
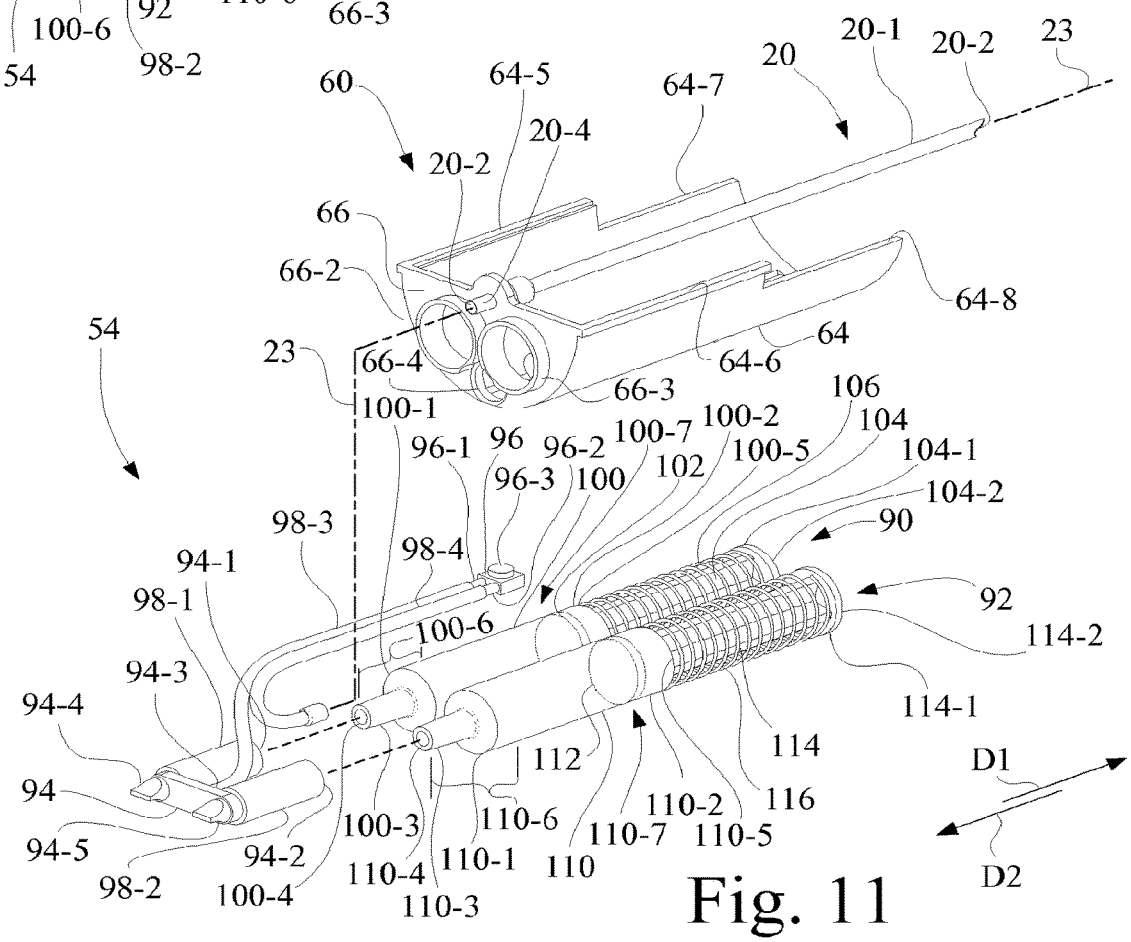
FIG. 11 is an exploded view showing a portion of the carriage assembly of FIG. 10 that exposes the vacuum system, and with the carriage latch cover member removed.

Referring to FIGS. 5, 10 and 11, vacuum system 54 includes a vacuum pump 90, a vacuum pump 92, a manifold 94, a control valve 96, and flexible connection conduits 98-1, 98-2, 98-3, and 98-4.

Referring particularly to FIG. 11, vacuum pump 90 is a syringe-type vacuum pump. Vacuum pump 90 includes an elongate cylinder 100 having a first end 100-1 and a second end 100-2. Extending from first end 100-1 is a tip portion 100-3 that defines a first vacuum port 100-4. Second end 100-2 has a first opening 100-5. A first piston 102 is slidably received in elongate cylinder 100 through first opening 100-5. A first plunger 104 is attached to, or integrally formed with, first piston 102. First plunger 104 is configured to extend from second end 100-2 of elongate cylinder 100. First plunger 104 has a free end 104-1 having a head 104-2. A first vacuum spring 106 is interposed between second end 100-2 of elongate cylinder 100 and head 104-2 of first plunger 104. First vacuum spring 106 is configured to store mechanical energy when in a compressed state and, in the orientation shown, is configured to bias first piston 102 in the distal direction D1 to establish a vacuum at first vacuum port 100-4.

Vacuum pump 92 also is a syringe-type vacuum pump, and is configured identical to vacuum pump 90. Vacuum pump 92 includes an elongate cylinder 110 having a first end 110-1 and a second end 110-2. Extending from first end 110-1 is a tip portion 110-3 that defines a second vacuum port 110-4. Second end 110-2 defines a second opening 110-5. A second piston 112 is slidably received in elongate cylinder 110 through second opening 110-5. A second plunger 114 is attached to, or formed integrally with, second piston 112. Second plunger 114 configured to extend from second end 110-2 of elongate cylinder 110. Second plunger 114 has a free end 114-1 having a head 114-2. A second vacuum spring 116 is interposed between second end 110-2 of elongate cylinder 110 and head 114-2 of second plunger 114. Second vacuum spring 116 is configured to store mechanical energy when in a compressed state and, in the orientation shown, is configured to bias second piston 112 in the distal direction D1 to establish a vacuum at second vacuum port 110-4.

Manifold 94 has a first vacuum draw port 94-1, a second vacuum draw port 94-2, and a first vacuum application port 94-3. Manifold 94 has a first one-way valve 94-4 that is coupled in fluid communication with first vacuum draw port 94-1 and a second one-way valve 94-5 that is coupled in fluid communication with second vacuum draw port 94-2. Each of first one-way valve 94-4 and second one-way valve 94-5 is configured to release positive pressure to the atmosphere to facilitate a purge of positive pressure from vacuum pumps 90, 92 during the charging of sampling spring 182, and to close upon establishment of a vacuum by vacuum pumps 90, 92. In the present embodiment, each of first one-way valve 94-4 and second one-way valve 94-5 is a duckbill valve.

Control valve 96 has a third vacuum draw port 96-1, a second vacuum application port 96-2, and a button actuator 96-3. Button actuator 96-3 selectively controls fluid communication between third vacuum draw port 96-1 and second vacuum application port 96-2. Referring also to FIGS. 5, 7A and 7B, control valve 96 is operated by actuation of cannula retract button 40-2 of actuator mechanism 18, which in turn actuates button actuator 96-3 of control valve 96 to apply the vacuum at side sample port 20-3 of stylet 20 simultaneously with movement of cannula 22 in the proximal direction D2 relative to stylet 20 to ready biopsy device 10 for taking a tissue sample.

First vacuum port 100-4 of vacuum pump 90 is coupled in fluid communication with first vacuum draw port 94-1 of manifold 94 via flexible connection conduit 98-1. Second vacuum port 110-4 of vacuum pump 92 is coupled in fluid communication with second vacuum draw port 94-2 of manifold 94 via flexible connection conduit 98-2. Flexible connection conduits 98-1 and 98-2 may be in the form of a rubber tubular sleeve, and in the present embodiment, are integral with manifold 94. First vacuum application port 94-3 of manifold 94 is coupled in fluid communication with third vacuum draw port 96-1 of control valve 96 via flexible connection conduit 98-3. Second vacuum application port 96-2 of control valve 96 is coupled in fluid communication with lumen 20-2 at open first end 20-4 of stylet 20 via flexible connection conduit 98-4. Flexible connection conduits 98-3 and 98-4 may be in the form of rubber tubes, and are secured to carriage latch cover member 62 via conduit mounts 62-3, 62-4.

Referring again to FIGS. 5, 10 and 11, vacuum pump 90 is received and mounted, e.g., by press fit and/or adhesive, in first pump mounting opening 66-2 of stylet mount end wall 66 of stylet mounting slider 54, with a proximal cylinder portion 100-6 having first vacuum port 100-4 configured to extend in the proximal direction D2 from stylet mount end wall 66, and a distal cylinder portion 100-7 having second opening 100-5 configured to extend in the distal direction D1 from stylet mount end wall 66. Likewise, vacuum pump 92 is received and mounted, e.g., by press fit and/or adhesive, in second pump mounting opening 66-3 of stylet mount end wall 66 of stylet mounting slider 54, with a proximal cylinder portion 110-6 having second vacuum port 110-4 configured to extend in the proximal direction D2 from stylet mount end wall 66, and a distal cylinder portion 110-7 having second opening 110-5 configured to extend in the distal direction D1 from stylet mount end wall 66.

Referring to FIGS. 5 and 11, head 104-2 of plunger 104 of vacuum pump 90 and head 114-2 of plunger 114 of vacuum pump 92 are positioned to be engaged by cannula slide 58. During a first retraction of charge handle 16 in proximal direction D2, there is a corresponding movement of cannula slide 58 in the proximal direction D2, which in turn moves the respective piston/plunger combinations 102/104 and 112/114 of vacuum pumps 90, 92 in the proximal direction D2. As such, each of first vacuum spring 106 of vacuum pump 90 and second vacuum spring 116 of vacuum pump 92 is charged (compressed). The compression of first vacuum spring 106 of vacuum pump 90 and second vacuum spring 116 of vacuum pump 92 occurs simultaneously.

The charging of first vacuum spring 106 and second vacuum spring 116 is accompanied by an evacuation, i.e., purging, of air under positive pressure from elongate cylinders 100, 110 of vacuum pumps 90, 92 via one-way valves 94-4, 94-5 as respective piston/plunger combinations 102/104 and 112/114 are moved in the proximal direction D2. Upon a subsequent movement of cannula slide 58 in the distal direction D1, first vacuum spring 106 and second vacuum spring 116 begin to decompress, and thus bias and tend to move piston/plunger combinations 102/104 and 112/114 of vacuum pumps 90, 92 in the distal direction D1. This movement of piston/plunger combinations 102/104 and 112/114 of vacuum pumps 90, 92 in the distal direction D1 establishes a vacuum at first vacuum port 100-4 of vacuum pump 90 and second vacuum port 110-4 of vacuum pump 92, thereby closing via one-way valves 94-4, 94-5 of manifold 94.

Referring to FIGS. 4, 5, 12A and 12B, interposed between carriage slide 60 of prime pierce carriage 52 and cannula slide 58 is sampling slide 56. Referring also to FIG. 8, sampling slide 56 of carriage assembly 50 is configured to be slidably received in the open distal end 60-1 of prime pierce carriage 52.

Figure 12A:
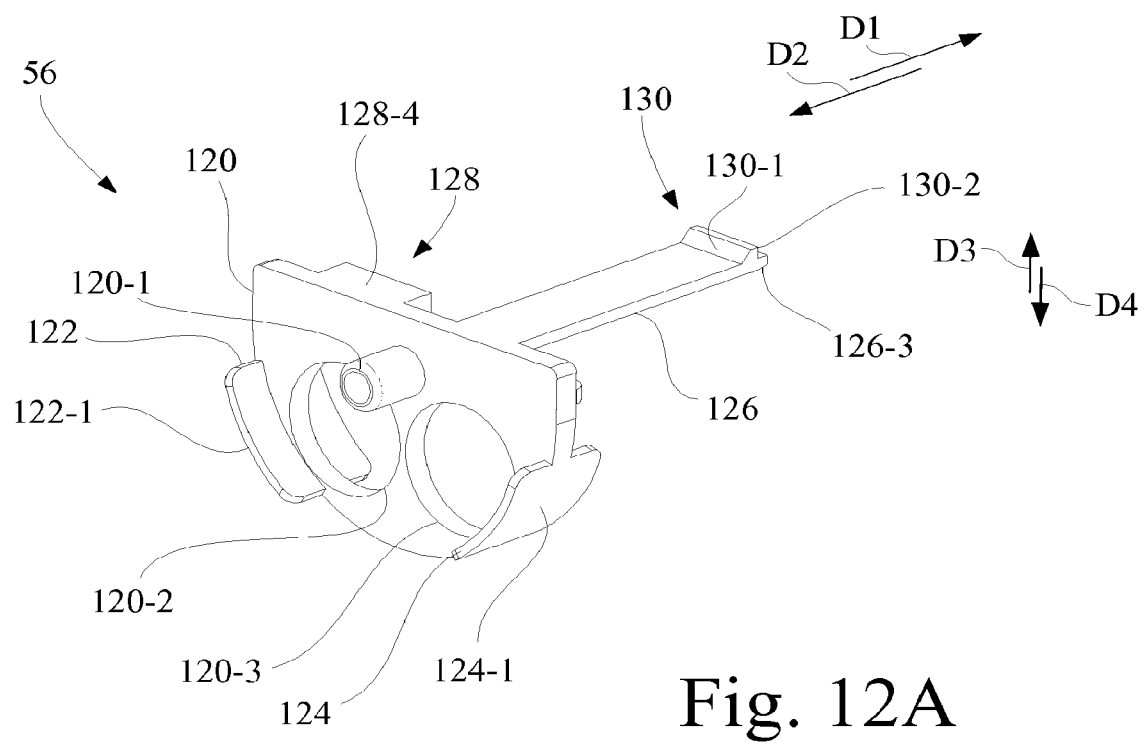
FIG. 12A is a rear perspective view of the sampling slide of the carriage assembly of FIGS. 4, 5, and 10.
Figure 12B:
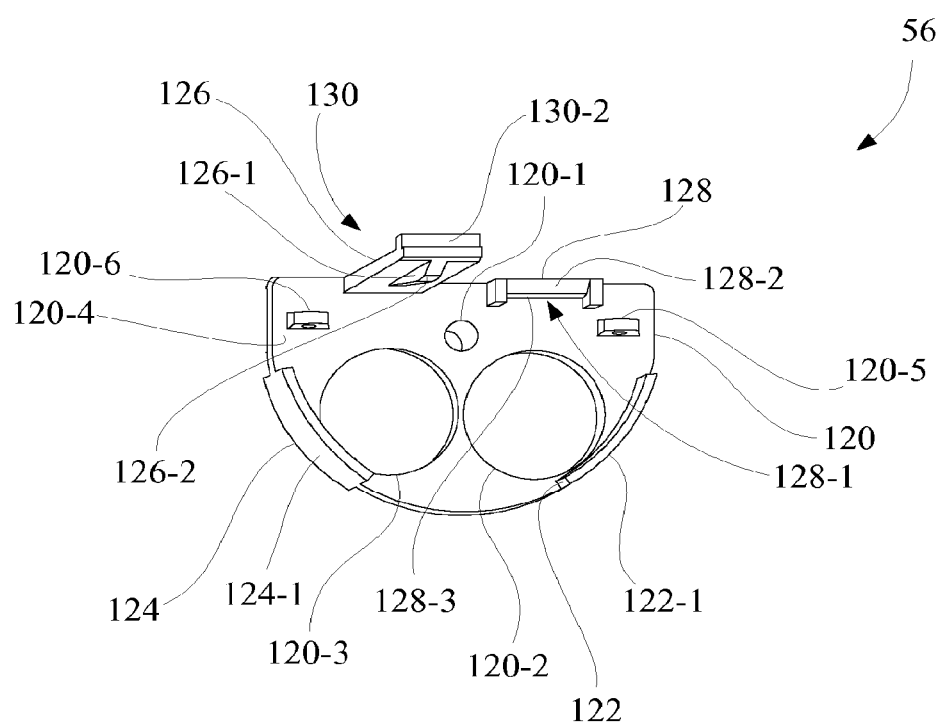
FIG. 12B is a front perspective view of the sampling slide of FIG. 12A.

Referring particularly to FIGS. 12A and 12B, sampling slide 56 has an intermediate slide wall 120, a pair of opposed side walls 122, 124, a latch arm 126, and a latch arm deflection member 128. Intermediate slide wall 120 has a needle hole 120-1, a first pump opening 120-2, a second pump opening 120-3, and a distal face 120-4. A pair of spring attachment loops 120-5, 120-6 extend distally from distal face 120-4.

Needle hole 120-1 is configured to slidably receive stylet 20 of biopsy needle 14, with needle hole 120-1 being sized and shaped to serve as a bearing guide surface against stylet 20. The inside diameter of needle hole 120-1 is slightly larger than the outside diameter of stylet 20 in a tolerance range of 0.01 millimeters (mm) to 1.0 mm.

First pump opening 120-2 is configured to slidably receive vacuum pump 90 in a loose fit, and in particular, first pump opening 120-2 is configured to freely pass elongate cylinder 100, first plunger 104, and first vacuum spring 106 of vacuum pump 90. Second pump opening 120-3 is configured to slidably receive vacuum pump 92 in a loose fit, and in particular, second pump opening 120-3 is configured to freely pass elongate cylinder 110, first plunger 114, and first vacuum spring 116.

The pair of opposed side walls 122, 124 are connected to, or formed integral with, an outer perimeter of intermediate slide wall 120. Side wall 122 extends in both the distal direction D1 and the proximal direction D2 from intermediate slide wall 120, and has a curved cross-section that defines a curved exterior surface 122-1. Likewise, side wall 124 extends in both the distal direction D1 and the proximal direction D2 from intermediate slide wall 120, and has a curved cross-section that defines a curved exterior surface 124-1. The shape of side walls 122, 124, in combination, correspond to the shape of U-shaped interior surface 64-3 of U-shaped wall 64-1 of carriage slide 60 (see also FIG. 8). Thus, the curved exterior surfaces 122-1, 124-1 of the pair of opposed side walls 122, 124 of intermediate slide wall 120 are in sliding contact with U-shaped interior surface 64-3 of U-shaped wall 64-1 of carriage slide 60, which serves as an internal longitudinal guide for sampling slide 56.

Referring again to FIGS. 12A and 12B, latch arm 126 is configured as a cantilever arm that extends in the distal direction D1 from intermediate slide wall 120, with a free end of the cantilever arm having an upwardly facing catch 130. Latch arm 126 is configured to be longitudinally rigid, and vertically resilient in up and down directions D3, D4 that are substantially perpendicular to the longitudinal extent of latch arm 126. Referring to FIG. 12B, latch arm 126 has a downwardly facing longitudinally extending bi-direction ramp 126-1 having a pair of longitudinally opposed ramp surfaces that define a central apex 126-2.

Referring again to FIG. 12A, catch 130 is configured as ramp having an upwardly facing ramp surface 130-1 that diverges in the distal direction D1 to define a distal end face 130-2. An extension portion 126-3 of latch arm 126 extends in distal direction D1 beyond distal end face 130-2 to define a proximally facing L-shaped notch having a floor substantially perpendicular to distal end face 130-2.

Catch 130 of latch arm 126 is configured to releasably engage latch strike 72 of carriage latch cover member 62 (see also FIGS. 8 and 10) so as to couple, and prohibit distal movement of sampling slide 56 with respect to carriage slide 60 of carriage assembly 50, until latch arm 126 is released from latch strike 72 of carriage latch cover member 62 by actuation of sample acquisition button 40-3.

As shown in FIG. 12B, latch arm deflection member 128 defines a retention channel 128-1 having a downwardly facing ramp surface 128-2 and a ceiling 128-3. Ceiling 128-3 extends substantially perpendicularly from intermediate slide wall 120 in distal direction D1. Downwardly facing ramp surface 128-2 diverges in the proximal direction D2 from an upper surface 128-4 of latch arm deflection member 128 to join ceiling 128-3.

Figure 13:
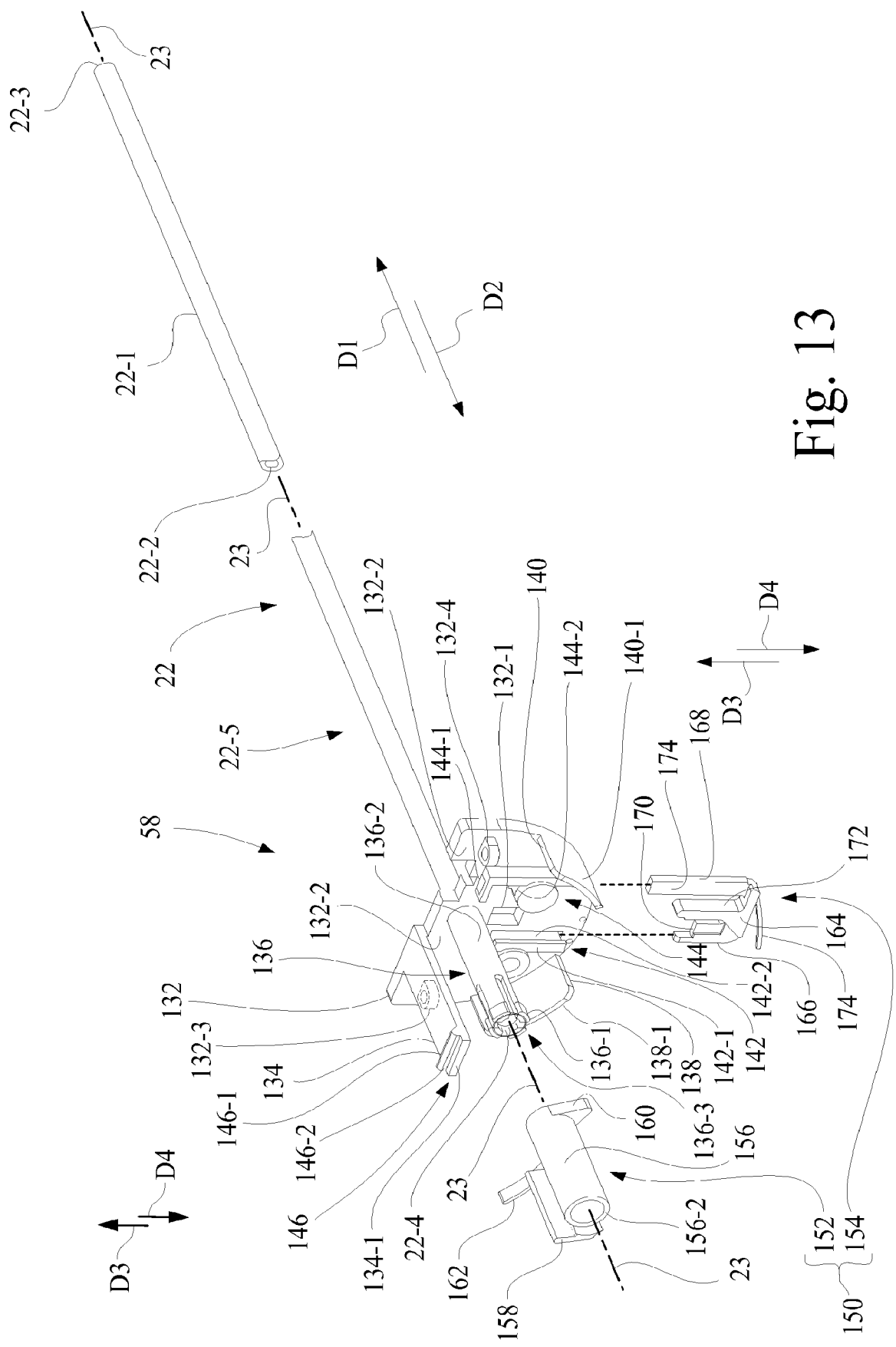
FIG. 13 is a perspective view of the cannula slide and indexing mechanism of the carriage assembly of FIGS. 4, 5, and 10.

Referring FIGS. 5, 8 and 13, cannula slide 58 of carriage assembly 50 also is configured to be slidably received in the open distal end 60-1 of prime pierce carriage 52.

As best shown in FIG. 13, cannula slide 58 has a cannula mount end wall 132 and a latch arm 134 that extends in the proximal direction D2 from cannula mount end wall 132. Referring to FIG. 5, cannula mount end wall 132 is longitudinally spaced distally along longitudinal axis 23 from stylet mount end wall 66 of carriage slide 60. Intermediate slide wall 120 is longitudinally interposed between, and spaced along longitudinal axis 23 from each of, stylet mount end wall 66 and cannula mount end wall 132.

Referring to FIGS. 13 and 16-18, cannula mount end wall 132 includes an indexing window 132-1, a proximal face 132-2, and a pair of spring attachment loops 132-3, 132-4. The pair of spring attachment loops 132-3, 132-4 extend proximally from proximal face 132-2.

Extending in proximal direction D2 from cannula mount end wall 132 is a longitudinally extending cannula mount tube 136 having a flared proximal end 136-1, an annular bearing surface 136-2, and a tubular aperture 136-3. Cannula 22 is fixedly mounted in cannula mount tube 136 of cannula mount end wall 132, e.g., by press fit and/or adhesive.

As shown in the breakaway portion of FIG. 13, cannula 22 has a side wall 22-1 configured to define a lumen 22-2, and has a distal cutting edge 22-3. A proximal portion 22-4 of cannula 22 extends in proximal direction D2 from cannula mount end wall 132 and a distal portion 22-5 of cannula 22 extends in a distal direction D1 from cannula mount end wall 132. Distal portion 22-5 of cannula 22 is slidably received through needle opening 12-1 of housing 12 (see FIG. 1).

Cannula mount end wall 132 further includes a pair of opposed side walls 138, 140, having a curved cross-section, and each having a respective curved exterior surface 138-1, 140-1 that corresponds to the shape of U-shaped interior surface 64-3 of U-shaped wall 64-1 of carriage slide 60 (see also FIGS. 5 and 8). The pair of opposed side walls 138, 140 of cannula mount end wall 132 is in sliding contact with U-shaped interior surface 64-3 of U-shaped wall 64-1 of carriage slide 60, which serves as a longitudinal guide for cannula slide 58 within prime pierce carriage 52.

Referring again to FIGS. 13 and 16-18, positioned centrally under cannula mount tube 136 is indexing window 132-1, which is formed as a rectangular opening that extends through cannula mount end wall 132. Indexing window 132-1 is laterally interposed between two vertically oriented guide channels identified as guide channel 142 and guide channel 144. Guide channels 142, 144 are vertically oriented to be parallel to proximal face 132-2 of cannula mount end wall 132. In the present embodiment, guide channel 142 is defined by a vertical structure 142-1 having a side slot 142-2, and guide channel 144 is defined by upper guide opening 144-1 and a lower guide opening 144-2.

Indexing window 132-1 is sized to freely receive charge handle latch arm 38 (see FIG. 6) without inducing a latching engagement. However, indexing window 132-1 may be selectively intersected, in part, by a portion of an indexing mechanism 150, as described in more detail below, such that the portion of indexing mechanism 150 intersecting indexing window 132-1 may be engaged by catch 38-2 of charge handle latch arm 38 of charge handle 16 on a return stroke of charge handle 16 in distal direction D1.

As shown in FIG. 13, latch arm 134 is configured as a cantilever arm that extends in the proximal direction D2 from cannula mount end wall 132, with a free end of the cantilever arm having an upwardly facing catch 146. Latch arm 134 is configured to be longitudinally rigid, and vertically resilient in up and down directions D3, D4 that are substantially perpendicular to the longitudinal extent of latch arm 134. Catch 146 is configured as ramp having an upwardly facing ramp surface 146-1 that diverges in the proximal direction D2 to define a proximal end face 146-2. In the present embodiment, an extension portion 134-1 of latch arm 134 extends in proximal direction D2 beyond proximal end face 146-2 to define a proximally facing L-shaped notch having a floor substantially perpendicular to proximal end face 146-2.

Catch 146 of latch arm 134 of cannula slide 58 is configured to selectively and releasably engage latch strike 70 of carriage latch cover member 62, and when so engaged, couples cannula slide 58 to carriage slide 60 to prohibit proximal movement of cannula slide 58 with respect to carriage slide 60 of carriage assembly 50, until latch arm 134 is released from latch strike 70 by actuation of cannula retract button 40-2 (see FIG. 1).

Referring to FIGS. 13-18, indexing mechanism 150 includes a cannula slide indexer 152 and a sampling slide indexer 154 which cooperate to coordinate the various stages of operation of biopsy device 10. Cannula slide indexer 152 is configured to pivot about cannula mount tube 136 of cannula slide 58, and sampling slide indexer 154 is configured to move linearly in directions D3 and D4, e.g., up and down, as guided by guide channels 142, 144 of cannula slide 58. Here directions D3 and D4 are opposite directions, e.g., up and down, and directions D3 and D4 are substantially perpendicular to longitudinal axis 23.

Figure 14A:
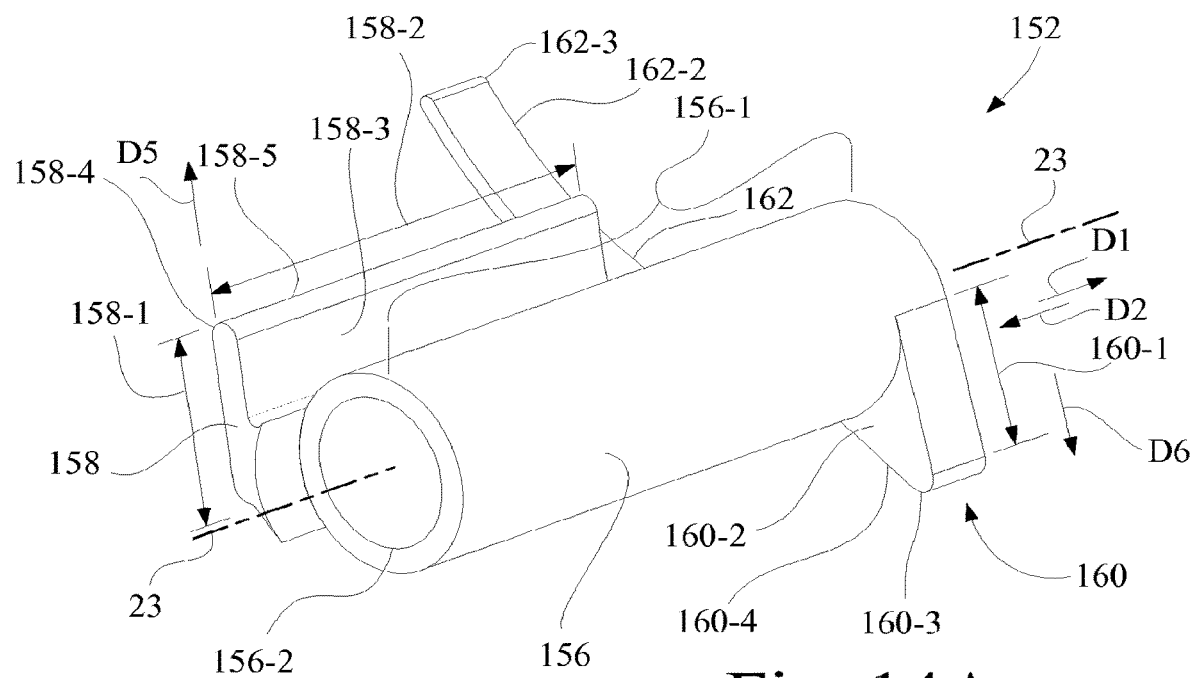
FIG. 14A is an enlarged perspective view of the cannula slide indexer of the indexing mechanism depicted in FIGS. 5 and 13.
Figure 14B:
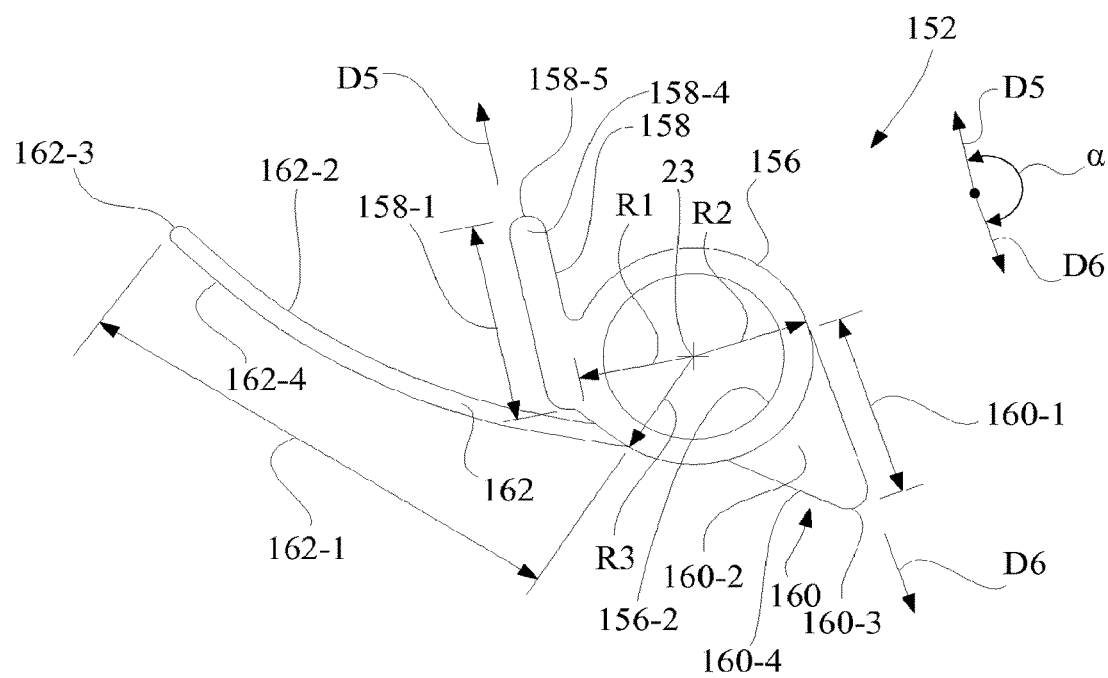
FIG. 14B is an end view of the cannula slide indexer of FIG. 14A.
Figure 15A:
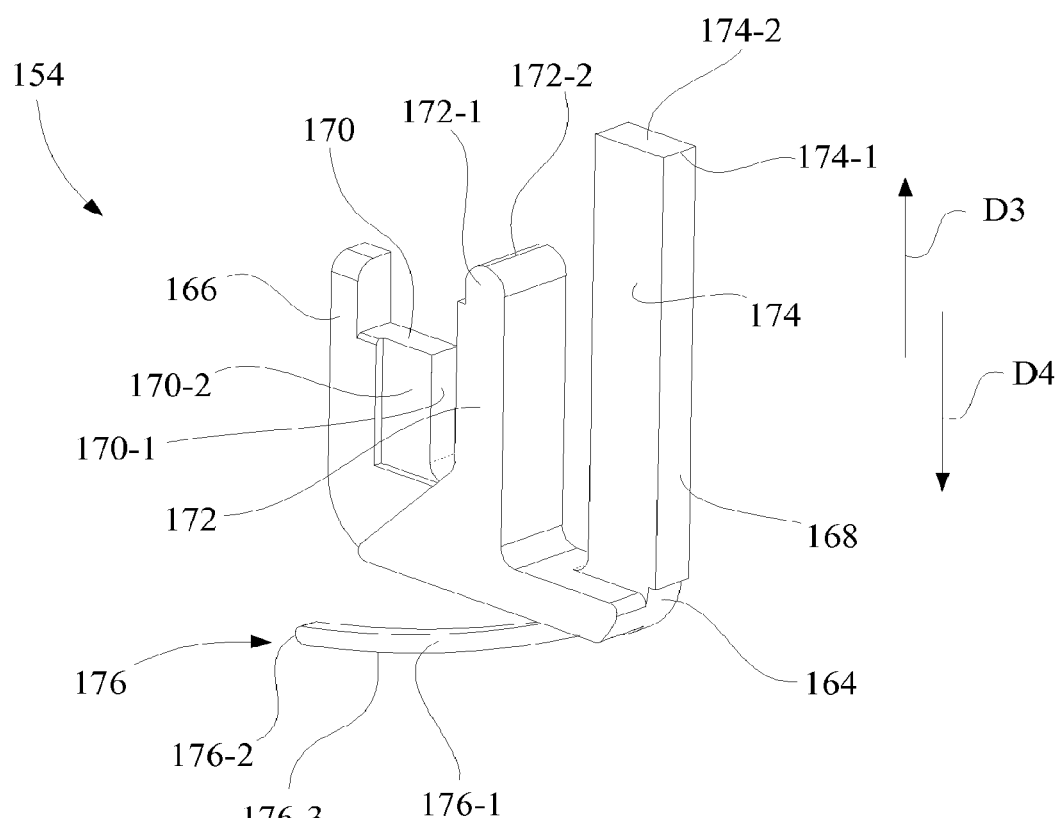
FIG. 15A is an enlarged perspective view of the sampling slide indexer of the indexing mechanism depicted in FIGS. 5 and 13.
Figure 15B:
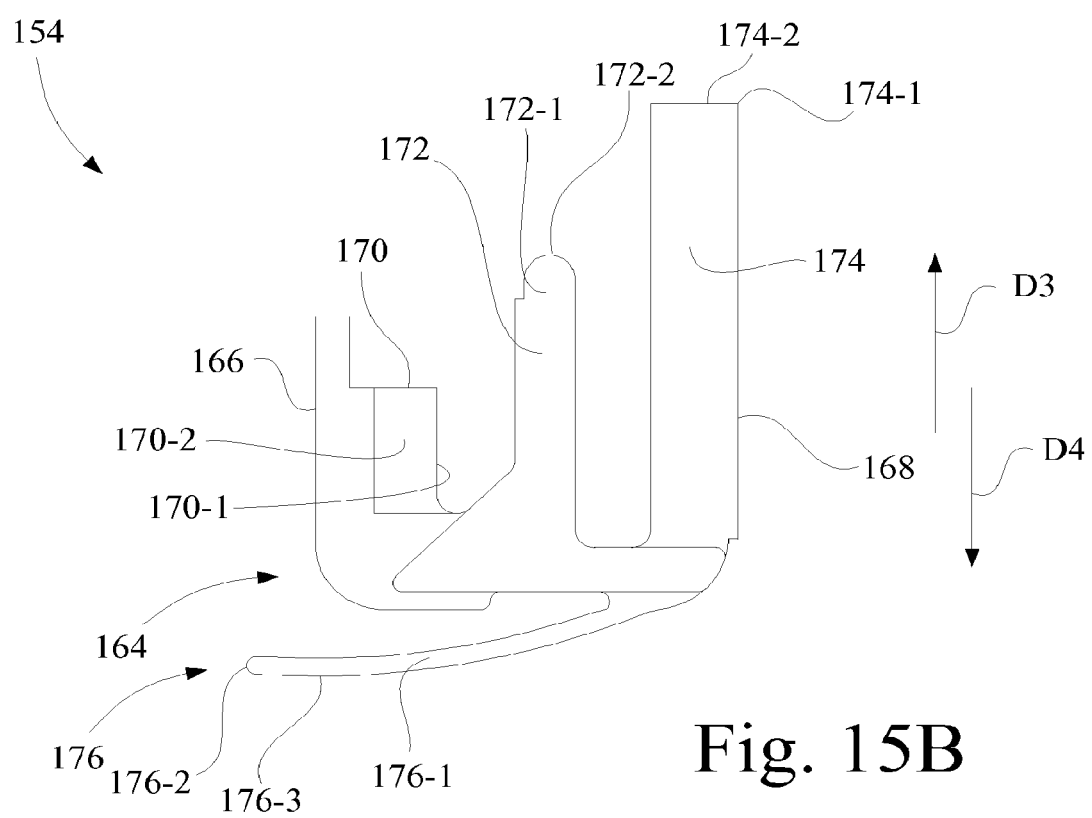
FIG. 15B is a rear (proximal) view of the sampling slide indexer of FIG. 15A.

Referring to FIG. 13, cannula slide indexer 152 is selectively operated by a deflection of latch arm 134 of cannula slide 58. Referring also to FIGS. 14A, 14B, in the embodiment shown, cannula slide indexer 152 is configured as an integral structure that includes an axel 156, a lever arm 158, an actuator arm 160, and a torsion spring 162.

Axel 156 of cannula slide indexer 152 has a longitudinal extent 156-1 and a cylindrical opening 156-2 configured to be received over bearing surface 136-2 of cannula mount tube 136. The inside diameter of cylindrical opening 156-2 is slightly larger than the outside diameter of bearing surface 136-2 in a tolerance range of 0.01 millimeters (mm) to 1.0 mm so as to permit a pivoting (rotational) motion of cannula slide indexer 152 about cannula mount tube 136, and in turn, to permit pivoting motion about longitudinal axis 23. Axel 156 is retained on bearing surface 136-2 of cannula mount tube 136 by flared proximal end 136-1.

Figure 16:
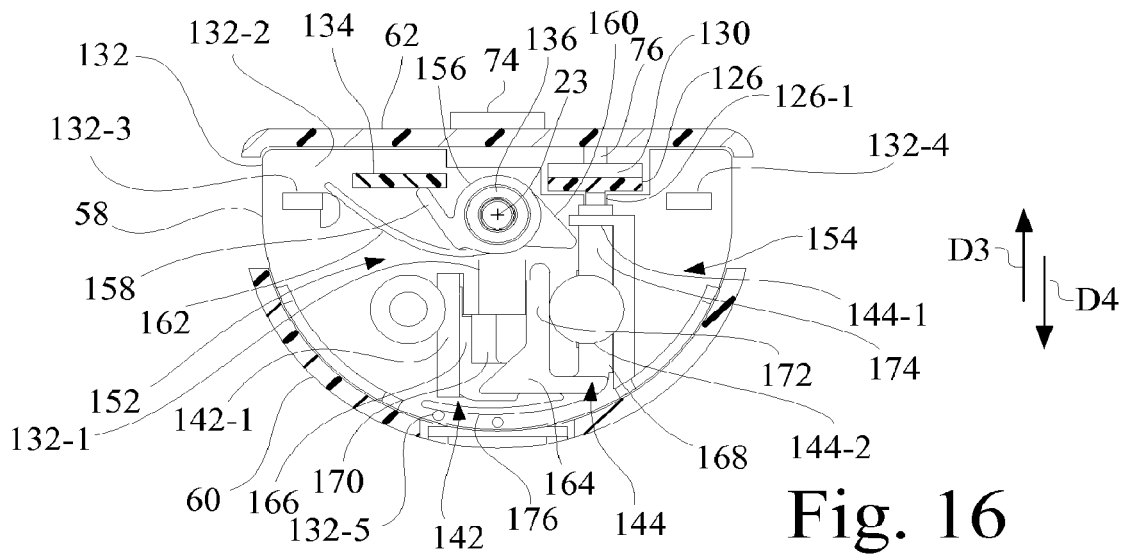
FIG. 16 shows the relative positions of the cannula slide indexer and the sampling slide indexer of the indexing mechanism depicted in FIGS. 5, 13, and 14A-15B, when the biopsy device is new from the manufacturer, as well as at the conclusion of a biopsy procedure.
Figure 17:
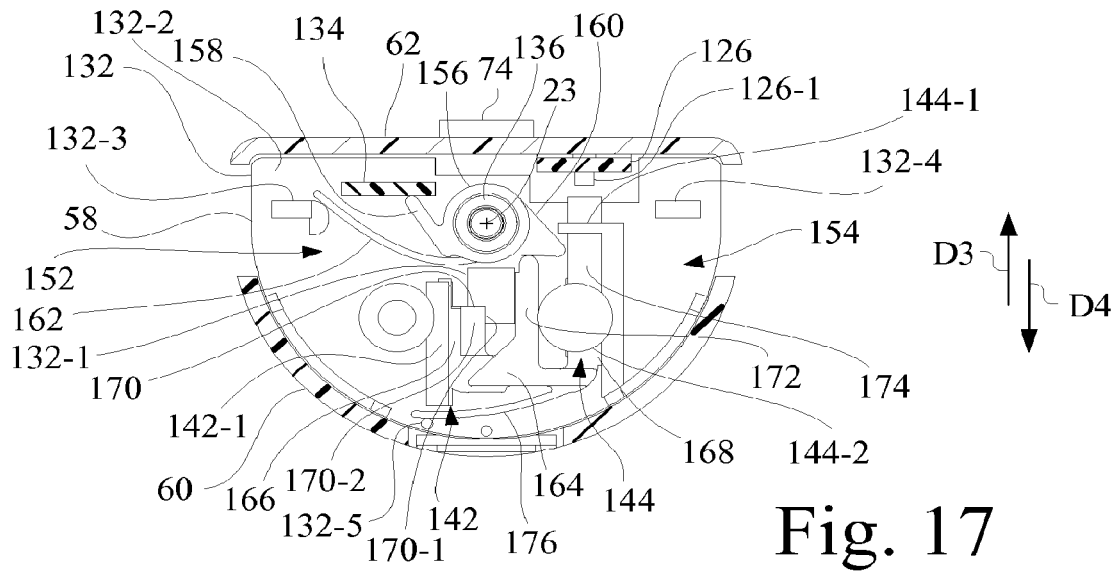
FIG. 17 shows the relative positions of the cannula slide indexer and the sampling slide indexer of the indexing mechanism depicted in FIGS. 5, 13, and 14A-15B, following a first retraction (proximal) stroke of the charge handle of the biopsy device of FIG. 1, wherein the sampling spring and vacuum springs are charged, and prior to and during a second retraction (proximal) stroke and second return (distal) stroke of the charge handle.
Figure 18:
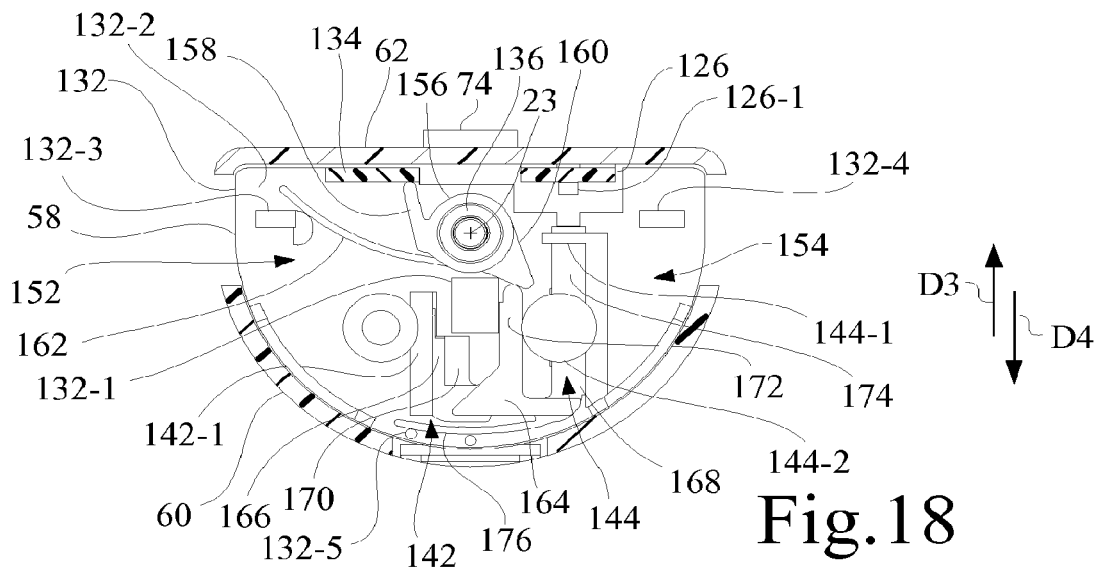
FIG. 18 shows the relative positions of the cannula slide indexer and the sampling slide indexer of the indexing mechanism depicted in FIGS. 5, 13, and 14A-15B, after the second return (distal) stroke of the charge handle of the biopsy device of FIG. 1, wherein the cannula retract springs are charged, and prior to a third retraction (proximal) stroke of the charge handle to charge the prime pierce spring.

Lever arm 158 is radially offset from cylindrical opening 156-2 and in turn is radially offset from longitudinal axis 23 by a radial distance R1. Referring also to FIGS. 16-18, lever arm 158 is positioned and oriented to be selectively engaged by latch arm 134 of cannula slide 58. As best shown in FIGS. 14A and 14B, lever arm 158 has a tangential extent 158-1 and a longitudinal extent 158-2. Tangential extent 158-1 of lever arm 158 is oriented to tangentially extend in a cantilever manner in a direction D5 from axel 156 along a tangent of an imaginary circle corresponding to radial distance R1. Since cannula slide indexer 152 pivots about longitudinal axis 23, direction D5 is relative and the actual direction is dependent upon the angular rotational position of cannula slide indexer 152. Lever arm 158 is configured to be rigid, and may be defined as a plate 158-3 having tangential extent 158-1 and longitudinal extent 158-2, and having a free end 158-4 that defines a longitudinal engagement surface 158-5 having a radius. Longitudinal engagement surface 158-5 is positioned and oriented to be selectively engaged by a bottom surface of latch arm 134 of cannula slide 58 (see also FIGS. 13, and 16-18).

Actuator arm 160 is radially offset from cylindrical opening 156-2 and in turn is radially offset from longitudinal axis 23 by a radial distance R2. Actuator arm 160 has a tangential extent 160-1. Tangential extent 160-1 of actuator arm 160 is oriented to tangentially extend in a cantilever manner in a direction D6 from axel 156 along a tangent of an imaginary circle corresponding to radial distance R2. Since cannula slide indexer 152 pivots about longitudinal axis 23, direction D6 is relative and the actual direction is dependent upon the angular rotational position of cannula slide indexer 152. However, direction D6 is in a fixed relationship to direction D5, which are in substantially opposite directions, wherein the term "substantially opposite" means a range of linear (180 degrees) plus or minus 15 degrees. In the present embodiment, the angular range a of the fixed relationship of direction D5 relative to direction D6 with respect to longitudinal axis 23 may be in a range of 165 degrees to 180 degrees (linear). Actuator arm 160 is configured to be rigid, and may be defined as a triangular plate 160-2 having tangential extent 160-1, and having a free end 160-3 and a planar engagement surface 160-4.

Torsion spring 162 is radially offset from cylindrical opening 156-2 and in turn is radially offset from longitudinal axis 23 by a radial distance R3. Torsion spring 162 has an outward extent 162-1. Outward extent 162-1 of actuator arm 160 is oriented to extend in a cantilever manner from axel 156. In the orientation of components shown in FIGS. 5 and 13-14B, torsion spring 162 is configured to bias cannula slide indexer 152 to pivot in a clockwise direction about longitudinal axis 23. In particular, torsion spring 162 is configured to be resilient, and may be defined as curved cantilever arm 162-2 having a free end 162-3, wherein a contact surface 162-4 of cantilever arm 162-2 engages a fixed feature of cannula slide indexer 152, such as spring attachment loop 132-3 (see FIGS. 16-18), where cantilever arm 162-2 applies a counterclockwise force to spring attachment loop 132-3 to bias cannula slide indexer 152 to pivot in the clockwise direction.

Referring to FIGS. 13 and 15A-18, sampling slide indexer 154 is configured generally as an integral plate-like planar structure, and includes a base 164, a left slide 166, a right slide 168, a window blocking plate 170, a first cam arm 172, a second cam arm 174, and a cantilever spring 176. Left slide 166, right slide 168, window blocking plate 170, first cam arm 172, and second cam arm 174 extend vertically in direction D3 from base 164. Cantilever spring 176 is located below, in direction D4, from base 164.

Referring also to FIGS. 16-18, left slide 166 is sized and shaped to be slidably received in side slot 142-2 of guide channel 142 of cannula mount end wall 132 of cannula slide 58. Right slide 168 is sized and shaped to be slidably received in upper guide opening 144-1 and lower guide opening 144-2 of guide channel 144 of cannula mount end wall 132 of cannula slide 58.

Window blocking plate 170 may be formed integral with left slide 166. Window blocking plate 170 is configured as a vertically extending plate positioned and oriented to selectively intersect, and partially cover, indexing window 132-1 of cannula mount end wall 132 of cannula slide 58. Window blocking plate 170 includes a side surface 170-1 and a proximal surface 170-2.

First cam arm 172 is configured to vertically extend from base 164. First cam arm 172 is laterally interposed between, and spaced from, window blocking plate 170 and second cam arm 174. First cam arm 172 is positioned and oriented to be selectively engaged by engagement surface 160-4 of actuator arm 160 of cannula slide indexer 152. In particular, first cam arm 172 has a free end 172-1 having a radial engagement surface 172-2 that may be engaged by the planar engagement surface 160-4 of actuator arm 160 of cannula slide indexer 152.

Second cam arm 174 may be formed integral with right slide 168. Second cam arm 174 is configured to vertically extend from base 164. Second cam arm 174 is positioned and oriented to be selectively engaged by bi-direction ramp 126-1 of latch arm 126 of sampling slide 56. In particular, second cam arm 174 has a free end 174-1 having an engagement surface 174-2 that may be engaged by bi-direction ramp 126-1 of latch arm 126 of sampling slide 56.

Cantilever spring 176 is configured as a curved cantilever that extends below a lower portion of base 164, and in turn is located below, base 164, in direction D4. In the orientation of components shown in FIGS. 5, 13 and 15A-18, cantilever spring 176 is configured to bias sampling slide indexer 154 in direction D3 (in an upward direction). In particular, cantilever spring 176 is configured to be resilient, and is defined as curved cantilever arm 176-1 having a free end 176-2, wherein a contact surface 176-3 of cantilever arm 176-1 engages a fixed feature of cannula slide indexer 152, such as longitudinally extending pin 132-5 of cannula slide 58 (see FIGS. 16-18), where cantilever arm 176-1 applies a downward force in direction D4 to pin 132-5 to bias sampling slide indexer 154 upwardly in direction D3.

Referring again to FIG. 5, the motive force provided to power the various functions of biopsy device 10 is provided by at least one cannula retract spring (the present embodiment having a pair of cannula retract springs 180-1, 180-2), a sampling spring 182, and a prime pierce spring 184. Those skilled in the art will recognize that the effect of each of cannula retract springs 180-1, 180-2, sampling spring 182, and prime pierce spring 184 may be accomplished by a single spring, or by a plurality of springs.

Figure 19:
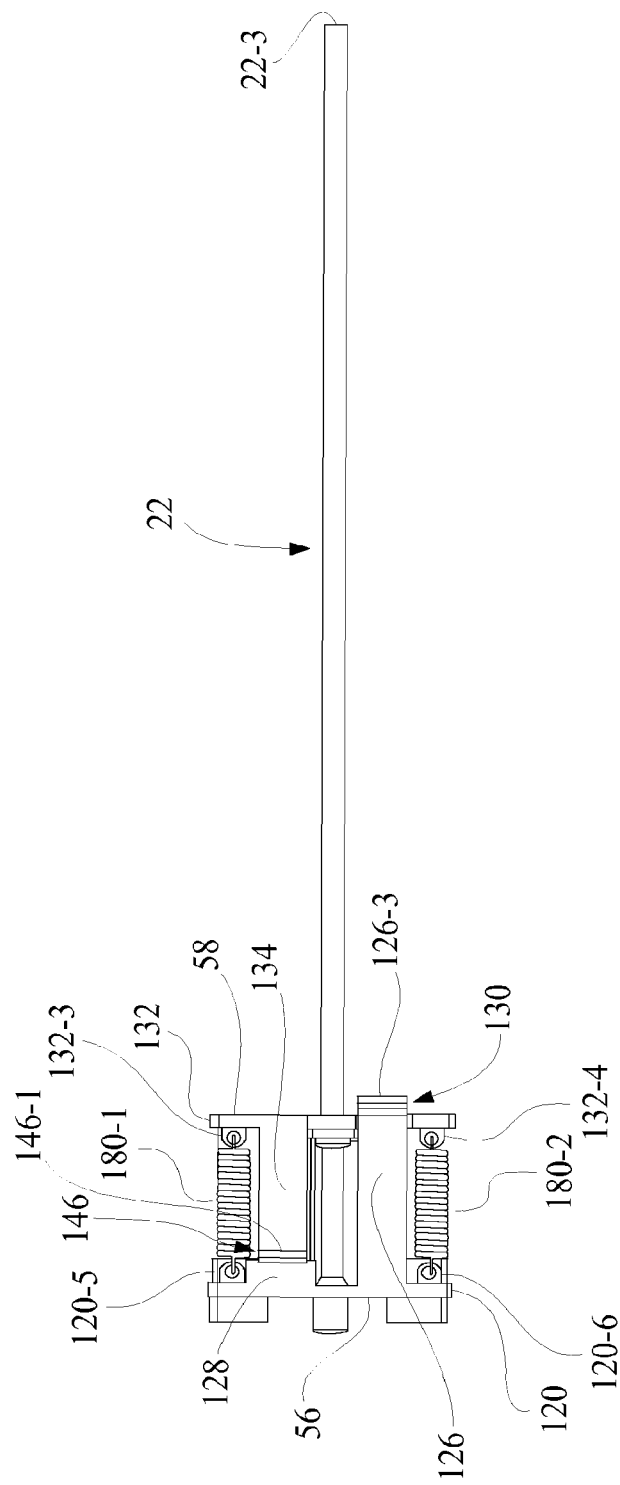
FIG. 19 is a top view of a subassembly formed by the sampling slide and cannula slide depicted in FIGS. 5, 12A and 13, prior to insertion of the subassembly into prime pierce carriage of FIG. 8.

Referring to FIG. 19, sampling slide 56 and cannula slide 58 are assembled as a subassembly prior to insertion into prime pierce carriage 52 over stylet 20 (see FIG. 8). In particular, cannula retract spring 180 (two shown in the present embodiment, as 180-1, 180-2), is interposed between, and connected to each of, intermediate slide wall 120 of sampling slide 56 and cannula mount end wall 132 of cannula slide 58. In particular, cannula retract spring 180-1, is attached at its ends to spring attachment loop 120-5 of intermediate slide wall 120 of sampling slide 56 and spring attachment loop 132-3 of cannula mount end wall 132 of cannula slide 58. Likewise, cannula retract spring 180-2, is attached at its ends to spring attachment loop 120-6 of intermediate slide wall 120 of sampling slide 56 and spring attachment loop 132-4 of cannula mount end wall 132 of cannula slide 58.

As shown in FIG. 19, latch arm deflection member 128 of sampling slide is configured for engagement with latch arm 134 of cannula slide 58, and when so engaged, latch arm deflection member 128 deflects, i.e., flexes, latch arm 134 downwardly toward carriage base 64. More particularly, referring also to FIGS. 12B and 13, extension portion 134-1 at the free end of latch arm 134 is positioned for engagement with intermediate slide wall 120 in retention channel 128-1 of intermediate slide wall 120 of sampling slide 56, such that when so engaged, a longitudinal movement of cannula slide 58 in the proximal direction D2 results in a corresponding longitudinal movement of sampling slide 56 in the proximal direction D2.

In turn, as shown in FIG. 17, a bottom surface of latch arm 134 of cannula slide 58 engages lever arm 158 to rotate cannula slide indexer 152 counterclockwise about longitudinal axis 23, thus lifting actuator arm 160 and permitting sampling slide indexer 154 to move upward in direction D3 by action of cantilever spring 176, thereby positioning window blocking plate 170 to block a portion, e.g., the lower left quadrant, of indexing window 132-1 of cannula slide 58, such that window blocking plate 170 may be engaged by catch 38-2 of charge handle latch arm 38 of charge handle 16 (see also FIG. 6).

When cannula slide 58 is moved in distal direction D1 away from sampling slide 56, latch arm 134 disengages from latch arm deflection member 128 and, due to its resiliency, latch arm 134 returns to its non-deflected position, i.e., latch arm 134 moves back to its original non-flexed position. In turn, as shown in FIG. 18, cannula slide indexer 152 rotates counterclockwise about longitudinal axis 23 to its full clockwise position via the torsional force exerted by torsion spring 162, thus moving sampling slide indexer 154 downwardly in direction D4, such that window blocking plate 170 no longer blocks a portion of indexing window 132-1 of cannula slide 58.

As shown in FIG. 19, sampling slide 56 is spaced a minimum allowable distance from cannula slide 58 and places each of cannula retract springs 180-1, 180-2 in a contracted state, but each of cannula retract springs 180-1, 180-2 may be in a slight state of extension. The term "slight state of extension" means the storage of a force that is less than 10 percent of the total force available from springs 180-1, 180-2 in a charged (extended) state. As used herein, the term "charge" or "charged" means the storage of mechanical energy by one or more springs. The term "charging" means the act of storing mechanical energy in a storage device in the form of one or more springs. Thus, cannula retract springs 180-1, 180-2 are charged to a charged state to store mechanical energy when cannula retract springs 180 are in an extended state.

Referring also to FIG. 5, cannula retract springs 180-1, 180-2 are releasably held in the charged (extended) state under the condition: (a) catch 130 of latch arm 126 of sampling slide 56 is engaged with latch strike 72 of carriage latch cover member 62 and (b) catch 146 of latch arm 134 of cannula slide 58 is engaged with latch strike 70 of carriage latch cover member 62. When catch 146 of latch arm 134 is released from latch strike 70, cannula retract springs 180 are released from the charged (extended) state and exert a contraction force to bias and move cannula mount end wall 132 of cannula slide 58, and in turn cannula 22, in the proximal direction D2 toward sampling slide 56, which in turn exposes side sample port 20-3 of stylet 20.

Referring again to FIG. 5, sampling spring 182 is interposed between stylet mount end wall 66 of carriage slide 60 of prime pierce carriage 52 and intermediate slide wall 120 of sampling slide 56. In the present embodiment, sampling spring 182 is a coil spring that is charged, via a compression of sampling spring 182, to store mechanical energy when held in a charged (compressed) state. Sampling spring 182 is held, i.e., retained, in the charged (compressed) state, when catch 130 of latch arm 126 of sampling slide 56 is engaged with latch strike 72 of carriage latch cover member 62. When released from the charged (compressed) state, sampling spring 182 exerts an expansion force to bias and move sampling slide 56, and in turn cannula slide 58 and cannula 22, in distal direction D1.

Referring to FIGS. 4 and 5, prime pierce spring 184 is interposed between intermediate wall 32 of housing 12 and prime pierce mount post 64-9 of carriage base 64 of carriage slide 60 of prime pierce carriage 52. Prime pierce spring 184 is charged to a charged state to store mechanical energy when prime pierce spring 184 is in a compressed state.

Prime pierce spring 184 is releasably held in the charged (compressed) state when carriage latch arm 74 of carriage latch cover member 62 is engaged with carriage latch strike 44 of actuator mechanism 18 (see also FIG. 7B). At this stage, biopsy device 10 is described as being primed.

When prime pierce spring 184 is released from the charged (compressed) state, which enters a "pierce" condition, prime pierce spring 184 exerts an expansion force to fire, i.e., to rapidly move, carriage assembly 50 carrying biopsy needle 14, as a whole, in the distal direction D1. In other words, the firing of carriage assembly 50 carrying biopsy needle 14 simultaneously moves stylet 20 and cannula 22 in distal direction D1 such that biopsy needle 14 punctures the tissue of a patient at the desired location.

Referring again to FIG. 5, charge handle 16 and indexing mechanism 150 in combination form a cocking mechanism, as more fully described below.

Referring also to FIGS. 1 and 20-26, a user grasps charge handle 16 and manually effects a proximal stroke, i.e., a retraction, of charge handle 16 relative to housing 12 by pulling charge handle 16 in the proximal direction D2 from the home position to the retracted position, which in turn charges (extends) biasing springs 39-1, 39-2. While a plurality of biasing springs are shown in the present embodiment, those skilled in the art will recognize that the effect of biasing springs 39-1, 39-2 may be accomplished by a single spring or by multiple springs. The user releases charge handle 16, and biasing springs 39-1, 39-2 contract to effect movement of charge handle 16 relative to housing 12 in a return (distal) stroke in the distal direction D1 to return charge handle 16 to the home position.

FIGS. 20-26 shows biopsy 10 with the upper case portion 24 removed to expose carriage assembly 50, and with carriage latch cover member 62 disconnected from carriage slide 60 of prime pierce carriage 52 to expose sampling slide 56 and cannula slide 58, so as to show the various positional relationships of components during various stages of preparing biopsy device 10 for use in taking a biopsy sample from a patient.

Figure 20:
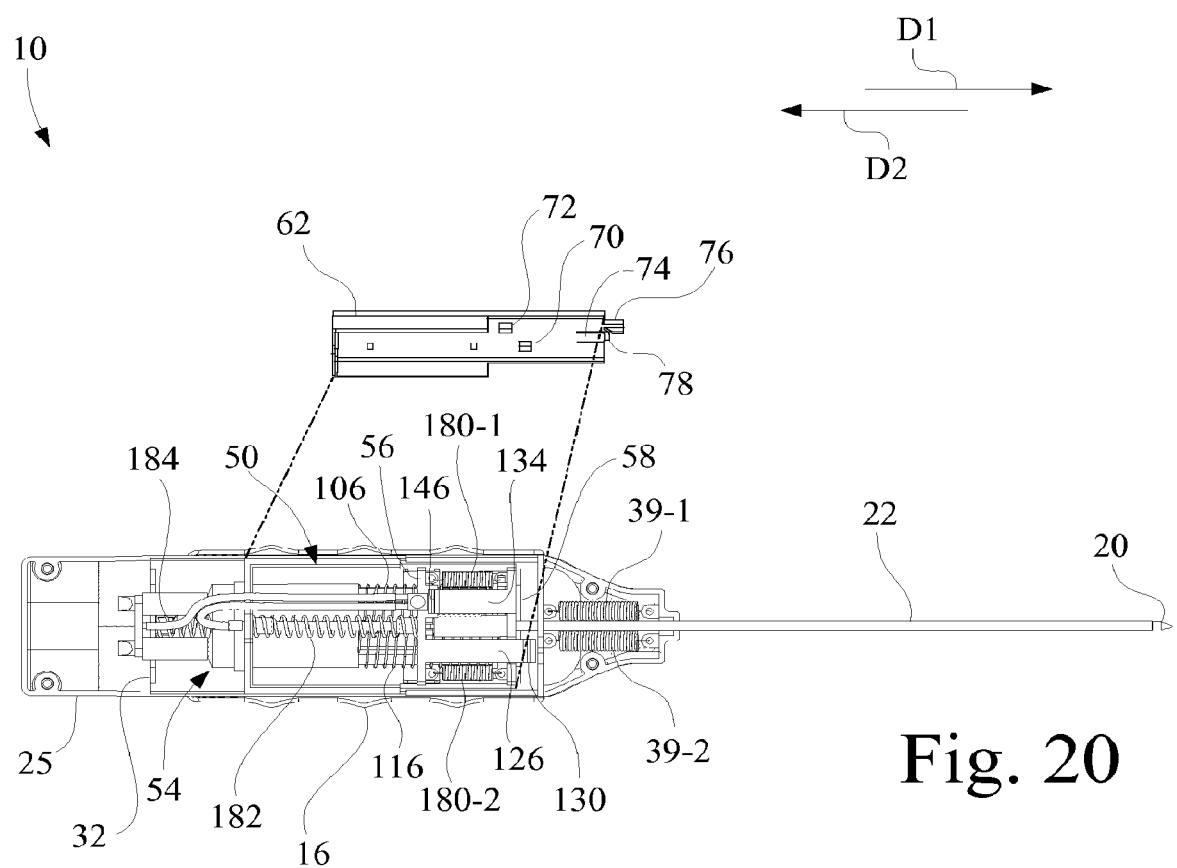
FIG. 20 shows a top view of the biopsy device of FIG. 1 with the upper case portion removed, and with the carriage latch cover member separated from the carriage slide, so as to expose the positions of the sampling slide, the cannula slide, and the vacuum system of the carriage assembly, when the biopsy device is new with the charge handle in the home position, or after the biopsy device has been fully cycled in taking a biopsy tissue sample.

FIG. 20 shows biopsy device 10 when biopsy device 10 is new, and after biopsy device has been fully cycled in taking a biopsy. As shown, all of the biasing springs 39-1, 39-2, vacuum springs 106, 116, cannula retract springs 180-1, 180-2, sampling spring 182, and prime pierce spring 184 are in a discharged state.

Figure 21:
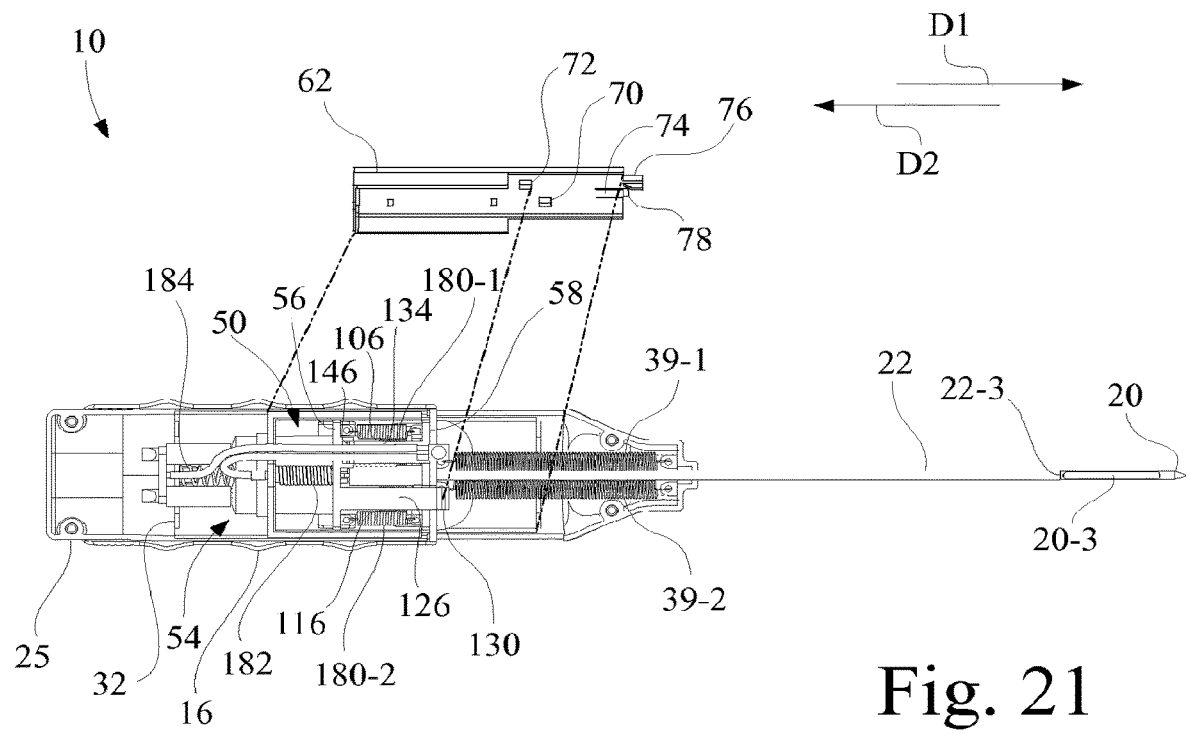
FIG. 21 shows the biopsy device depicted in FIG. 20, with the charge handle in the retracted position, and wherein with a first retraction (proximal) stroke of the charge handle, the sampling slide and the cannula slide are moved collectively in the proximal direction relative to carriage slide of the prime pierce carriage to simultaneously charge the vacuum springs of the vacuum system and the sampling spring.

Referring to FIG. 21, on a first retraction (proximal) stroke of charge handle 16 in proximal direction D2, sampling slide 56 and cannula slide 58 are moved collectively in the proximal direction D2 relative to carriage slide 60 to simultaneously charge vacuum springs 106, 116 and sampling spring 182. In particular, at the onset of the first retraction (proximal) stroke of charging handle 16, cannula slide indexer 152 and sampling slide indexer 154 of indexing mechanism 150 are positioned as shown in FIG. 16, such that charge handle latch arm 38 of charge handle 16 is free to pass through indexing window 132-1 of cannula slide 58, and charge handle end wall 36 of charge handle 16 engages cannula mount end wall 132 of cannula slide 58. With latch arm 134 of cannula slide 58 engaged with, i.e., abutting, intermediate slide wall 120 of sampling slide 56 and with latch arm 134 of cannula slide 58 being deflected downwardly by latch arm deflection member 128 of sampling slide 56, sampling slide 56 and cannula slide 58 are moved collectively in the proximal direction D2 by the proximal movement of charge handle 16.

Thus, the first retraction (proximal) stroke of the charge handle 16 toward to the retracted position moves the sampling slide 56 and the cannula mount end wall 132 of cannula slide 58 that carries the cannula 22 in unison, by virtue of the latch arm 134 being engaged with the intermediate slide wall 120 of sampling slide 56, in the proximal direction D2 to charge (compress) sampling spring 182. Simultaneously, the proximal movement of cannula mount end wall 132 of cannula slide 58 moves the respective piston/plunger combinations 102/104 and 112/114 of vacuum pumps 90, 92 in the proximal direction D2 to charge (compress) first vacuum spring 106 of vacuum pump 90 and second vacuum spring 116 of vacuum pump 92.

When charge handle 16 is in the retracted position at the end of the first proximal stroke, catch 130 of latch arm 126 of sampling slide 56 pivots upwardly to engage latch strike 72 of carriage latch cover member 62 to retain sampling spring 182 in the charged (compressed) state. However, even though the upward pivoting latch arm 126 releases sampling slide indexer 154 for movement upward in direction D3, since charge handle latch arm 38 of charge handle 16 is inserted into indexing window 132-1 of cannula slide 58, charge handle latch arm 38 prevents sampling slide indexer 154 from extending vertically over a portion of indexing window 132-1.

At this time as well, vacuum springs 106, 116 are retained in their charged state only by the internally generated vacuum in vacuum pumps 90, 92. As the vacuum is released, e.g., by operation of button 40-2 of actuator mechanism 18, then vacuum springs 106, 116 will tend to return to their non-charged state.

Figure 22:
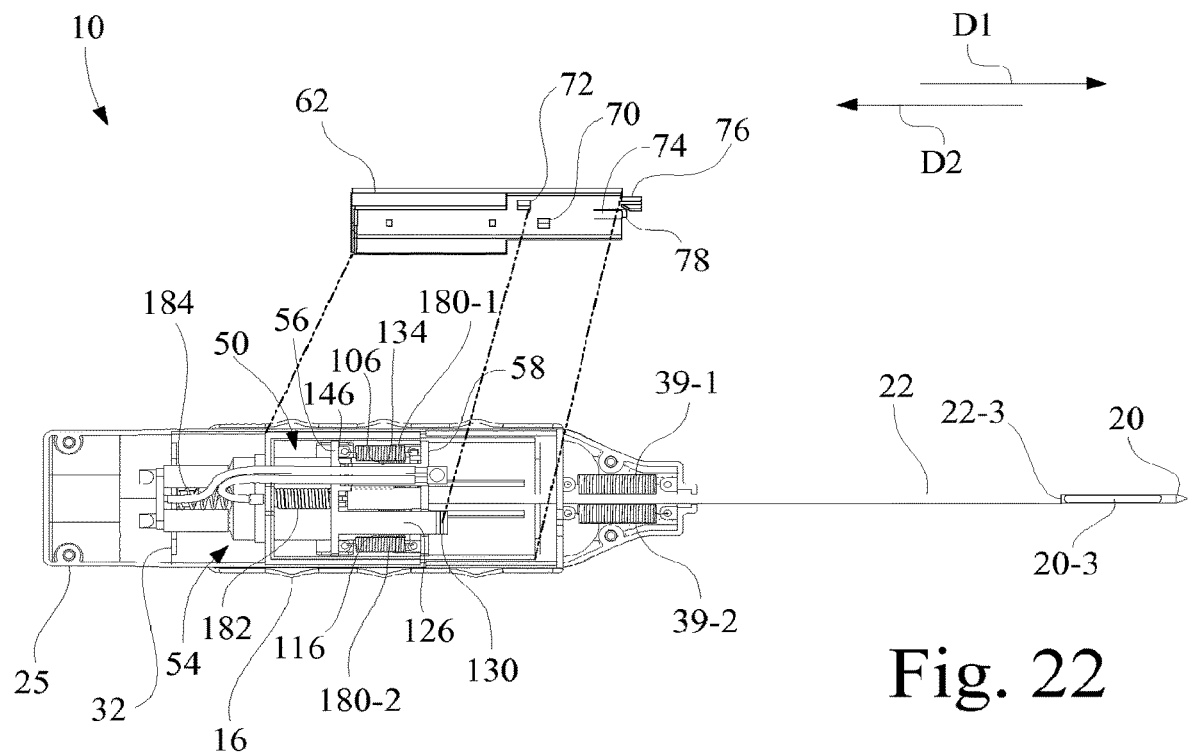
FIG. 22 shows the biopsy device depicted in FIG. 21, wherein upon release of the charge handle from the retracted position of FIG. 21, the biasing springs discharge to effect a first return (distal) stroke of the charge handle to return the charge handle to the home position.

The movement of cannula mount end wall 132 of cannula slide 58 during the first proximal stroke causes cannula 22 to be retracted to open side sample port 20-3 of stylet 20. Referring to FIG. 22, upon release of charge handle 16, biasing springs 39-1, 39-2 discharge to effect a first return (distal) stroke of charge handle 16 to return charge handle 16 to the home position, and to sequence the indexing mechanism 150 to the cannula retract position as depicted in FIG. 17 by removal of charge handle latch arm 38 from indexing window 132-1, thereby permitting sampling slide indexer 154 to move in upward direction D3 by the force exerted by cantilever spring 176, to in turn laterally positioning window blocking plate 170 of sampling slide indexer 154 over a portion, e.g., the lower left quadrant, of indexing window 132-1 of cannula slide 58.

Figure 23:
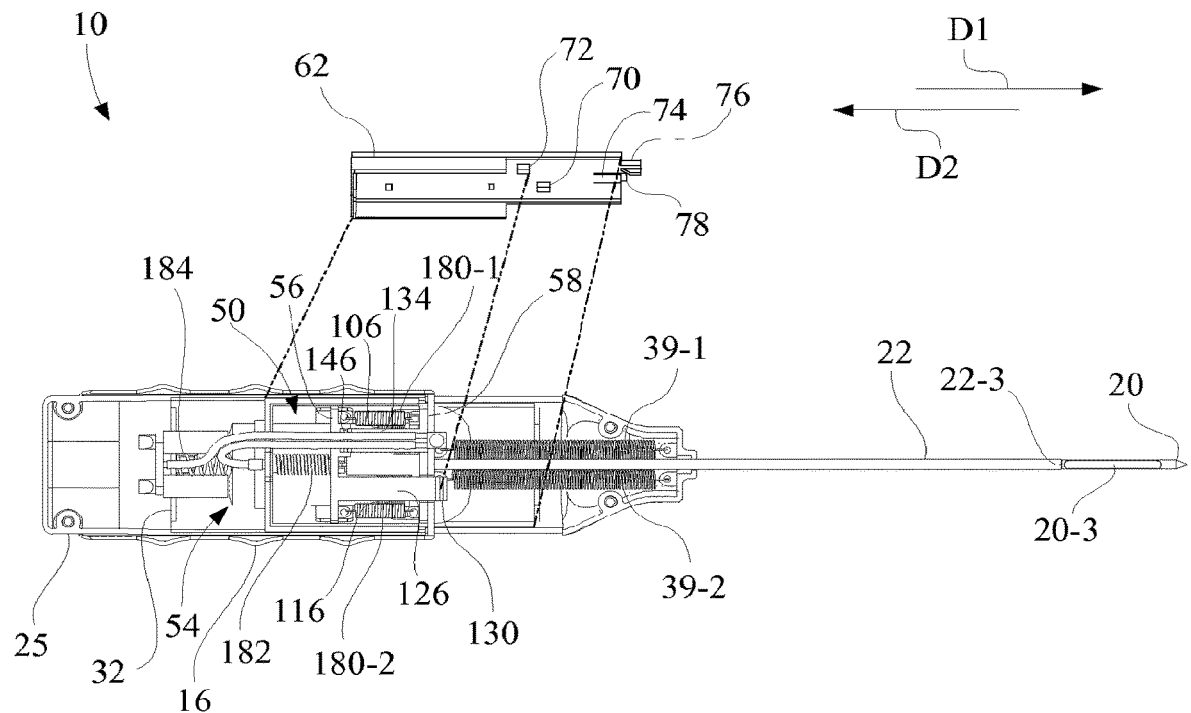
FIG. 23 shows the biopsy device depicted in FIG. 22, depicting a second retraction (proximal) stroke of the charge handle in the proximal direction to the retracted position in preparation for charging the cannula retract springs.

Referring to FIG. 23, on a second retraction (proximal) stroke of charge handle 16 in proximal direction D2, charge handle latch arm 38 of charge handle 16 attempts to pass through indexing window 132-1 of cannula slide 58, however this time the tapered nose portion of catch 38-2 of charge handle latch arm 38 slidably engages side surface 170-1 of window blocking plate 170 of sampling slide indexer 154 (see FIG. 17), and deflects around window blocking plate 170 to then pass through indexing window 132-1 of cannula slide 58. Thus, with the second retraction of charge handle 16, charge handle latch arm 38 of charge handle 16 is releasably coupled to cannula mount end wall 132 of cannula slide 58 via indexing mechanism 150.

Figure 24:
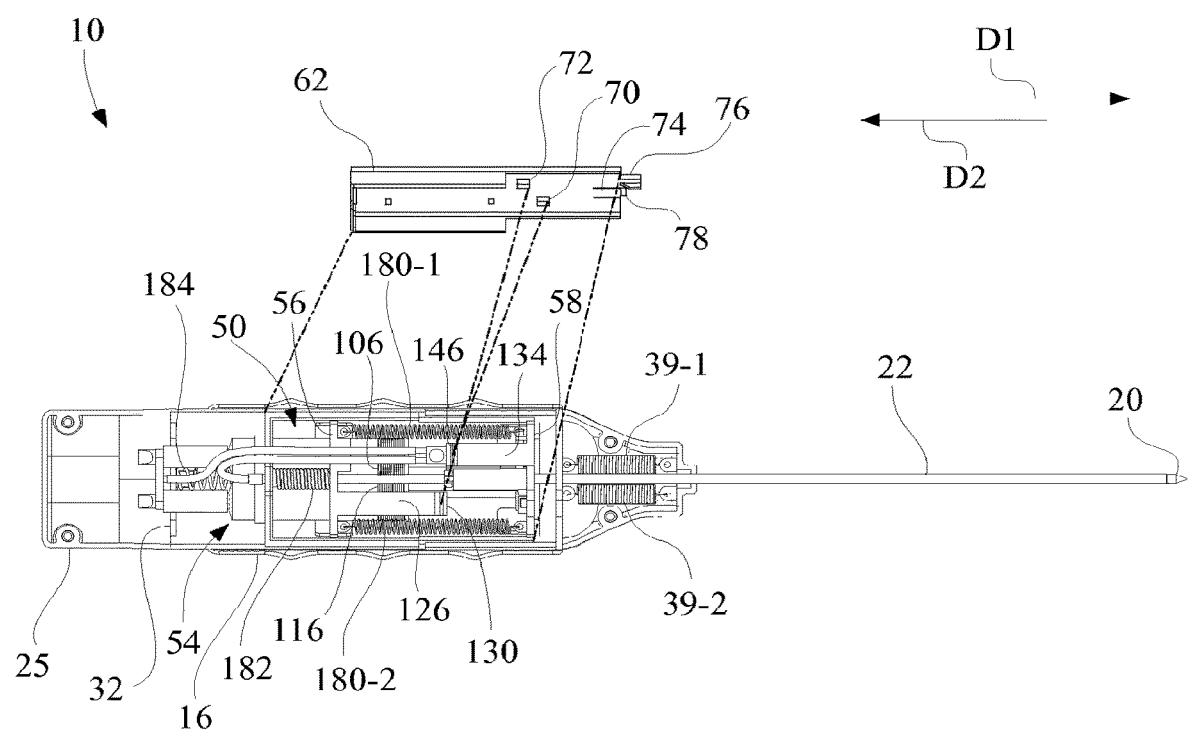
FIG. 24 shows the biopsy device depicted in FIG. 23, wherein upon release of the charge handle from the retracted position of FIG. 23, on the second return (distal) stroke, the charge handle engages and pulls the cannula slide in the distal direction away from the sampling slide to charge (extend) the cannula retract springs, and the charge handle returns to the home position.

Referring to FIG. 24, upon release of charge handle 16, biasing springs 39-1, 39-2 discharge to effect a second return (distal) stroke of charge handle 16 to return charge handle to the home position. However, on the second return (distal) stroke, catch 38-2 of charge handle latch arm 38 (see FIG. 6) catches proximal surface 170-2 of window blocking plate 170 of sampling slide indexer 154 (see FIG. 17), which in turn pulls cannula mount end wall 132 of cannula slide 58 in distal direction D1 away from intermediate slide wall 120 of sampling slide 56, and cannula 22 is moved by cannula mount end wall 132 in the distal direction D1 to close side sample port 20-3 of stylet 20. The movement of cannula mount end wall 132 of cannula slide 58 in distal direction D1 away from intermediate slide wall 120 of sampling slide 56 extends cannula retract springs 180-1, 180-2 to the charged (extended) state. As such, the force exerted by biasing springs 39-1, 39-2 and any mechanical advantage associated therewith, if any, must be greater than the force exerted by cannula retract springs 180-1, 180-2 and any mechanical advantage associated therewith, if any, so as to return charge handle 16 to the home position while pulling cannula slide 58 to its latched position.

Also, the distal movement of cannula mount end wall 132 of cannula slide 58 away from intermediate slide wall 120 of sampling slide 56 in turn causes latch arm 134 of cannula slide 58 to disengage from latch arm deflection member 128 of sampling slide 56 to thus pivot upwardly, which in turn, referring also to FIG. 18, allows cannula slide indexer 152 to pivot clockwise by the force exerted by torsion spring 162 about longitudinal axis 23, which in turn moves actuator arm 160 downwardly in direction D4 to move window blocking plate 170 of sampling slide indexer 154 downwardly in direction D4, thus opening indexing window 132-1 of cannula slide 58, thus facilitating the release of charge handle 16 from cannula slide 58.

As charge handle 16 approaches the home position, catch 146 of latch arm 134 of cannula slide 58 releasably engages latch strike 70 of carriage latch cover member 62 to retain cannula retract springs 180 in the charged (extended) state. Also, catch 130 of latch arm 126 of sampling slide 56 remains engaged with latch strike 72 of carriage latch cover member 62. With catch 146 of latch arm 134 engaged with latch strike 70 of carriage latch cover member 62 and with latch arm 126 of sampling slide 56 engaged with latch strike 72 of carriage latch cover member 62, sampling slide 56 and cannula slide 58 are spaced at a maximum separation distance from one another, and each of sampling slide 56 and cannula slide 58 are latched to maintain the maximum separation distance, until catch 146 of latch arm 134 of cannula slide 58 is released by actuation of cannula retract button 40-2.

Figure 25:
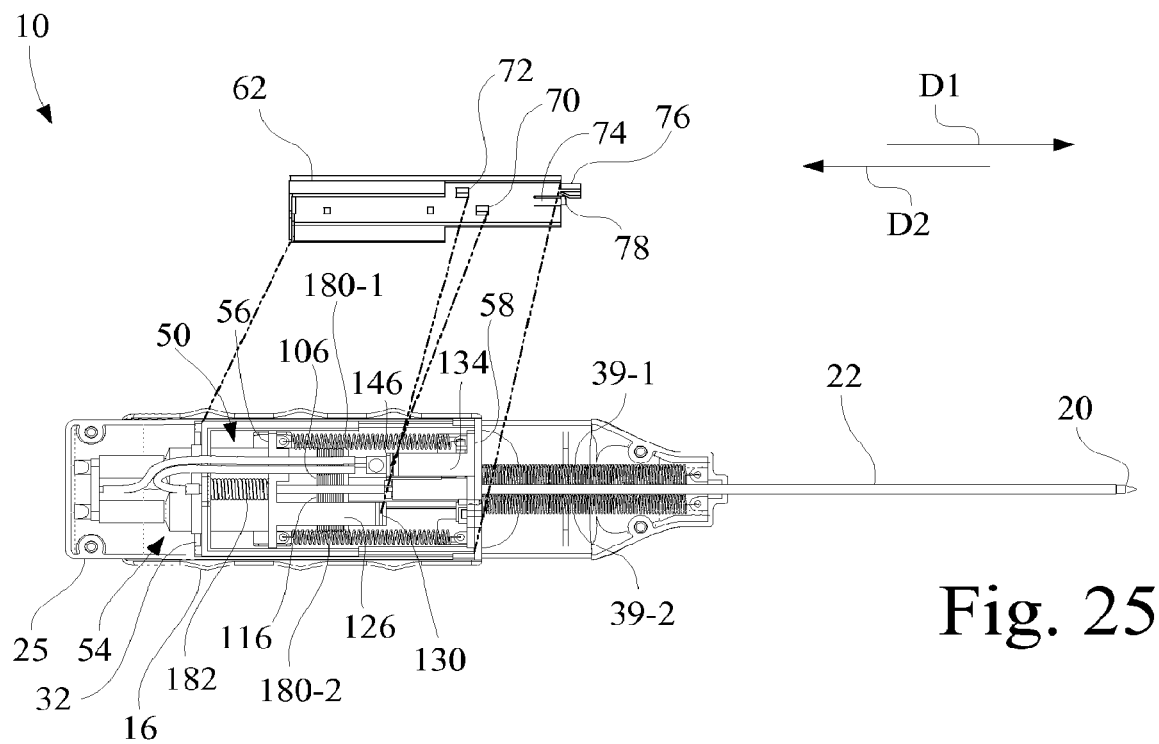
FIG. 25 shows the biopsy device depicted in FIG. 24, depicting a third retraction (proximal) stroke of the charge handle in the proximal direction to move the carriage assembly as a whole in the proximal direction to charge (compress) the prime pierce spring.

Referring to FIG. 25 in conjunction with FIG. 5, with each of catch 130 of sampling slide 56 and catch 146 of cannula slide 58 latched in latch strike 70 and latch strike 72, respectively, of carriage latch cover member 62 of prime pierce carriage 52 of carriage assembly 50, a third retraction (proximal) stroke of charge handle 16 in proximal direction D2 moves carriage assembly 50 as a whole in the proximal direction D2 to charge (compress) prime pierce spring 184. In particular, at the onset of the third proximal stroke of charging handle 16, cannula slide indexer 152 and sampling slide indexer 154 of indexing mechanism 150 are positioned as shown in FIG. 18, such that charge handle latch arm 38 of charge handle 16 (see FIG. 6) is free to pass through indexing window 132-1 of cannula slide 58, and charge handle end wall 36 of charge handle 16 engages cannula mount end wall 132 of cannula slide 58, and in turn moves carriage assembly 50 in its entirety in proximal direction D2. Stated differently, the third retraction (proximal) stroke of charge handle 16 toward to the retracted position primes biopsy needle 14 for firing by simultaneously retracting both sampling slide 56 carrying stylet 20 and cannula slide 58 carrying cannula 22, in unison, in the proximal direction D2 to charge (compress) prime pierce spring 184.

When charge handle 16 is in the retracted position at the end of the third proximal stroke, (referring also to FIGS. 7B and 10) catch 78 of carriage latch arm 74 engages carriage latch strike 44 of actuator mechanism 18 to retain prime pierce spring 184 in the compressed state.

Figure 26:
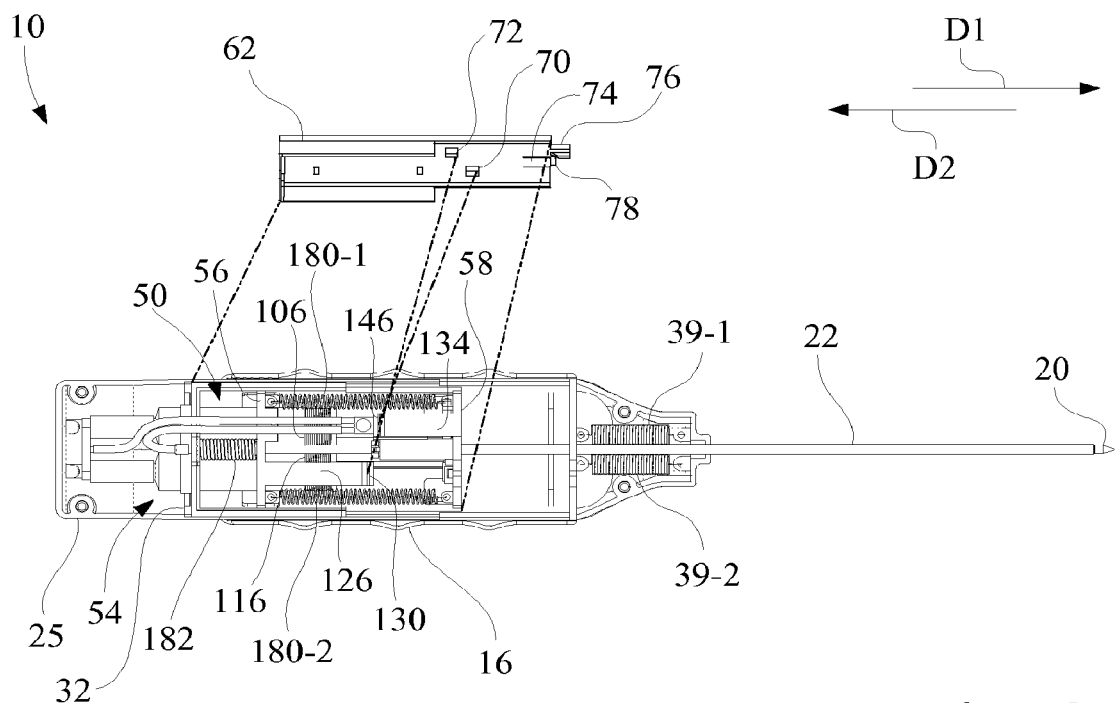
FIG. 26 shows the biopsy device depicted in FIG. 25, wherein upon release of the charge handle from the retracted position of FIG. 25, the biasing springs discharge to effect a third return (distal) stroke of the charge handle to return the charge handle to the home position.

Referring to FIG. 26, after release of charge handle 16, biasing springs 39-1, 39-2 discharge to effect a third return (distal) stroke of charge handle 16 to return charge handle 16 to the home position. Biopsy device 10 is now fully primed, with all of vacuum spring 106, 116, cannula retract springs 180-1, 180-2, sampling spring 182, and prime pierce spring 184 being in a charged state, and biopsy device is ready for operation in performing a vacuum-assisted biopsy procedure with a piercing shot function. It is to be understood that in the event that the physician performing the biopsy procedure does not choose to perform a piercing shot function, then the third retraction/return (proximal/distal) strokes of charge handle 16 can be omitted.

In the piercing shot mode of the state of biopsy device 10 shown in FIG. 26, wherein prime pierce spring 184 is charged during the third retraction (proximal) stroke, referring to FIGS. 1, 7B and 10, an actuation of pierce button 40-1 releases carriage latch arm 74 from carriage latch strike 44, so as to release prime pierce spring 184 from the charged (compressed) state to effect a transition of biopsy device 10 from the state shown in FIG. 26 to that shown in FIG. 24. Prime pierce spring 184 in turn exerts an expansion force to rapidly move carriage assembly 50 carrying stylet 20 and cannula 22, in unison, in the distal direction D1 to pierce tissue and to position biopsy needle 14 at the biopsy site within the patient.

Next, or in the absence of the piercing shot mode, with biopsy device 10 in the state shown in FIG. 24, and further referring to FIGS. 1, 5 and 10, an actuation of cannula retract button 40-2 releases latch arm 134 of cannula slide 58 from latch strike 70 of carriage latch cover member 62, thereby releasing cannula retract springs 180 from the charged (extended) state to exert a compressive force to move cannula slide 58 and cannula 22 in the proximal direction D2 to in turn open side sample port 20-3 of stylet 20 to transition biopsy device 10 from the state shown in FIG. 24 to that shown in FIG. 22. Simultaneously with this actuation of cannula retract button 40-2, cannula retract button 40-2 further actuates button actuator 96-3 of vacuum system 54 to open control valve 96 to apply the vacuum generated by vacuum pumps 90, 92 to flexible connection conduit 98-4 coupled in fluid communication with lumen 20-2 of stylet 20, and in turn to lumen 20-2 at side sample port 20-3 of stylet 20. Tissue in the vicinity of side sample port 20-3 of stylet 20 will be drawn by the vacuum into side sample port 20-3.

Next, with biopsy device 10 in the state shown in FIG. 22, and further referring to FIGS. 1, 5 and 10, an actuation of sample acquisition button 40-3 releases catch 130 of latch arm 126 from latch strike 72 of carriage latch cover member 62, thereby releasing sampling spring 182 from the charged (compressed) state to exert an expansion force to rapidly move cannula slide 58 carrying cannula 22 in the distal direction D1 to transition biopsy device 10 from the state shown in FIG. 22 to that shown in FIG. 20, and with the aid of distal cutting edge 22-3 of cannula 22, cannula 22 severs the tissue at side sample port 20-3 of stylet 20 and covers over, i.e., closes, side sample port 20-3, thereby retaining any tissue drawn into side sample port 20-3 of stylet 20 as the tissue sample, thus completing the tissue sample collection.

Following tissue sample collection, biopsy needle 14 is removed from the patient, and the first retraction (proximal) stroke is repeated so as to retract cannula 22 to open side sample port 20-3 of stylet 20. Since vacuum springs 106, 116 and sampling spring 182 are charged during the first retraction stroke of charge handle 16, then if no further tissue samples are desired, the vacuum may be purged by actuating cannula retract button 40-2, and sampling spring 182 may be discharged by actuating sample acquisition button 40-3. However, if a further tissue sample is desired, then the second retraction and return strokes are repeated to charge cannula retract springs 180-1, 180-2. Biopsy device 10 is now ready for a manual insertion into the patient, i.e., no piercing shot. However, if the piercing shot mode is desired, then the third retraction stroke of charge handle 16 is repeated to charge prime pierce spring 184 and prime biopsy needle 14 to the fully retracted position for the simultaneous firing of stylet 20 and cannula 22 into the tissue of the patient.

Thus, with respect to the various aspects of biopsy device 10 there is disclosed:

1.1. A biopsy device having a housing, a biopsy needle comprising a stylet and a cannula, a carriage assembly comprising a carriage slide, a cannula slide and a sampling slide, the carriage slide having a stylet mount end wall and the cannula slide having a cannula mount end wall, and a charge handle slidably mounted to the housing, the charge handle having a home position and a retracted position, the biopsy device further comprising a vacuum system positioned in the housing and carried by the carriage assembly, the vacuum system being charged to generate a vacuum when a sampling spring is compressed, the vacuum system including a first vacuum pump, a second vacuum pump, a manifold and a control valve, the first vacuum pump having a first vacuum port, the second vacuum pump having a second vacuum port, the manifold having a first vacuum draw port, a second vacuum draw port, and a first vacuum application port, the control valve having a third vacuum draw port and a second vacuum application port, the first vacuum port of the first vacuum pump being coupled in fluid communication with the first vacuum draw port of the manifold, the second vacuum port of the second vacuum pump being coupled in fluid communication with the second vacuum draw port of the manifold, the first vacuum application port of the manifold being coupled in fluid communication with the third vacuum draw port of the valve, the second vacuum draw port of the control valve being coupled in fluid communication with a first lumen of the stylet, the manifold having a first one-way valve coupled in fluid communication with the first vacuum draw port and a second one-way valve coupled in fluid communication with the second vacuum draw port, each of the first one-way valve and the second one-way valve configured to release positive pressure to the atmosphere and to close upon establishment of vacuum; the control valve being operated by actuation of a cannula retract button of an actuator mechanism to apply the vacuum to a side sample port of the stylet simultaneously with movement of the cannula in a proximal direction by a force generated by a cannula retract spring to open the side sample port of the stylet.

1.2. The biopsy device of paragraph 1.1, wherein: the first vacuum pump includes: a first cylinder having a first end and a second end, the first end having the first vacuum port and the second end defines a first opening; a first piston received in the first cylinder through the first opening; a first plunger attached to the first piston, the first plunger configured to extend from the second end of the first cylinder, the first plunger having a free end having a first head; and a first vacuum spring interposed between the second end of the cylinder and the first head of the first plunger, the first vacuum spring configured to store mechanical energy when in a compressed state and configured to bias the first piston in the distal direction to establish a vacuum at the first vacuum port; and the second vacuum pump includes: a second cylinder having a first end and a second end, the first end having the second vacuum port and the second end defines a second opening; a second piston received in the second cylinder through the second opening; a second plunger attached to the second piston, the second plunger configured to extend from the second end of the second cylinder, the second plunger having a free end having a second head; and a second vacuum spring interposed between the second end of the second cylinder and the second head of the second plunger, the second vacuum spring configured to store mechanical energy when in a compressed state and configured to bias the second piston in the distal direction to establish a vacuum at the second vacuum port.

1.3. The biopsy device of paragraph 1.2, wherein the first head of the first vacuum pump and the second head of the second vacuum pump are positioned for engagement with the cannula mount end wall of the cannula slide, and wherein each of the first vacuum spring of the first vacuum pump and the second vacuum spring of the second vacuum pump is compressed during a movement of the cannula mount end wall in the proximal direction that occurs prior to the cannula retract spring being charged to the extended state.

1.4. The biopsy device of paragraph 1.3, wherein compression of the first vacuum spring of the first vacuum pump and the second vacuum spring of the second vacuum pump occurs simultaneously with the compression of a sampling spring.

1.5. The biopsy device of any one of paragraphs 1.2 to 1.4, wherein the stylet mount end wall includes a first pump mounting hole and a second pump mounting hole, the first vacuum pump received in the first pump mounting hole with a first proximal cylinder portion having the first vacuum port configured to extend in the proximal direction from the stylet mount end wall and a first distal cylinder portion having the first opening configured to extend in the distal direction from the stylet mount end wall, the first head of the first plunger positioned to engage the cannula mount end wall so as to compress the first vacuum spring when the cannula mount end wall is moved in the proximal direction during a first retraction of the charge handle; and the second vacuum pump received in the second pump mounting hole with a second proximal cylinder portion having the second vacuum port configured to extend in the proximal direction from the stylet mount end wall and a second distal cylinder portion having the second opening configured to extend in the distal direction from the stylet mount end wall, the second head of the second plunger positioned to engage the cannula mount end wall so as to compress the second vacuum spring, simultaneously with compression of the first vacuum spring, when the cannula mount end wall is moved in the proximal direction during the first retraction of the charge handle.

1.6. The biopsy device of any preceding paragraph, wherein the housing comprises an actuator mechanism; the carriage assembly is movable relative to the housing, the carriage assembly including the stylet mount wall that mounts a stylet having a sample port, the cannula slide that mounts a cutting cannula, the sampling slide movably interposed between the stylet mount wall and the cannula slide, and a carriage latch cover member, the cannula slide being longitudinally spaced from and movable relative to the stylet mount wall, the cannula slide having a first latch member, the sampling slide having a second latch member, and the carriage latch cover member having a third latch member; a sampling spring interposed between the stylet mount wall and the sampling slide; a cannula retract spring interposed between, and connected to each of, the sampling slide and the cannula slide; a prime pierce spring interposed between the carriage assembly and a portion of the housing; the biopsy device configured such that: a first retraction of the charge handle moves the cannula slide and the sampling slide in unison in a proximal direction to charge the sampling spring, to latch the second latch member of the sampling slide with the carriage latch cover member to retain the sampling spring in a charged state, and to charge the vacuum system to generate the vacuum; a first return of the charge handle returns the charge handle to the home position; a second retraction of the charge handle moves the charge handle to the retracted position; a second return of the charge handle to the home position moves the cannula slide in a distal direction away from the sampling slide to charge the cannula retract spring and to latch the first latch member of the cannula slide with the carriage latch cover member to retain the cannula retract spring in a charged state; and a third retraction of the charge handle moves the carriage assembly as a whole in the proximal direction to charge the prime pierce spring and to latch the third latch member of the carriage latch cover member with the actuator mechanism to retain the prime pierce spring in a charged state.

1.7. The biopsy device of paragraph 1.6, the actuator mechanism having a cannula retract button, a sample acquisition button, and a pierce button, the biopsy device further configured such that: the pierce button is actuated to unlatch the third latch member of the carriage latch cover member from the actuator mechanism to release the prime pierce spring from the charged state to propel the carriage assembly in the distal direction to facilitate a piercing of tissue with the stylet and the cannula; the cannula retract button is actuated to unlatch the first latch member of the cannula slide from the carriage latch cover member to release the cannula retract spring from the charged state and move the cannula in the proximal direction to open a side sample port of the stylet, and to simultaneously apply the vacuum to the side sample port to draw tissue into the side sample port; and the sample acquisition button is actuated to unlatch the second latch member of the sampling slide from the carriage latch cover member to release the sampling spring from the charged state to propel the cannula in the distal direction to close the side sample port to sever the tissue drawn by vacuum into the side sample port.

1.8. The biopsy device according to any one of paragraphs 1.1 to 1.6, wherein the stylet is positioned to extend on a longitudinal axis, the stylet having a first side wall configured to define a first lumen and a side sample port that extends through the first side wall to the first lumen; the cannula is coaxial with the stylet, the cannula having a second side wall configured to define a second lumen, the cannula having a distal cutting edge, the housing has a proximal end wall, an intermediate wall, and a distal end portion spaced along the longitudinal axis, the distal end portion having a needle opening, the housing configured to define a housing chamber between the proximal end wall and the distal end portion, the intermediate wall being interposed between the proximal end wall and the distal end portion, the stylet and the cannula being received through the needle opening, and wherein a proximal direction is from the distal end portion toward the proximal end wall and a distal direction is from the proximal end wall toward the distal end portion; an actuator mechanism has a pierce button, a cannula retract button, a sample acquisition button, and having a carriage latch strike; the carriage assembly is positioned in the housing chamber, the carriage assembly configured to move longitudinally as a whole relative to the housing, the carriage assembly including the carriage slide, a carriage latch cover member, the cannula slide, and the sampling slide, each of the cannula slide and the sampling slide being configured to be movable relative to the carriage slide, the cannula slide having a first latch arm that extends in the proximal direction from the cannula mount end wall, the sampling slide being movably interposed between the stylet mount end wall of the carriage slide and the cannula mount end wall of the cannula slide, the sampling slide having a second latch arm that extends in the distal direction; the carriage latch cover member having a first latch strike, a second latch strike, and a carriage latch arm, the first latch strike configured to releasably engage the first latch arm, the second latch strike configured to releasably engage the second latch arm, and the carriage latch arm configured to releasably engage the carriage latch strike of the actuator mechanism; a sampling spring interposed between the stylet mount end wall and the sampling slide, the sampling spring configured to store mechanical energy when in a compressed state and configured to bias the sampling slide in the distal direction, the sampling spring being held in the compressed state when the second latch arm is engaged with the second latch strike; a cannula retract spring interposed between, and connected to each of, the sampling slide and the cannula slide, the cannula retract spring configured to store mechanical energy in an extended state to bias the cannula slide in the proximal direction, the cannula retract spring being releasably held in the extended state when the first latch arm is engaged with the first latch strike and the second latch arm is engaged with the second latch strike; and a prime pierce spring interposed between the intermediate wall of the housing and the stylet mount end wall, the prime pierce spring configured to store mechanical energy when in a compressed state and configured to bias the carriage assembly as a whole in the distal direction, the prime pierce spring being held in the compressed state when the carriage latch arm is engaged with the carriage latch strike of the actuator mechanism.

1.9. The biopsy device of paragraph 1.8, the charge handle configured for sequential actuations to sequentially facilitate: a movement of the sampling slide and the cannula slide collectively as a unit in the proximal direction relative to the carriage slide to charge the sampling spring, a movement of the cannula slide individually in the distal direction away from the sampling slide to charge the cannula retract spring, and a movement of the carriage assembly as a whole in the proximal direction relative to the housing to charge the prime pierce spring.

1.10. The biopsy device of any preceding paragraph, further comprising:

an indexing mechanism movably coupled to the cannula mount end wall of the cannula slide, the cannula mount end wall having an indexing window, the indexing mechanism configured to selectively cover a portion of the indexing window; and the charge handle having a charge handle latch arm configured to pass through the indexing window when the charge handle is moved to the retracted position, and when the indexing mechanism is positioned to cover the portion of the indexing window, a subsequent movement of the charge handle in the distal direction toward the home position causes the charge handle latch arm to engage the indexing mechanism to move the cannula slide in the distal direction away from the sampling slide to charge the cannula retract spring.

1.11. The biopsy device of any preceding paragraph, wherein the cannula retract spring is a pair of laterally spaced springs.

1.12. The biopsy device of any preceding paragraph, further comprising a biasing spring coupled to the housing and to the charge handle, the biasing spring configured to bias the charge handle in the distal direction to the home position.

1.13. The biopsy device of paragraph 1.12, wherein a force exerted by the biasing spring is greater than a force exerted by the cannula retract spring.

1.14. The biopsy device of paragraph 1.12 or paragraph 1.13, wherein the biasing spring is a pair of laterally spaced springs.

1.15. The biopsy device of any one of paragraphs 1.1 to 1.9, comprising: an indexing mechanism movably coupled to the cannula mount end wall of the cannula slide, the charge handle and the indexing mechanism in combination configured to selectively facilitate movement of the sampling slide and the cannula slide collectively as a unit in the proximal direction relative to the carriage slide to charge the sampling spring, to facilitate movement of the cannula slide individually in a distal direction relative to carriage slide to charge the cannula retract spring, and to facilitate movement of the carriage assembly as a whole in the proximal direction relative to the housing to charge the prime pierce spring.

1.16. The biopsy device of any one of paragraphs 1.1 to 1.9, comprising: the cannula mount end wall having an indexing window; the charge handle having a charge handle latch arm configured to pass through the indexing window; and an indexing mechanism having a cannula slide indexer and a sampling slide indexer, the cannula slide indexer being rotatably coupled to the cannula mount end wall of the cannula slide, the sampling slide indexer being slidably coupled to the cannula mount end wall of the cannula slide and configured to move in a first direction toward the longitudinal axis, the cannula slide indexer being operably engaged with the sampling slide indexer, sampling slide indexer being biased by a bias spring in the first direction, the sampling slide indexer having a window blocking plate configured to cover a portion of the indexing window when the sampling slide indexer is moved in the first direction; the cannula slide indexer being configured to be operably engaged by the first latch arm of the cannula slide to rotate the cannula slide indexer into contact with the sampling slide indexer to move the sampling slide indexer in a second direction opposite to the first direction such that the window blocking plate of the sampling slide indexer does not cover the portion of the indexing window, the sampling slide indexer being configured to be operably engaged by the second latch arm of the second latch arm of the sampling slide to move the sampling slide indexer in the second direction opposite to the first direction such that the window blocking plate of the sampling slide indexer does not cover the portion of the indexing window, wherein when the window blocking plate of the sampling slide indexer is positioned to cover the portion of the indexing window, the charge handle configured to be moved in a proximal stroke such that the charge handle latch arm passes through the indexing window and passes the window blocking plate of the sampling slide indexer, the charge handle configured such that in a return distal stroke of the charge handle in the distal direction toward the home position causes the charge handle latch arm to engage the window blocking plate to move the cannula slide in the distal direction away from the sampling slide to charge the cannula retract spring.

1.17. The biopsy device of paragraph 1.16, the sampling slide further including a slider wall and a latch arm deflection member, the second latch arm configured to extend in a distal direction from the slider wall, the second latch arm configured to releasably engage the second latch strike of the carriage latch cover member, the latch arm deflection member configured to engage the first latch arm of the cannula slide and deflect the first latch arm to engage with the cannula slide indexer of the indexing mechanism, the cannula slide indexer being rotated to allow movement of the sampling slide indexer in the first direction.

1.18. The biopsy device of any one of paragraphs 1.1 to 1.9, further comprising: an indexing mechanism movably coupled to the cannula mount end wall of the cannula slide, the cannula mount end wall having an indexing window, the indexing mechanism configured to selectively cover a portion of the indexing window; the charge handle having a charge handle latch arm that extends in the proximal direction; and a biasing spring coupled to the housing and to the charge handle, the biasing spring configured to bias the charge handle in the distal direction to the home position, the charge handle configured for sequential actuations, wherein: a first retraction of the charge handle moves the sampling slide and the cannula mount end wall that carries the cannula, in unison, by virtue of the first latch arm being engaged with the sampling slide, in the proximal direction to compress the sampling spring and to engage the second latch arm with the second latch strike to retain the sampling spring in the compressed state, the cannula being retracted to expose the side sample port of the stylet, the charge handle configured to return to the home position by force exerted by the biasing mechanism; a second retraction of the charge handle passes the charge handle latch arm through the indexing window, and during the return of the charge handle to the home position by force exerted by the biasing mechanism: the charge handle latch arm engages the indexing mechanism and moves the cannula slide in the distal direction away from the sampling slide which in turn extends the cannula retract spring to the extended state, the first latch arm releasably engages the first latch strike to retain the cannula retract spring in the extended state, and the indexing mechanism is sequenced to fully open the indexing window of the cannula slide to disengage the indexing mechanism from the charge handle latch arm, the cannula being positioned to close the side sample port of the stylet; and a third retraction of the charge handle moves the carriage assembly as a whole in the proximal direction to compress the prime pierce spring, the carriage latch arm configured to engage the carriage latch strike of the actuator mechanism to retain the prime pierce spring in the compressed state.

1.19. The biopsy device of paragraph 1.18, configured wherein: an actuation of the pierce button releases the carriage latch arm from the carriage latch strike, the prime pierce spring being released from the compressed state to exert a force to move the carriage assembly, including the stylet and the cannula in unison, in the distal direction; an actuation of the cannula retract button releases the first latch arm from the first latch strike, the cannula retract spring being released from the extended state to exert a force to move the cannula in the proximal direction and open the side sample port of the stylet; and an actuation of the sample acquisition button releases the second latch arm from the second latch strike, the sampling spring being released from the compressed state to exert a force to move the cannula in the distal direction to close the side sample port.

1.20. The biopsy device of any of the previous paragraphs, wherein the stylet has an open first end and a closed second end, the closed second end defining a distal piercing tip.

1.21. The biopsy device of any of the previous paragraphs, wherein the carriage slide further includes a carriage base, the stylet mount end wall and the carriage base being formed as a unitary carriage structure, the carriage base configured to define a U-shaped wall having a U-shaped cross-section that extends in the distal direction from the stylet mount end wall to define an open distal end and an open top, the carriage latch cover member configured to attach to the carriage base to cover the open top, the open distal end configured to slidably receive and longitudinally guide the sampling slide and the cannula slide.

1.22. A biopsy device, comprising: a housing having a longitudinal axis, the housing configured to define a housing chamber; an actuator mechanism having a cannula retract button, a sample acquisition button, and a carriage latch strike; a carriage assembly positioned in the housing chamber, the carriage assembly including a carriage slide having a carriage base and a stylet mount wall, the carriage assembly further including a sampling slide, a cannula slide and a carriage latch cover member, the cannula slide being longitudinally spaced from and movable relative to the stylet mount wall, the cannula slide having a first latch arm, the carriage latch cover member being fixedly attached to the carriage base, the carriage latch cover member having a first latch strike and a second latch strike, the first latch arm of the cannula slide configured to releasably engage the first latch strike of the carriage latch cover member; a stylet fixedly connected to stylet mount wall, the stylet configured to extend along the longitudinal axis, the stylet having a side sample port; a vacuum source carried by the carriage assembly, the vacuum source configured to selectively apply a vacuum to the side sample port of the stylet; a cannula fixedly connected to the cannula slide, the cannula being coaxial with the stylet, the cannula having a distal cutting edge; a sampling slide movably interposed between the stylet mount wall and the cannula slide, the sampling slide having a second latch arm and a latch arm deflection member, the second latch arm configured to releasably engage the second latch strike of the carriage latch cover member, the latch arm deflection member configured to engage the first latch arm of the cannula slide and deflect the first latch arm toward the carriage base; a sampling spring interposed between the stylet mount wall and the sampling slide, the sampling spring being held in the compressed state when the second latch arm is engaged with the second latch strike; a cannula retract spring interposed between, and connected to each of, the sampling slide and the cannula slide, the cannula retract spring being releasably held in an extended state to store mechanical energy when the first latch arm is engaged with the first latch strike and the second latch arm is engaged with the second latch strike; a cocking mechanism having a charge handle, a biasing spring, and an indexing mechanism, the charge handle slidably mounted to the housing and biased by the biasing spring in the distal direction to a home position, the charge handle configured to move between the home position and a retracted position, the indexing mechanism being movably coupled to the cannula slide, wherein: a first retraction of the charge handle moves the sampling slide and the cannula slide in unison in the proximal direction to compress the sampling spring, to engage the second latch arm with the second latch strike to retain the sampling spring in the compressed state, and to charge the vacuum source, the charge handle configured to return to the home position by force exerted by the biasing spring and to sequence the indexing mechanism to a next selection position; and a second retraction of the charge handle moves the charge handle to the retracted position, and during a return of the charge handle to the home position by force exerted by the biasing spring, the charge handle engages the indexing mechanism movably coupled to the cannula slide and the cannula slide is moved in the distal direction which in turn extends the cannula retract spring to the extended state and the first latch arm releasably engages the first latch strike to retain the cannula retract spring in the extended state, the cannula being positioned to close the side sample port of the stylet; and the actuator mechanism configured such that: an actuation of the cannula retract button releases the first latch arm from the first latch strike to in turn release the cannula retract spring to exert a retraction force to move the cannula in the proximal direction to open the side sample port of the stylet and to simultaneously apply the vacuum to the side sample port; and an actuation of the sample acquisition button releases the second latch arm from the second latch strike to release the sampling spring to exert a force to move the cannula in the distal direction to close the side sample port.

1.23. The biopsy device of paragraph 1.22, the carriage assembly configured to move as a whole longitudinally relative to the housing, and further comprising: the actuator mechanism having a pierce button and a carriage latch strike; the carriage latch cover member having a carriage latch arm, the carriage latch arm configured to releasably engage the carriage latch strike; an intermediate wall interposed in the housing between the proximal end wall and the distal end portion; a prime pierce spring interposed between the intermediate wall and the stylet mount wall, the prime pierce spring configured to store mechanical energy when in a compressed state and configured to bias the carriage assembly as a whole in the distal direction, the prime pierce spring being held in the compressed state when the carriage latch arm is engaged with the carriage latch strike of the actuator mechanism, wherein: a third retraction of the charge handle prior to operation of the actuator mechanism moves the carriage assembly as a whole in the proximal direction to compress the prime pierce spring, the carriage latch arm configured to engage the carriage latch strike of the actuator mechanism to retain the prime pierce spring in the compressed state; and, prior to actuation of the cannula retract button and the sample acquisition button, an actuation of the pierce button releases the carriage latch arm from the carriage latch strike, the prime pierce spring being released from the compressed state to exert a force to move the carriage assembly, the stylet, and the cannula in unison in the distal direction.

1.24. A method of operating a biopsy device, comprising: providing a housing having an actuator mechanism; providing a carriage assembly movable relative to the housing, the carriage assembly including a stylet mount wall that mounts a stylet, a cannula slide that mounts a cutting cannula, a sampling slide movably interposed between the stylet mount wall and the cannula slide, and a carriage latch cover member, the cannula slide being longitudinally spaced from and movable relative to the stylet mount wall; providing a charge handle to sequentially move at least one of the cannula slide, the sampling slide, and the carriage assembly as a whole, the charge handle having a home position and a retracted position; providing a sampling spring interposed between the stylet mount wall and the sampling slide; providing a cannula retract spring interposed between, and connected to each of, the sampling slide and the cannula slide; providing a prime pierce spring interposed between the carriage assembly and a portion of the housing; providing a vacuum system to selectively supply a vacuum to a sample port of the stylet; retracting the charge handle a first time to move the cannula slide and the sampling slide in unison in a proximal direction to charge a sampling spring, to latch the sampling slide with the carriage latch cover member to retain the sampling spring in a charged state, and to charge the vacuum system with a vacuum; returning the charge handle a first time to the home position; retracting the charge handle a second time to the retracted position; returning the charge handle a second time to the home position to move the cannula slide in a distal direction relative to the sampling slide to charge the cannula retract spring and to latch the cannula slide with the carriage latch cover member to retain the cannula retract spring in a charged state; and retracting the charge handle a third time to move the carriage assembly as a whole in the proximal direction to charge the prime pierce spring and to latch the carriage latch cover member with the actuator mechanism to retain the prime pierce spring in a charged state.

1.25. The method of paragraph 24, the actuator mechanism having a cannula retract button, a sample acquisition button, and a pierce button, the method further comprising: actuating the pierce button to unlatch the carriage latch cover member from the actuator mechanism to release the prime pierce spring from the charged state to propel the carriage assembly in the distal direction to facilitate a piercing of tissue with the stylet and the cannula; actuating the cannula retract button to unlatch the cannula slide from the carriage latch cover member to release the cannula retract spring from the charged state and move the cannula in the proximal direction to open a side sample port of the stylet and to simultaneously apply the vacuum to the side sample port to draw tissue into the side sample port; and actuating the sample acquisition button to unlatch the sampling slide from the carriage latch cover member to release the sampling spring from the charged state to propel the cannula in the distal direction to close the side sample port to sever the tissue drawn by vacuum into the side sample port.

While this invention has been described with respect to at least one embodiment, those skilled in the art will recognize that the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device, comprising:
a housing having an actuator mechanism;
a carriage assembly movable relative to the housing, the carriage assembly including a stylet mount wall that mounts a stylet having a sample port, a cannula slide that mounts a cutting cannula, a sampling slide movably interposed between the stylet mount wall and the cannula slide, and a carriage latch cover member, the cannula slide being longitudinally spaced from and movable relative to the stylet mount wall, the cannula slide having a first latch member, the sampling slide having a second latch member, and the carriage latch cover member having a third latch member;
a charge handle slidably mounted to the housing, the charge handle having a home position and a retracted position;
a sampling spring interposed between the stylet mount wall and the sampling slide;
a cannula retract spring interposed between, and connected to each of, the sampling slide and the cannula slide;
a prime pierce spring interposed between the carriage assembly and a portion of the housing; and
a vacuum system configured to selectively supply a vacuum to the sample port of the stylet;
the biopsy device configured such that:
a first retraction of the charge handle moves the cannula slide and the sampling slide in unison in a proximal direction to charge the sampling spring, to latch the second latch member of the sampling slide with the carriage latch cover member to retain the sampling spring in a charged state, and to charge the vacuum system to generate the vacuum;
a first return of the charge handle returns the charge handle to the home position;
a second retraction of the charge handle moves the charge handle to the retracted position;
a second return of the charge handle to the home position moves the cannula slide in a distal direction away from the sampling slide to charge the cannula retract spring and to latch the first latch member of the cannula slide with the carriage latch cover member to retain the cannula retract spring in a charged state; and
a third retraction of the charge handle moves the carriage assembly as a whole in the proximal direction to charge the prime pierce spring and to latch the third latch member of the carriage latch cover member with the actuator mechanism to retain the prime pierce spring in a charged state.

2. The biopsy device of claim 1, the actuator mechanism having a cannula retract button, a sample acquisition button, and a pierce button, the biopsy device further configured such that:
the pierce button is actuated to unlatch the third latch member of the carriage latch cover member from the actuator mechanism to release the prime pierce spring from the charged state to propel the carriage assembly in the distal direction to facilitate simultaneous distal movement of the stylet and the cannula;
the cannula retract button is actuated to unlatch the first latch member of the cannula slide from the carriage latch cover member to release the cannula retract spring from the charged state and move the cannula in the proximal direction to open the sample port of the stylet, and to simultaneously apply the vacuum to the sample port; and
the sample acquisition button is actuated to unlatch the second latch member of the sampling slide from the carriage latch cover member to release the sampling spring from the charged state to propel the cannula in the distal direction to close the sample port.

3. A biopsy device, comprising:
a stylet positioned to extend on a longitudinal axis, the stylet having a first side wall configured to define a first lumen and a side sample port that extends through the first side wall to the first lumen;
a cannula coaxial with the stylet, the cannula having a second side wall configured to define a second lumen, the cannula having a distal cutting edge;

a housing having a proximal end wall, an intermediate wall, and a distal end portion spaced along the longitudinal axis, the distal end portion having a needle opening, the housing configured to define a housing chamber between the proximal end wall and the distal end portion, the intermediate wall being interposed between the proximal end wall and the distal end portion, the stylet and the cannula being received through the needle opening, and wherein a proximal direction is from the distal end portion toward the proximal end wall and a distal direction is from the proximal end wall toward the distal end portion;

a charge handle slidably mounted to the housing, the charge handle configured to move between a home position and a retracted position;

an actuator mechanism having a pierce button, a cannula retract button, a sample acquisition button, and a carriage latch strike;

a carriage assembly positioned in the housing chamber, the carriage assembly configured to move longitudinally as a whole relative to the housing, the carriage assembly including a carriage slide, a carriage latch cover member, a cannula slide, and a sampling slide, each of the cannula slide and the sampling slide being configured to be movable relative to the carriage slide, the carriage slide having a stylet mount end wall configured to mount the stylet, the cannula slide having a cannula mount end wall configured to mount the cannula and having a first latch arm that extends in the proximal direction from the cannula mount end wall, the sampling slide being movably interposed between the stylet mount end wall of the carriage slide and the cannula mount end wall of the cannula slide, the sampling slide having a second latch arm that extends in the distal direction;

the carriage latch cover member having a first latch strike, a second latch strike, and a carriage latch arm, the first latch strike configured to releasably engage the first latch arm, the second latch strike configured to releasably engage the second latch arm, and the carriage latch arm configured to releasably engage the carriage latch strike of the actuator mechanism; a sampling spring interposed between the stylet mount end wall and the sampling slide, the sampling spring configured to store mechanical energy when in a compressed state and configured to bias the sampling slide in the distal direction, the sampling spring being held in the compressed state when the second latch arm is engaged with the second latch strike;

a vacuum system positioned in the housing and carried by the carriage assembly, the vacuum system being charged to generate a vacuum when the sampling spring is compressed;

a cannula retract spring interposed between, and connected to each of, the sampling slide and the cannula slide, the cannula retract spring configured to store mechanical energy in an extended state to bias the cannula slide in the proximal direction, the cannula retract spring being releasably held in the extended state when the first latch arm is engaged with the first latch strike and the second latch arm is engaged with the second latch strike; and a prime pierce spring interposed between the intermediate wall of the housing and the stylet mount end wall, the prime pierce spring configured to store mechanical energy when in a compressed state and configured to bias the carriage assembly as a whole in the distal direction, the prime pierce spring being held in the compressed state when the carriage latch arm is engaged with the carriage latch strike of the actuator mechanism.

4. The biopsy device of claim 3, the charge handle configured for sequential actuations to sequentially facilitate:
a movement of the sampling slide and the cannula slide collectively as a unit in the proximal direction relative to the carriage slide to charge the sampling spring,
a movement of the cannula slide individually in the distal direction away from the sampling slide to charge the cannula retract spring, and
a movement of the carriage assembly as a whole in the proximal direction relative to the housing to charge the prime pierce spring.

5. The biopsy device of claim 4, further comprising:
an indexing mechanism movably coupled to the cannula mount end wall of the cannula slide, the cannula mount end wall having an indexing window, the indexing mechanism configured to selectively cover a portion of the indexing window; and
the charge handle having a charge handle latch arm configured to pass through the indexing window when the charge handle is moved to the retracted position, and when the indexing mechanism is positioned to cover the portion of the indexing window, a subsequent movement of the charge handle in the distal direction toward the home position causes the charge handle latch arm to engage the indexing mechanism to move the cannula slide in the distal direction away from the sampling slide to charge the cannula retract spring.

6. The biopsy device of claim 5, wherein the cannula retract spring is a pair of laterally spaced springs.

7. The biopsy device of claim 4, further comprising a biasing spring coupled to the housing and to the charge handle, the biasing spring configured to bias the charge handle in the distal direction to the home position.

8. The biopsy device of claim 7, wherein a force exerted by the biasing spring is greater than a force exerted by the cannula retract spring.

9. The biopsy device of claim 7, wherein the biasing spring is a pair of laterally spaced springs.

10. The biopsy device of claim 3, comprising:
an indexing mechanism movably coupled to the cannula mount end wall of the cannula slide,
the charge handle and the indexing mechanism in combination configured to selectively facilitate movement of the sampling slide and the cannula slide collectively as a unit in the proximal direction relative to the carriage slide to charge the sampling spring, to facilitate movement of the cannula slide individually in the distal direction relative to the carriage slide to charge the cannula retract spring, and to facilitate movement of the carriage assembly as a whole in the proximal direction relative to the housing to charge the prime pierce spring.

11. The biopsy device of claim 3, comprising:
the cannula mount end wall having an indexing window;
the charge handle having a charge handle latch arm configured to pass through the indexing window;
an indexing mechanism having a cannula slide indexer and a sampling slide indexer, the cannula slide indexer being rotatably coupled to the cannula mount end wall of the cannula slide, the sampling slide indexer being slidably coupled to the cannula mount end wall of the cannula slide and configured to move in a first direction toward the longitudinal axis, the cannula slide indexer being operably engaged with the sampling slide indexer, the sampling slide indexer being biased by a bias spring in the first direction, the sampling slide indexer having a window blocking plate configured to cover a portion of the indexing window when the sampling slide indexer is moved in the first direction;

the cannula slide indexer being configured to be operably engaged by the first latch arm of the cannula slide to rotate the cannula slide indexer into contact with the sampling slide indexer to move the sampling slide indexer in a second direction opposite to the first direction such that the window blocking plate of the sampling slide indexer does not cover the portion of the indexing window; and the sampling slide indexer being configured to be operably engaged by the second latch arm of the sampling slide to move the sampling slide indexer in the second direction opposite to the first direction such that the window blocking plate of the sampling slide indexer does not cover the portion of the indexing window, wherein when the window blocking plate of the sampling slide indexer is positioned to cover the portion of the indexing window, the charge handle is configured to be moved in a proximal stroke such that the charge handle latch arm passes through the indexing window and passes the window blocking plate of the sampling slide indexer, the charge handle configured such that a return distal stroke of the charge handle in the distal direction toward the home position causes the charge handle latch arm to engage the window blocking plate to move the cannula slide in the distal direction away from the sampling slide to charge the cannula retract spring.

12. The biopsy device of claim 11, the sampling slide further including a slider wall and a latch arm deflection member, the second latch arm configured to extend in the distal direction from the slider wall, the second latch arm configured to releasably engage the second latch strike of the carriage latch cover member, the latch arm deflection member configured to engage the first latch arm of the cannula slide and deflect the first latch arm to engage with the cannula slide indexer of the indexing mechanism, the cannula slide indexer being rotated to allow movement of the sampling slide indexer in the first direction.

13. The biopsy device of claim 3, further comprising:
an indexing mechanism movably coupled to the cannula mount end wall of the cannula slide, the cannula mount end wall having an indexing window, the indexing mechanism configured to selectively cover a portion of the indexing window;
the charge handle having a charge handle latch arm that extends in the proximal direction; and
a biasing spring coupled to the housing and to the charge handle, the biasing spring configured to bias the charge handle in the distal direction to the home position,
the charge handle configured for sequential actuations, wherein:
a first retraction of the charge handle moves the sampling slide and the cannula mount end wall that mounts the cannula, in unison, by virtue of the first latch arm being engaged with the sampling slide, in the proximal direction to compress the sampling spring and to engage the second latch arm with the second latch strike to retain the sampling spring in the compressed state, the cannula being retracted to expose the side sample port of the stylet, the charge handle configured to return to the home position by force exerted by the biasing spring;
a second retraction of the charge handle passes the charge handle latch arm through the indexing window, and during the return of the charge handle to the home position by force exerted by the biasing spring:
the charge handle latch arm engages the indexing mechanism and moves the cannula slide in the distal direction away from the sampling slide which in turn extends the cannula retract spring to the extended state,
the first latch arm releasably engages the first latch strike to retain the cannula retract spring in the extended state, and
the indexing mechanism is sequenced to fully open the indexing window of the cannula slide to disengage the indexing mechanism from the charge handle latch arm,
the cannula being positioned to close the side sample port of the stylet; and
a third retraction of the charge handle moves the carriage assembly as a whole in the proximal direction to compress the prime pierce spring, the carriage latch arm configured to engage the carriage latch strike of the actuator mechanism to retain the prime pierce spring in the compressed state.

14. The biopsy device of claim 13, configured such that:
an actuation of the pierce button releases the carriage latch arm from the carriage latch strike, the prime pierce spring being released from the compressed state to exert a force to move the carriage assembly, including the stylet and the cannula in unison, in the distal direction;
an actuation of the cannula retract button releases the first latch arm from the first latch strike, the cannula retract spring being released from the extended state to exert a force to move the cannula in the proximal direction and open the side sample port of the stylet; and
an actuation of the sample acquisition button releases the second latch arm from the second latch strike, the sampling spring being released from the compressed state to exert a force to move the cannula in the distal direction to close the side sample port.

15. The biopsy device of claim 3, the vacuum system including a first vacuum pump, a second vacuum pump, a manifold and a control valve,
the first vacuum pump having a first vacuum port,
the second vacuum pump having a second vacuum port,
the manifold having a first vacuum draw port, a second vacuum draw port, and a first vacuum application port,
the control valve having a third vacuum draw port and a second vacuum application port,
the first vacuum port of the first vacuum pump being coupled in fluid communication with the first vacuum draw port of the manifold, the second vacuum port of the second vacuum pump being coupled in fluid communication with the second vacuum draw port of the manifold, the first vacuum application port of the manifold being coupled in fluid communication with the third vacuum draw port of the control valve, the second vacuum application port of the control valve being coupled in fluid communication with the first lumen of the stylet,
the manifold having a first one-way valve coupled in fluid communication with the first vacuum draw port and a second one-way valve coupled in fluid communication with the second vacuum draw port, each of the first one-way valve and the second one-way valve configured to release positive pressure to the atmosphere and to close upon establishment of vacuum, and the control valve being operated by actuation of the cannula retract button of the actuator mechanism to apply the vacuum to the side sample port of the stylet simultaneously with movement of the cannula in the proximal direction by a force generated by the cannula retract spring to open the side sample port of the stylet.

16. The biopsy device of claim 15, wherein:
the first vacuum pump includes:
  a first cylinder having a first end and a second end, the first end having the first vacuum port and the second end defining a first opening;
  a first piston received in the first cylinder through the first opening;
  a first plunger attached to the first piston, the first plunger configured to extend from the second end of the first cylinder, the first plunger having a free end having a first head; and
  a first vacuum spring interposed between the second end of the first cylinder and the first head of the first plunger, the first vacuum spring configured to store mechanical energy when in a compressed state and configured to bias the first piston in the distal direction to establish a vacuum at the first vacuum port; and
the second vacuum pump includes:
  a second cylinder having a first end and a second end, the first end having the second vacuum port and the second end defining a second opening;
  a second piston received in the second cylinder through the second opening;
  a second plunger attached to the second piston, the second plunger configured to extend from the second end of the second cylinder, the second plunger having a free end having a second head; and
  a second vacuum spring interposed between the second end of the second cylinder and the second head of the second plunger, the second vacuum spring configured to store mechanical energy when in a compressed state and configured to bias the second piston in the distal direction to establish a vacuum at the second vacuum port.

17. The biopsy device of claim 16, wherein the first head of the first vacuum pump and the second head of the second vacuum pump are positioned for engagement with the cannula mount end wall of the cannula slide, and wherein each of the first vacuum spring of the first vacuum pump and the second vacuum spring of the second vacuum pump is compressed during a movement of the cannula mount end wall in the proximal direction that occurs prior to the cannula retract spring being charged to the extended state.

18. The biopsy device of claim 17, wherein compression of the first vacuum spring of the first vacuum pump and the second vacuum spring of the second vacuum pump occurs simultaneously with the compression of the sampling spring.

19. The biopsy device of claim 16, wherein the stylet mount end wall includes a first pump mounting hole and a second pump mounting hole,
  the first vacuum pump being received in the first pump mounting hole with a first proximal cylinder portion having the first vacuum port configured to extend in the proximal direction from the stylet mount end wall and a first distal cylinder portion having the first opening configured to extend in the distal direction from the stylet mount end wall, the first head of the first plunger positioned to engage the cannula mount end wall so as to compress the first vacuum spring when the cannula mount end wall is moved in the proximal direction during a first retraction of the charge handle, and
  the second vacuum pump being received in the second pump mounting hole with a second proximal cylinder portion having the second vacuum port configured to extend in the proximal direction from the stylet mount end wall and a second distal cylinder portion having the second opening configured to extend in the distal direction from the stylet mount end wall, the second head of the second plunger positioned to engage the cannula mount end wall so as to compress the second vacuum spring, simultaneously with compression of the first vacuum spring, when the cannula mount end wall is moved in the proximal direction during the first retraction of the charge handle.

20. The biopsy device of claim 3, wherein the stylet has an open first end and a closed second end, the closed second end defining a distal piercing tip.

21. The biopsy device of claim 3, wherein the carriage slide further includes a carriage base, the stylet mount end wall and the carriage base being formed as a unitary carriage structure, the carriage base configured to define a U-shaped wall having a U-shaped cross-section that extends in the distal direction from the stylet mount end wall to define an open distal end and an open top, the carriage latch cover member configured to attach to the carriage base to cover the open top, the open distal end configured to slidably receive and longitudinally guide the sampling slide and the cannula slide.

22. A biopsy device, comprising:
  a housing having a longitudinal axis, the housing configured to define a housing chamber;
  an actuator mechanism having a cannula retract button, a sample acquisition button, and a carriage latch strike;
  a carriage assembly positioned in the housing chamber, the carriage assembly including a carriage slide having a carriage base and a stylet mount wall, the carriage assembly further including a sampling slide, a cannula slide and a carriage latch cover member, the cannula slide being longitudinally spaced from and movable relative to the stylet mount wall, the cannula slide having a first latch arm, the carriage latch cover member being fixedly attached to the carriage base, the carriage latch cover member having a first latch strike and a second latch strike, the first latch arm of the cannula slide configured to releasably engage the first latch strike of the carriage latch cover member;
  a stylet fixedly connected to the stylet mount wall, the stylet configured to extend along the longitudinal axis, the stylet having a side sample port;
  a vacuum source carried by the carriage assembly, the vacuum source configured to selectively apply a vacuum to the side sample port of the stylet;
  a cannula fixedly connected to the cannula slide, the cannula being coaxial with the stylet, the cannula having a distal cutting edge;
  the sampling slide movably interposed between the stylet mount wall and the cannula slide, the sampling slide having a second latch arm and a latch arm deflection member, the second latch arm configured to releasably engage the second latch strike of the carriage latch cover member, the latch arm deflection member configured to engage the first latch arm of the cannula slide and deflect the first latch arm toward the carriage base;
  a sampling spring interposed between the stylet mount wall and the sampling slide, the sampling spring being held in a compressed state when the second latch arm is engaged with the second latch strike;

a cannula retract spring interposed between, and connected to each of, the sampling slide and the cannula slide, the cannula retract spring being releasably held in an extended state to store mechanical energy when the first latch arm is engaged with the first latch strike and the second latch arm is engaged with the second latch strike;

a cocking mechanism having a charge handle, a biasing spring, and an indexing mechanism, the charge handle slidably mounted to the housing and biased by the biasing spring in a distal direction to a home position, the charge handle configured to move between the home position and a retracted position, the indexing mechanism being movably coupled to the cannula slide, wherein:

a first retraction of the charge handle moves the sampling slide and the cannula slide in unison in a proximal direction to compress the sampling spring, to engage the second latch arm with the second latch strike to retain the sampling spring in the compressed state, and to charge the vacuum source, the charge handle configured to return to the home position by force exerted by the biasing spring and to sequence the indexing mechanism to a next selection position; and a second retraction of the charge handle moves the charge handle to the retracted position, and during a return of the charge handle to the home position by the force exerted by the biasing spring, the charge handle engages the indexing mechanism movably coupled to the cannula slide, and the cannula slide is moved in the distal direction, which in turn extends the cannula retract spring to the extended state, and the first latch arm releasably engages the first latch strike to retain the cannula retract spring in the extended state, the cannula being positioned to close the side sample port of the stylet; and the actuator mechanism is configured such that:

an actuation of the cannula retract button releases the first latch arm from the first latch strike to in turn release the cannula retract spring to exert a retraction force to move the cannula in the proximal direction to open the side sample port of the stylet and to simultaneously apply the vacuum to the side sample port; and an actuation of the sample acquisition button releases the second latch arm from the second latch strike to release the sampling spring to exert a force to move the cannula in the distal direction to close the side sample port.

23. The biopsy device of claim 22, the carriage assembly configured to move as a whole longitudinally relative to the housing, and further comprising:

the actuator mechanism having a pierce button;

the carriage latch cover member having a carriage latch arm, the carriage latch arm configured to releasably engage the carriage latch strike;

an intermediate wall interposed in the housing between a proximal end wall and a distal end portion; and a prime pierce spring interposed between the intermediate wall and the stylet mount wall, the prime pierce spring configured to store mechanical energy when in a compressed state and configured to bias the carriage assembly as a whole in the distal direction, the prime pierce spring being held in the compressed state when the carriage latch arm is engaged with the carriage latch strike of the actuator mechanism, wherein:

a third retraction of the charge handle prior to operation of the actuator mechanism moves the carriage assembly as a whole in the proximal direction to compress the prime pierce spring, the carriage latch arm configured to engage the carriage latch strike of the actuator mechanism to retain the prime pierce spring in the compressed state; and, prior to actuation of the cannula retract button and the sample acquisition button, an actuation of the pierce button releases the carriage latch arm from the carriage latch strike, the prime pierce spring being released from the compressed state to exert a force to move the carriage assembly, the stylet, and the cannula in unison in the distal direction.

24. A method of operating a biopsy device, comprising:

providing a housing having an actuator mechanism;

providing a carriage assembly movable relative to the housing, the carriage assembly including a stylet mount wall that mounts a stylet, a cannula slide that mounts a cutting cannula, a sampling slide movably interposed between the stylet mount wall and the cannula slide, and a carriage latch cover member, the cannula slide being longitudinally spaced from and movable relative to the stylet mount wall;

providing a charge handle to sequentially move at least one of the cannula slide, the sampling slide, and the carriage assembly as a whole, the charge handle having a home position and a retracted position;

providing a sampling spring interposed between the stylet mount wall and the sampling slide;

providing a cannula retract spring interposed between, and connected to each of, the sampling slide and the cannula slide;

providing a prime pierce spring interposed between the carriage assembly and a portion of the housing;

providing a vacuum system to selectively supply a vacuum to a sample port of the stylet;

retracting the charge handle a first time to move the cannula slide and the sampling slide in unison in a proximal direction to charge the sampling spring, to latch the sampling slide with the carriage latch cover member to retain the sampling spring in a charged state, and to charge the vacuum system to generate the vacuum;

returning the charge handle a first time to the home position;

retracting the charge handle a second time to the retracted position;

returning the charge handle a second time to the home position to move the cannula slide in a distal direction relative to the sampling slide to charge the cannula retract spring and to latch the cannula slide with the carriage latch cover member to retain the cannula retract spring in a charged state; and retracting the charge handle a third time to move the carriage assembly as a whole in the proximal direction to charge the prime pierce spring and to latch the carriage latch cover member with the actuator mechanism to retain the prime pierce spring in a charged state.

25. The method of claim 24, the actuator mechanism having a cannula retract button, a sample acquisition button, and a pierce button, the method further comprising:

actuating the pierce button to unlatch the carriage latch cover member from the actuator mechanism to release the prime pierce spring from the charged state to propel the carriage assembly in the distal direction to facilitate simultaneous distal movement of the stylet and the cannula;

actuating the cannula retract button to unlatch the cannula slide from the carriage latch cover member to release the cannula retract spring from the charged state and move the cannula in the proximal direction to open the sample port of the stylet and to simultaneously apply the vacuum to the sample port; and actuating the sample acquisition button to unlatch the sampling slide from the carriage latch cover member to release the sampling spring from the charged state to propel the cannula in the distal direction to close the sample port.

* * * * *